(12) United States Patent
George et al.

(10) Patent No.: US 10,954,561 B2
(45) Date of Patent: *Mar. 23, 2021

(54) POLYMER COATINGS

(71) Applicant: Illumina, Inc., San Diego, CA (US)

(72) Inventors: Wayne N. George, Cambridge (GB); Andrew A. Brown, Cambridge (GB); Daniel Bratton, Cambridge (GB); Hongji Ren, San Diego, CA (US); Ryan Christopher Smith, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/380,832

(22) Filed: Apr. 10, 2019

(65) Prior Publication Data

US 2019/0233890 A1 Aug. 1, 2019

Related U.S. Application Data

(63) Continuation of application No. 15/680,561, filed on Aug. 18, 2017, now Pat. No. 10,266,891, which is a continuation of application No. 14/679,760, filed on Apr. 6, 2015, now Pat. No. 9,752,186, which is a continuation of application No. 13/784,368, filed on Mar. 4, 2013, now Pat. No. 9,012,022.

(60) Provisional application No. 61/753,833, filed on Jan. 17, 2013, provisional application No. 61/657,508, filed on Jun. 8, 2012.

(51) Int. Cl.
| | |
|---|---|
| *C12Q 1/68* | (2018.01) |
| *C12Q 1/6874* | (2018.01) |
| *B05D 3/06* | (2006.01) |
| *C09D 133/26* | (2006.01) |
| *C09D 135/00* | (2006.01) |
| *C12Q 1/6806* | (2018.01) |

(52) U.S. Cl.
CPC ............ *C12Q 1/6874* (2013.01); *B05D 3/06* (2013.01); *B05D 3/065* (2013.01); *C09D 133/26* (2013.01); *C09D 135/00* (2013.01); *C12Q 1/6806* (2013.01); *Y10T 428/24802* (2015.01); *Y10T 428/24917* (2015.01); *Y10T 428/24926* (2015.01); *Y10T 428/2998* (2015.01); *Y10T 428/31536* (2015.04); *Y10T 428/31935* (2015.04)

(58) Field of Classification Search
CPC ........................... C12Q 1/6874; C09D 133/26
See application file for complete search history.

(56) References Cited

U.S. PATENT DOCUMENTS

| | | |
|---|---|---|
| 4,442,196 A | 4/1984 | Iwaki et al. |
| 4,914,159 A | 4/1990 | Bömer et al. |
| 4,937,000 A | 6/1990 | Bomer et al. |
| 5,130,238 A | 7/1992 | Malek et al. |
| 5,212,253 A | 5/1993 | Ponticello |
| 5,223,414 A | 6/1993 | Zarling et al. |
| 5,302,509 A | 4/1994 | Cheeseman |
| 5,429,807 A | 7/1995 | Matson et al. |
| 5,436,327 A | 7/1995 | Southern |
| 5,455,166 A | 10/1995 | Walker |
| 5,561,071 A | 10/1996 | Hollenberg et al. |
| 5,583,211 A | 12/1996 | Coassin et al. |
| 5,599,675 A | 2/1997 | Brenner |
| 5,641,658 A | 6/1997 | Adams et al. |
| 5,654,413 A | 8/1997 | Brenner |
| 5,658,734 A | 8/1997 | Brock et al. |
| 5,750,341 A | 5/1998 | Macevicz |
| 5,837,858 A | 11/1998 | Brennan |
| 5,858,653 A | 1/1999 | Duran et al. |
| 5,874,219 A | 2/1999 | Rava et al. |
| 5,919,523 A | 7/1999 | Sundberg et al. |
| 5,948,621 A | 9/1999 | Gaber et al. |
| 6,077,674 A | 6/2000 | Tom-Moy et al. |
| 6,136,269 A | 10/2000 | Winkler et al. |
| 6,210,891 B1 | 4/2001 | Myren et al. |
| 6,214,587 B1 | 4/2001 | Dattagupta |
| 6,221,635 B1 | 4/2001 | Rovera et al. |

(Continued)

FOREIGN PATENT DOCUMENTS

| | | |
|---|---|---|
| EP | 0282770 B1 | 9/1988 |
| EP | 0742287 A2 | 11/1996 |

(Continued)

OTHER PUBLICATIONS

Adessi, et al., "Solid Phase DNA amplification: characterisation of primer attachment and amplification mechanisms", Nucleic Acids Research 28, 2000, 1-8.
Al-Bataineh, et al., "Covalent Immobilization of Antibacterial Furanones via Photochemical Activation of Perfluorophenylazide", Langmuir 25(13): 2009, 7432-7437.
Andreadis, et al., "Use of immobilized PCR primers to generate covalently immobilized DNAs for in vitro transcription/translation reactions", Nucl. Acids Res. 28(2), e5, 2000.
Bentley, et al., "Accurate whole human genome sequencing using reversible terminator chemistry", Nature, vol. 456, 2008, 53-59.
Binnig, et al., "Scanning Tunneling Microscopy", Helvetica Physica Acta vol. 55, 1982, 726-735.

(Continued)

*Primary Examiner* — Kuo Liang Peng
(74) *Attorney, Agent, or Firm* — Knobbe, Martens, Olson & Bear, LLP

(57) ABSTRACT

The present disclosure relates to polymer coatings covalently attached to the surface of a substrate and the preparation of the polymer coatings, such as poly(N-(5-azidoacetamidylpentyl)acrylamide-co-acrylamide) (PAZAM), in the formation and manipulation of substrates, such as molecular arrays and flow cells. The present disclosure also relates to methods of preparing a substrate surface by using beads coated with a covalently attached polymer, such as PAZAM, and the method of determining a nucleotide sequence of a polynucleotide attached to a substrate surface described herein.

27 Claims, 21 Drawing Sheets

(56) References Cited

U.S. PATENT DOCUMENTS

| | | |
|---|---|---|
| 6,258,568 B1 | 7/2001 | Nyren |
| 6,274,320 B1 | 8/2001 | Romberg et al. |
| 6,287,776 B1 | 9/2001 | Hefti |
| 6,288,220 B1 | 9/2001 | Kambara et al. |
| 6,291,193 B1 | 9/2001 | Khodadoust |
| 6,297,006 B1 | 10/2001 | Drmanac |
| 6,346,413 B1 | 2/2002 | Fodor et al. |
| 6,355,431 B1 | 3/2002 | Chee et al. |
| 6,372,813 B1 | 4/2002 | Johnson et al. |
| 6,416,949 B1 | 7/2002 | Dower et al. |
| 6,465,178 B2 | 10/2002 | Chappa et al. |
| 6,482,591 B2 | 11/2002 | Lockhart et al. |
| 6,514,751 B2 | 2/2003 | Johann et al. |
| 6,524,793 B1 | 2/2003 | Chandler et al. |
| 6,610,482 B1 | 8/2003 | Fodor et al. |
| 6,699,693 B1 | 3/2004 | Marians et al. |
| 6,737,236 B1 | 5/2004 | Pieken et al. |
| 6,890,741 B2 | 5/2005 | Fan et al. |
| 6,913,884 B2 | 7/2005 | Stuelpnagel et al. |
| 6,929,915 B2 | 8/2005 | Benkovic et al. |
| 7,057,026 B2 | 6/2006 | Barnes et al. |
| 7,115,400 B1 | 10/2006 | Adessi et al. |
| 7,211,414 B2 | 5/2007 | Hardin et al. |
| 7,244,559 B2 | 7/2007 | Rothberg et al. |
| 7,315,019 B2 | 1/2008 | Turner et al. |
| 7,329,492 B2 | 2/2008 | Hardin et al. |
| 7,375,234 B2 | 5/2008 | Sharpless et al. |
| 7,399,590 B2 | 7/2008 | Piepenburg et al. |
| 7,405,281 B2 | 7/2008 | Xu et al. |
| 7,427,678 B2 | 9/2008 | Pieken et al. |
| 7,582,420 B2 | 9/2009 | Oliphant et al. |
| 7,595,883 B1 | 9/2009 | El Gamal et al. |
| 7,763,736 B2 | 7/2010 | Sharpless et al. |
| 7,785,790 B1 | 8/2010 | Church et al. |
| 8,017,339 B2 | 9/2011 | Piepenburg et al. |
| 8,062,850 B2 | 11/2011 | Piepenburg |
| 8,071,308 B2 | 12/2011 | Piepenburg et al. |
| 9,012,022 B2 | 4/2015 | George et al. |
| 2001/0014448 A1 | 8/2001 | Chappa et al. |
| 2002/0055100 A1 | 5/2002 | Kawashima et al. |
| 2002/0102578 A1 | 8/2002 | Dickinson et al. |
| 2003/0008413 A1 | 1/2003 | Kim et al. |
| 2003/0044389 A1 | 3/2003 | Brown et al. |
| 2003/0157260 A1 | 8/2003 | Rubner et al. |
| 2004/0002090 A1 | 1/2004 | Mayer et al. |
| 2004/0096853 A1 | 5/2004 | Mayer |
| 2004/0248144 A1 | 12/2004 | Mir |
| 2005/0053980 A1 | 3/2005 | Gunderson et al. |
| 2005/0064460 A1 | 3/2005 | Holliger et al. |
| 2005/0074478 A1 | 4/2005 | Ofstead et al. |
| 2005/0130173 A1 | 6/2005 | Leamon et al. |
| 2005/0181440 A1 | 8/2005 | Chee et al. |
| 2005/0191698 A1 | 9/2005 | Chee et al. |
| 2007/0099208 A1 | 5/2007 | Drmanac et al. |
| 2007/0128624 A1 | 6/2007 | Gormley et al. |
| 2008/0009420 A1 | 1/2008 | Schroth et al. |
| 2008/0108082 A1 | 5/2008 | Rank et al. |
| 2009/0026082 A1 | 1/2009 | Rothberg et al. |
| 2009/0032401 A1 | 2/2009 | Ronaghi et al. |
| 2009/0127589 A1 | 5/2009 | Rothberg et al. |
| 2009/0186349 A1 | 7/2009 | Gunderson et al. |
| 2010/0111768 A1 | 5/2010 | Banerjee et al. |
| 2010/0137143 A1 | 6/2010 | Rothberg et al. |
| 2010/0273931 A1* | 10/2010 | Dogra ............... C08F 293/005 524/521 |
| 2010/0282617 A1 | 11/2010 | Rothberg |
| 2011/0059865 A1 | 3/2011 | Smith et al. |
| 2012/0270305 A1 | 10/2012 | Reed et al. |
| 2012/0316086 A1 | 12/2012 | Lin et al. |
| 2013/0116153 A1 | 5/2013 | Bowen et al. |
| 2013/0225421 A1 | 8/2013 | Li et al. |
| 2013/0338042 A1 | 12/2013 | Shen et al. |

FOREIGN PATENT DOCUMENTS

| | | |
|---|---|---|
| EP | 0799897 A1 | 11/1996 |
| JP | H02-37350 A | 2/1990 |
| JP | 11/507105 | 6/1999 |
| JP | 2012-201634 | 10/2012 |
| WO | 1989/10977 A1 | 11/1989 |
| WO | 1991/006678 A1 | 5/1991 |
| WO | 1993/017126 A1 | 9/1993 |
| WO | 1995/11995 A1 | 5/1995 |
| WO | 1995/35505 | 12/1995 |
| WO | 1996/039821 A1 | 12/1996 |
| WO | 1997/004131 A1 | 2/1997 |
| WO | 1998/044151 A1 | 10/1998 |
| WO | 1998/044152 A1 | 10/1998 |
| WO | 1999/061653 A2 | 12/1999 |
| WO | 2000/006770 | 2/2000 |
| WO | 2000/018957 A1 | 4/2000 |
| WO | 2000/031148 A2 | 6/2000 |
| WO | 2000/046408 A1 | 8/2000 |
| WO | 2000/053812 A2 | 9/2000 |
| WO | 2000/063437 A2 | 10/2000 |
| WO | 2001/001143 A2 | 1/2001 |
| WO | 2001/023082 A2 | 4/2001 |
| WO | 2001/062982 A2 | 8/2001 |
| WO | 2001/066554 A2 | 9/2001 |
| WO | 2002/012566 A2 | 2/2002 |
| WO | 2002/046759 A1 | 6/2002 |
| WO | 2002/059372 A2 | 8/2002 |
| WO | 2003/014392 A2 | 2/2003 |
| WO | 2003/014394 A1 | 2/2003 |
| WO | 2003/074734 A2 | 9/2003 |
| WO | 2004/002618 A1 | 1/2004 |
| WO | 2004/018497 A2 | 3/2004 |
| WO | 2004/073843 A1 | 9/2004 |
| WO | 2005/010145 A2 | 2/2005 |
| WO | 2005/047301 A1 | 5/2005 |
| WO | 2006/020775 A2 | 2/2006 |
| WO | 2007/123744 A2 | 11/2007 |
| WO | 2008/093098 A2 | 8/2008 |
| WO | 2009/099126 | 8/2009 |
| WO | 2011082500 A1 | 7/2011 |
| WO | 2012/010607 A1 | 1/2012 |
| WO | 2012/058096 A1 | 5/2012 |
| WO | 2012/106072 | 8/2012 |
| WO | 2012/170936 | 12/2012 |

OTHER PUBLICATIONS

Braslavsky, et al., "Sequence information can be obtained from single DNA molecules", PNAS, 100(7), Apr. 1, 2003, 3960-3964.

Dean, et al., "Comprehensive human genome amplification using multiple displacement amplification", Proc. Natl. Acad. Sci. USA 99, 2002, 5261-5266.

Dressman, et al., "Transforming single DNA molecules into fluorescent magnetic particles for detection and enumeration of genetic variations", Proc. Natl. Acad. Sci. USA 100 (15), 2003, 8817-8822.

Efimov, et al., "Synthesis of polyacrylamides N-substituted with PNA-like oligonucleotide mimics for molecular diagnostic applications", Nucleic Acids Research, 27(22), 1999, 4416-4426.

Fleet, et al., "Affinity Labelling of Antibodies with Aryl Nitrene as Reactive Group", Nature 224, 1969, 511-512.

Fodor, et al., "Use of immobilized PCR primers to generate covalently immobilized DNAs for in vitro transcription/ translation reactions", Trends in Biotechnology 12, Jan. 1994, 19-26.

Gritsan, et al., "Photochemistry of Azides: The Azide/Nitrene Interface, in Organic Azides: Syntheses and Applications", 2010, 311-364.

Guo, et al., "Direct fluorescence analysis of genetic polymorphisms by hybridization with oligonucleotide arrays on glass supports", Nucleic Acids Research, vol. 22(24), 1994, 5456-5465.

Hansma, et al., "Biomolecular Imaging with the Atomic Force Microscope", Annual Review Biophys. Biomo. Struct. vol. 23, 1994, 115-139.

Huber, et al., "Detection of Single Base Alterations in Genomic DNA by Solid Phase Polymerase Chain Reaction on Oligonucleotide Microarrays", Analytical Biochemistry, 299, 2001, 24-30.

(56) References Cited

OTHER PUBLICATIONS

Kartalov, et al., "Polyelectrolyte Surface Interface for Single-Molecule Fluorescence Studies of DNA Polymerase", Biotechniques vol. 34, No. 3, 2003, 505-510.
Keana, et al., "New reagents for photoathnity labeling: synthesis and photolysis of functionalized perfluorophenyl azides", J. Org. Chem. 55, 1990, 3640-3647.
Krulle, et al., "Triazole carboxylic acids as anionic sugar mimics? Inhibition of glycogen phosphorylase by a d-glucotriazole carboxylate", Tetrahedron: Asymmetry 8(2), 1997, 3807-3820.
Lage, et al., "Whole genome analysis of genetic alterations in small DNA samples using hyperbranched strand displacement amplification and array-CGH", Genome Res., 2003, 294-307.
Lizardi, "Mutation detection and single-molecule counting using isothermal rolling-circle amplification", Nature Genetics, vol. 19, 1998, 225-232.
Mitra, et al., "In situ localized amplification and contact replication of many individual DNA molecules", Nucleic Acids Research, Oxford University Press, GB vol. 27, No. 24, 1999, e34.
Moyer, et al., "Samples can be imaged with resolution better than the wavelength of light using laser illumination through a small fiber tip", Laser Focus World 29(10), 1993, 105-109.
PCT/US2013/044305, "International Preliminary Examination Report on Patentability", dated Jun. 12, 2014, 19 Pages.
PCT/US2013/044305, "International Search Report and Written Opinion", dated Aug. 28, 2013, 8 Pages.
Peterson, et al., "The effect of surface probe density on DNA hybridization", Nucl. Acids Res. 29(24), 2001, 5163-5168.
Pirrung, et al., "Novel reagents and procedures for immobilization of DNA on glass microchips for primer extension", Langmuir ACS Washington DC, US vol. 16, 2000, 2185-2191.
Raghuraman, et al., "Attachment of polymer films to solid surfaces via thermal activation of self-assembled monolayers containing sulphonyl azide group", Langmuir 26(2), 2010, 769-774.
Sambrook, et al., "Molecular Cloning: A Laboratory Manual", Chapter 10, 3rd Edition, Cold Spring Harbor Laboratory, New York, 2001.
Schena, et al., "Quantitative Monitoring of Gene Expression Patterns with a Complementary DNA Microarray", Science vol. 270, 1995, 467-470.
Shapero, et al., "SNP Genotyping by multiplexed solid-phase amplification and fluorescent minisequencing", Genome Research vol. 11, No. 11, 2001, 1926-1934.
Shchepinov, et al., "Steric factors influencing hybridisation of nucleic acids to oligonucleotide arrays", Nucl. Acids Res., vol. 25, No. 6, 1997, 1155-1161.
Sjoroos, et al., "Solid-Phase PCR with Hybridization and Time-resolved Fluorometry for Detection of HLA-B27", Clin. Chem. 47(3), 2001, 498-504.
Stamm, et al., "Sanchored PCR: PCR with cDNA coupled to a solid phase", Nucl. Acids Res. 19(6), 1991, 1350.
Vale, et al., "Direct Observation of Single Kinesin Molecules moving along microtubules", Nature vol. 380, 1996, 451-453.
Walker, et al., "Strand displacement amplification—an isothermal, in vitro DNA amplification technique", Nucleic Acids Res., 1992, 1691-1696.
Weiler, et al., "Hybridisation based DNA screening on peptide nucleic acid (PNA) oligomer arrays", Nucl. Acids Res. 25(14), 1997, 2792-2799.
Zhao, et al., "Immobilization of oligodeoxyribonucleotides with multiple anchors to microchips", Nucleic Acids Research 29, 2001, 955-959.
Gains, et al., "A novel method for nucleic acid sequence determination", J. Theor Biol., 135(3), 1988, 303-307.
Drmanac, et al., "Accurate sequencing by hybridization for DNA diagnostics and individual genomics", Nature Biotechnology, 1998, 54-58.
Korlach, et al., "Selective aluminum passivation for targeted immobilization of single DNA polymerase molecules in zero-mode waveguide nanostructures", PNAS, vol. 105 No. 4, 2008, 1176-1181.
Levene, et al., "Zero-Mode Waveguides for Single-Molecule Analysis at high concentrations", Science 299, 2003, 382-686.
Lundquist, et al., "Parallel confocal detection of single molecules in real time", Opt. Lett. 33(9), 2008, 1026-1028.
Ronaghi, M, et al., "A Sequencing Method Based on Real-Time Pyrophosphate", Science 281 (5375), Jul. 17, 1998, 363-365.
Ronaghi, M., "Pyrosequencing sheds light on DNA sequencing", Genome Res, 11(1), 2001, 3-11.
Ronaghi, M, et al., "Real-time DNA sequencing using detection of pyrophosphate release", Anal. Biochem. Nov. 1, 1996; 242 (1):84-9, Nov. 1, 1996, 84-89.
Shendure, et al., "Accurate Multiplex Polony Sequencing of an Evolved Bacterial Genome", Science, Sep. 9, 2005, 1728-1732.
Walker, et al., "A Chemiluminescent DNA Probe Test Based on Strand Displacement Amplification", Molecular Methods for Virus Detection, 1995, Academic Press Inc. Ch 15 pp. 329-349., 1995, 329-349.

\* cited by examiner

Lane 1: *In situ* standard SFA
Lanes 2-8: *In situ* PAZAM (0.25%w/v)

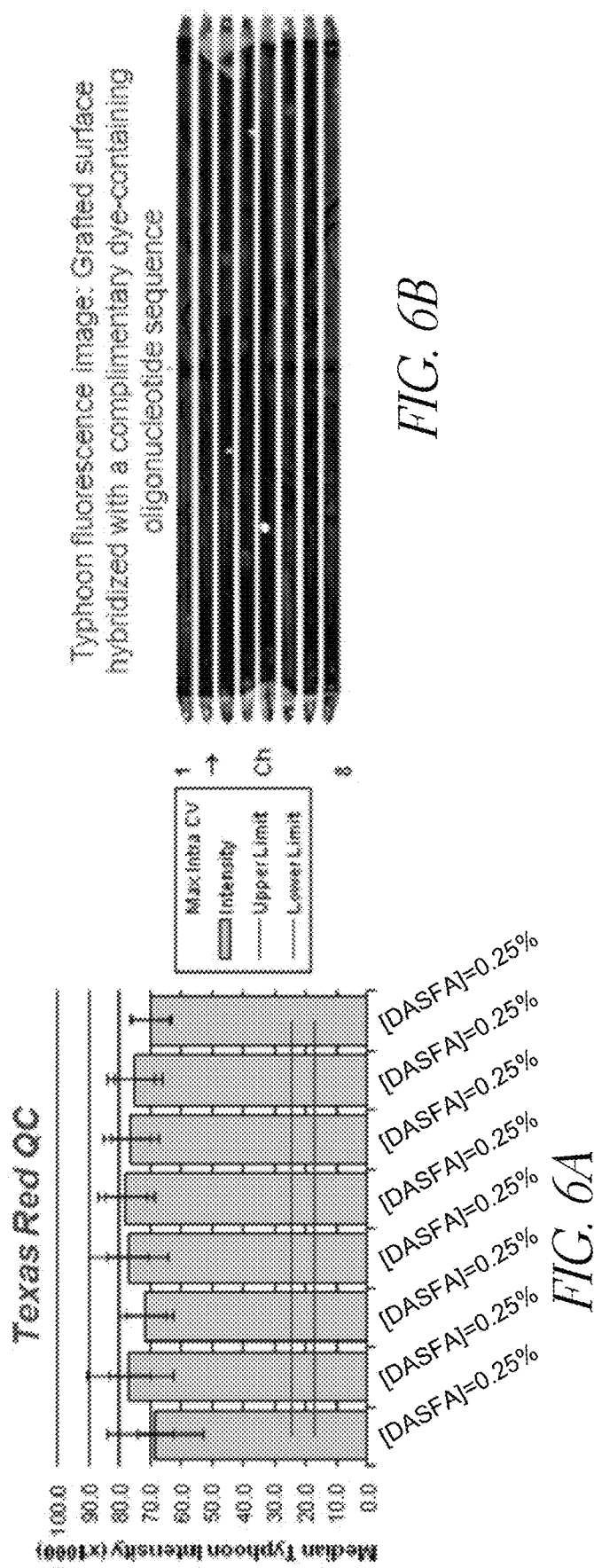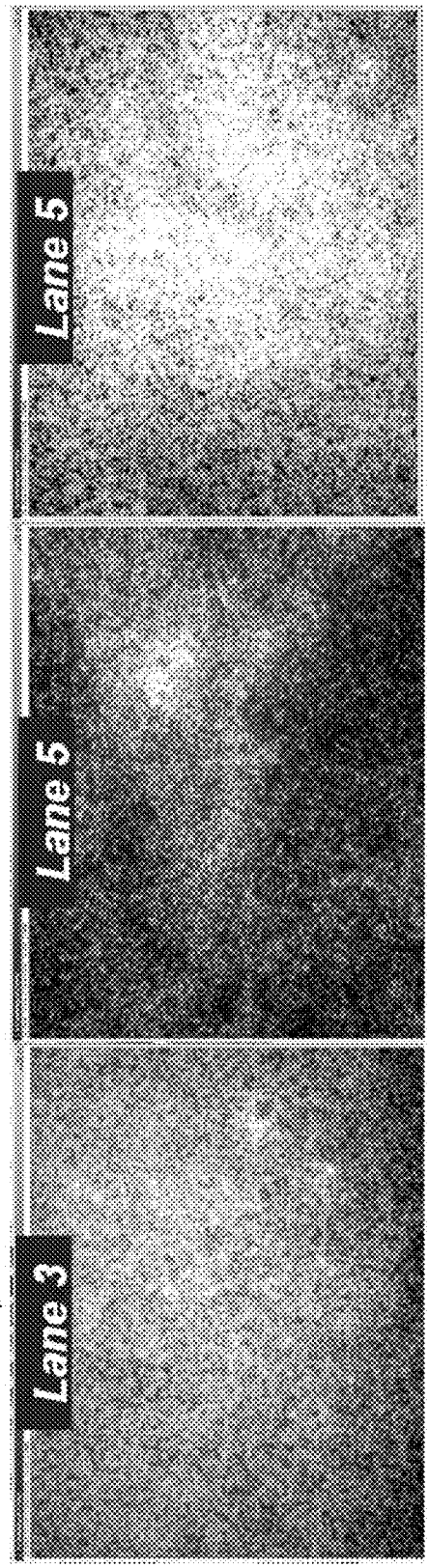
FIG. 6A  FIG. 6B  FIG. 6C

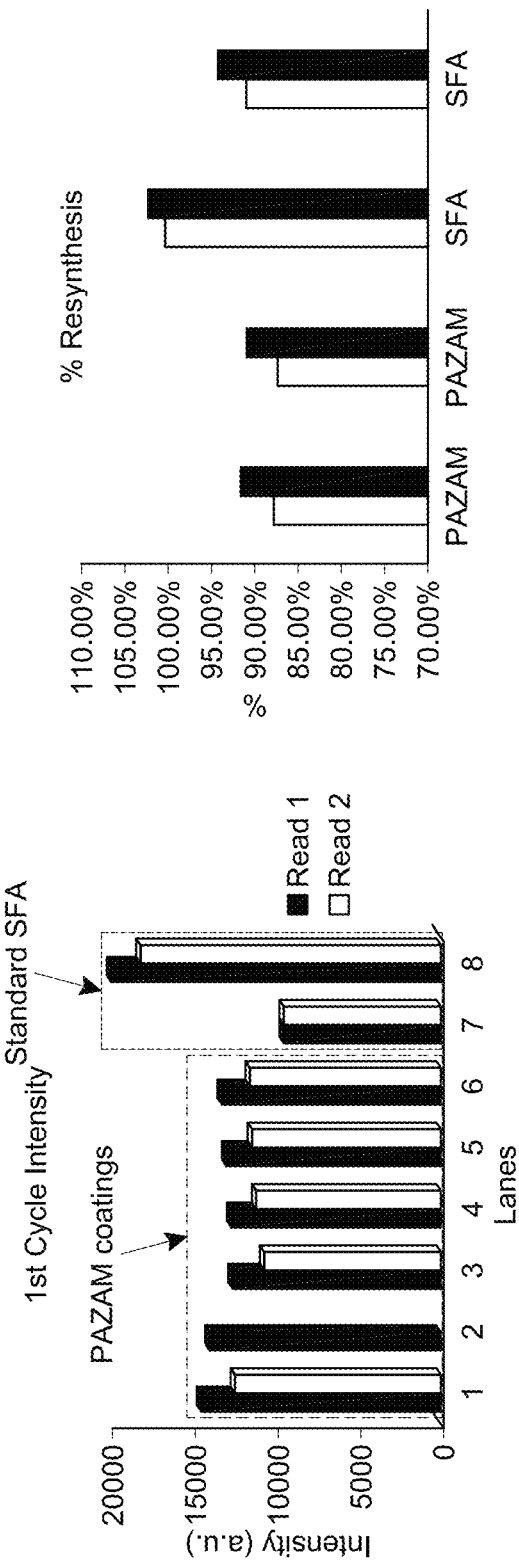
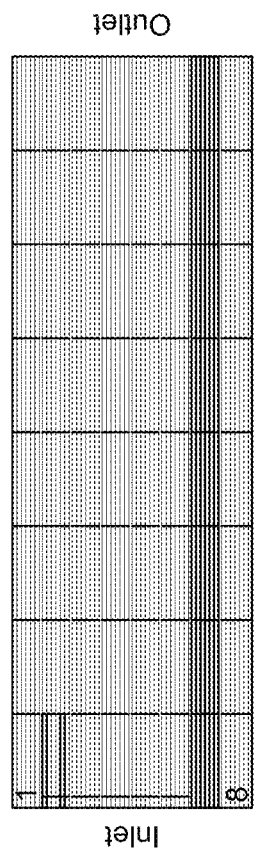
FIG. 8A
FIG. 8B
FIG. 8C

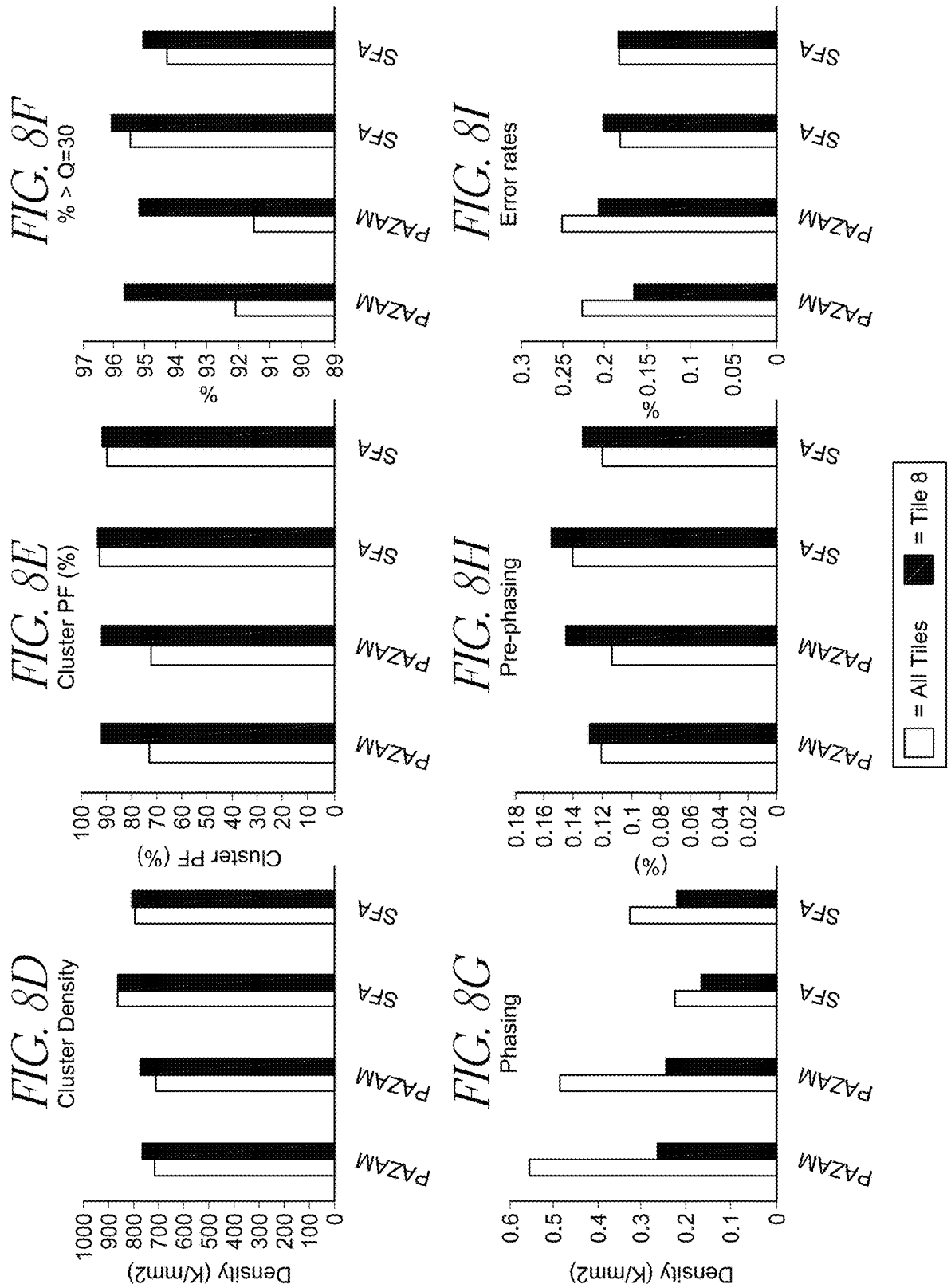

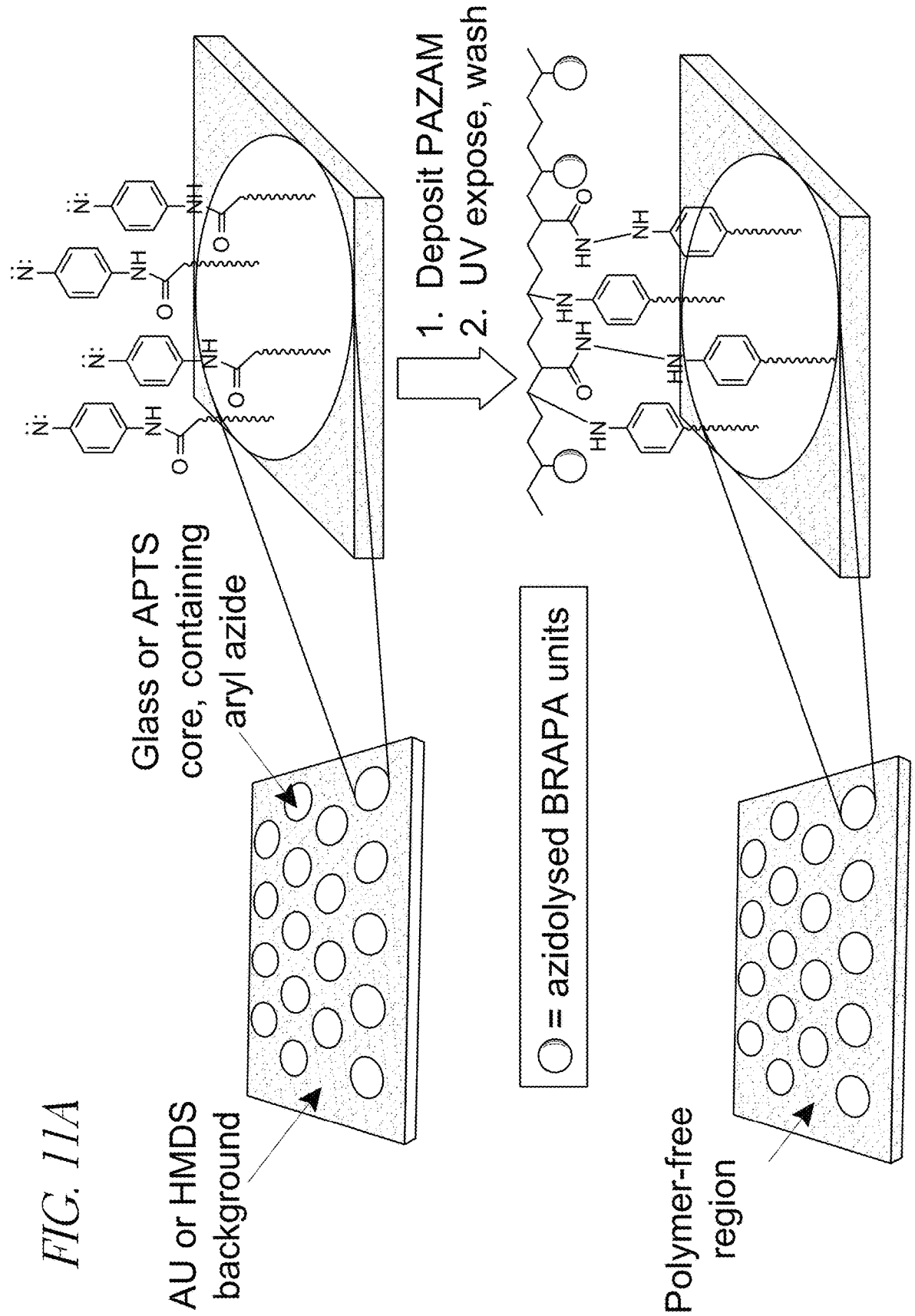

| Lane | Density (k/mm²) | % PF | Phas/ Prep (%) | Intensity | % Int. after 20 cycles | % ≥ Q30 | % Resynthesis |
|---|---|---|---|---|---|---|---|
| 1 | 174 +/- 13 | 95.2 +/- 6.3 | 0.233 / 0.251 | 15159 +/- 2627 | 79.8 +/- 3.0 | 98.8 | 85 |
| 2 | 178 +/- 14 | 96.5 +/- 3.1 | 0.230 / 0.239 | 16739 +/- 2598 | 81.3 +/- 4.4 | 98.8 | 89 |
| 3 | 161 +/- 15 | 96.4 +/- 2.9 | 0.211 / 0.242 | 13839 +/- 1618 | 80.2 +/- 3.6 | 99 | 85 |
| 4 | 170 +/- 14 | 94.6 +/- 7.8 | 0.267 / 0.232 | 16977 +/- 2044 | 79.8 +/- 6.4 | 98.6 | 88 |
| 5 | 101 +/- 43 | 74.7 +/- 31.0 | 0.250 / 0.257 | 9749 +/- 6047 | 114.4 +/- 97.1 | 97.3 | 97 |
| 6 | 136 +/- 11 | 94.9 +/- 9.5 | 0.265 / 0.252 | 15321 +/- 1978 | 77.6 +/- 4.1 | 98.6 | 84 |
| 7 | 120 +/- 7 | 89.0 +/- 24.4 | 0.138 / 0.201 | 14161 +/- 1727 | 80.0 +/- 2.3 | 87.5 | 42 |
| 8 | 132 +/- 21 | 87.3 +/- 20.3 | 0.221 / 0.258 | 13156 +/- 2959 | 81.2 +/- 13.8 | 98.7 | 85 | ns
POLYMER COATINGS

CROSS-REFERENCE TO RELATED APPLICATIONS

The present application is a continuation of U.S. application Ser. No. 15/680,561, filed Aug. 18, 2017, to be issued as U.S. Pat. No. 10,266,891 on Apr. 23, 2019, which is a continuation of U.S. application Ser. No. 14/679,760, filed Apr. 6, 2015, now U.S. Pat. No. 9,752,186, which is a continuation of U.S. application Ser. No. 13/784,368, filed Mar. 4, 2013, now U.S. Pat. No. 9,012,022, which claims the benefit of priority to U.S. Appl. No. 61/657,508, filed Jun. 8, 2012 and U.S. Appl. No. 61/753,833, filed Jan. 17, 2013, all of which are hereby incorporated by reference in their entirety.

FIELD

In general, the present invention relates to the fields of chemistry, biology and material science. More specifically the present invention relates to polymer coatings covalently attached to a surface of a substrate that is used for the detection and/or analysis of molecules, such as nucleic acids and proteins.

BACKGROUND

Polymer-coated substrates are used in many technological applications. For example, implantable medical devices can be coated with biologically inert polymers. In another example, polymer coated substrates are used for the preparation and/or analysis of biological molecules. Molecular analyses, such as certain nucleic acid sequencing methods, rely on the attachment of nucleic acid strands to a polymer-coated surface of a substrate. The sequences of the attached nucleic acid strands can then be determined by a number of different methods that are well known in the art.

In certain sequencing-by-synthesis processes, one or more surfaces of a flow cell are coated with a polymer to which nucleic acids are attached. The current procedure used to coat flow cells involves transferring a polymerizing mix into channels on the flow cell and incubating for a fixed time period. This procedure is simple and results in reliable coatings that are consistently able to support all downstream chemical processing steps including bridge amplification and sequencing.

There are, however, several limitations to many of the currently-used surface polymer coatings. For example, (i) some of the current approaches limit the methods that can be used to coat surfaces because air-sensitive polymer mix is required; (ii) some of the formed coatings have to be stored in a "wet" state, for example, in aqueous solution; and (iii) grafting conditions often need to be optimized in order to avoid intensity gradients.

In addition, there is also a need to create patterned flowcells with defined features periodically spaced. One method of creating patterned flowcells is to chemically modify a bead, and then apply that bead to a pre-arrayed surface with the surface containing open wells which can accommodate the beads. The beads can be coated with a polymer that can support cluster-growth based sequencing prior to loading them into the wells. Polymer coatings that are useful on planar array surfaces may not be convenient for coating beads due to aggregation caused by the coating and requirements to store the beads in aqueous buffers after coating. This results in some limitations in commercial applications. Accordingly, there is a need for new polymer coatings that do not suffer from one or more of the disadvantages of current polymer coatings when used to coat beads.

SUMMARY

Some embodiments of the compositions described herein relate to substrates having one or more surfaces comprising an improved polymer coating. In some embodiments, the substrate is a flow cell and the polymer coating is applied to one or more surfaces of one or more lanes of the flow cell.

Some embodiments of the compositions described herein relate to a substrate comprising a surface, wherein a polymer coating is covalently attached to the surface. Other embodiments of the compositions described herein relate to a substrate comprising a functionalized surface, wherein a polymer coating is covalently attached to a series of functional groups on the surface and wherein the functional groups are selected from the group consisting of alkene, alkyne, nitrene, aldehyde, hydrazine, activated ester, glycidyl ether, amine, maleimide and benzoyl ester with a phosphine substituent in the ortho position for Staudinger ligation. Still other embodiments provide a substrate comprising a surface having a polymer coating comprising recurring units of Formulae (I) and (II). In certain embodiments, the recurring unit of Formula (I) is also represented by Formula (Ia). In other embodiments, the recurring unit of Formula (I) is also represented by Formula (Ib). In some embodiments, the polymer coating comprises a polymer of Formula (III) or (III'). In one embodiment, the polymer coating comprises a polymer of Formula (IIIa). In one embodiment, the polymer coating comprises a polymer of Formula (IIIb). In another embodiment, the polymer coating comprises a polymer of Formula (IV).

Some embodiments of the methods described herein relate to preparing a polymer coating immobilized to a surface of a substrate. In some embodiments the method comprises contacting a polymer with a surface of a substrate, wherein the surface comprises a plurality of functional groups, thereby forming a layer of polymer coating over the surface. In some embodiments, the polymer coating is covalently bonded to the functional groups on the surface of the substrate. In some embodiments, the polymer is formed in situ on the surface of the substrate by polymerizing a polymerizable material on the surface of the substrate. In some other embodiment, the polymer is pre-formed before contacting with the surface of the substrate. In certain embodiments, the functional groups are selected from the group consisting of alkene, alkyne, nitrene, aldehyde, hydrazine, activated ester, glycidyl ether, amine, maleimide, and benzoyl ester with a phosphine substituent in the ortho position for Staudinger ligation. In certain embodiments, the functional groups on the surface of the substrate comprise optionally substituted phenyl azide groups. In other embodiments, the functional groups on the surface of the substrate comprise alkyne groups. In still other embodiments, the functional groups on the surface of the substrate comprise alkene groups. In certain embodiments, the polymer coating comprises recurring units of Formulae (I) and (II). In certain embodiments, the recurring unit of Formula (I) is also represented by Formula (Ia). In certain embodiments, the recurring unit of Formula (I) is also represented by Formula (Ib). In some embodiments, the polymer coating comprises a polymer of Formula (III) or (III'). In one embodiment, the polymer coating comprises a polymer of Formula (IIIa). In one embodiment, the polymer of Formula (III') is also represented by Formula (IIIb). In another embodiment, the polymer coating comprises a polymer of Formula (IV). In some embodiments, the polymer coating is dissolved in an aqueous solution before covalently bonding to the functional groups of the surface.

Other embodiments of the methods described herein relate to preparing an array of polynucleotides. In such embodiments, the methods can comprise the steps of reacting a plurality of oligonucleotides with reactive sites present in the polymer coating of any of the compositions described herein or polymer coatings prepared by any of the methods described herein; contacting the plurality of oligonucleotides attached to the polymer coating with templates to be amplified, each template comprising a sequence capable of hybridizing to the oligonucleotides; and amplifying the templates using the oligonucleotides, thereby generating a clustered array of polynucleotides. In some embodiments two primers can be used, one or both of which can be attached to the polymer coating. For example, the methods can comprise the steps of reacting a plurality of first oligonucleotides with reactive sites present in the polymer coating of any of the compositions described herein or polymer coatings prepared by any of the methods described herein; contacting the plurality of first oligonucleotides attached to the polymer coating with templates to be amplified, each template comprising at the 3' end a sequence capable of hybridizing to the first oligonucleotides and at the 5' end a sequence the complement of which is capable of hybridizing to a second oligonucleotides; and amplifying the templates using the first oligonucleotides and the second oligonucleotides, wherein the second oligonucleotide is optionally attached to the polymer coating, thereby generating a clustered array of polynucleotides. In some embodiments of such methods, the first oligonucleotides or the second oligonucleotides comprise alkyne groups to be reacted with azido groups of the polymer coating. In other embodiments of such methods, the first oligonucleotides or the second oligonucleotides comprise amine groups to be reacted with cyanuric chloride present in the polymer coating. In still other embodiments of such methods, the first oligonucleotides or the second oligonucleotides comprise aldehyde groups to be reacted with activated amine groups, such as hydrazinyl or hydrazonyl groups, of the polymer coating. In yet other embodiments of such methods, the first oligonucleotides or the second oligonucleotides comprise amine groups to be reacted with thiocyanate or carboxylic acid groups of the polymer coating. In further embodiments of such methods, the first oligonucleotides or the second oligonucleotides comprise amine groups to be reacted with glycidyl groups of the polymer coating. In still further embodiments of such methods, the first oligonucleotides or the second oligonucleotides comprise amine groups to be reacted with amine groups of the polymer coating via a di-aldehyde linker. In yet other embodiments of such methods, the first oligonucleotides or the second oligonucleotides comprise amine groups to be reacted with activated ester or epoxy groups present in the polymer coating. In yet other embodiments of such methods, the first oligonucleotides or the second oligonucleotides comprise aldehyde groups to be reacted with the oxo-amine groups present in the polymer coating. In some embodiments of such methods, the polymer coating is washed with water or aqueous buffer before reacting with the plurality of the first oligonucleotides and the plurality of second oligonucleotides. In one embodiment, the polymer coating comprises a polymer of Formula (III). In another embodiment, the polymer coating comprises a polymer of Formula (III').

Some embodiments of the compositions described herein relate to a flow cell comprising any one of the substrate compositions described herein. Some such embodiments further comprise polynucleotides attached to the surface of the substrate via the polymer coating. In some embodiments, the polynucleotides are present in polynucleotide clusters. In some such embodiments, polynucleotides within a single polynucleotide cluster have the same nucleotide sequence. Individual polynucleotides in a cluster can be attached to the polymer coating at one end or at both ends. The attachment(s) can be via the 5' and/or 3' end of a strand of the polynucleotide. Polynucleotides of different polynucleotide clusters generally have different nucleotide sequences, but this is not necessary in all embodiments.

Some embodiments of the methods described herein relate to determining a nucleotide sequence of a polynucleotide. Some such embodiments comprise the steps of: (a) contacting a polynucleotide polymerase with polynucleotide clusters attached to a surface of any one of the compositions described herein via the polymer coating; (b) providing nucleotides to the surface of the substrate such that a detectable signal is generated when one or more nucleotides are utilized by the polynucleotide polymerase; (c) detecting signals at one or more polynucleotide clusters; and (d) repeating steps (b) and (c), thereby determining a nucleotide sequence of a polynucleotide present at the one or more polynucleotide clusters. In some such embodiments, the surface of the substrate is present within a flow cell. In some such embodiments, only a single type of nucleotide is present in the flow cell during a single flow step. In such embodiments, the nucleotide can be selected from dATP, dCTP, dGTP, dTTP and analogs thereof. In other embodiments of the methods of determining a nucleotide sequence of a polynucleotide, a plurality different types of nucleotides are present in the flow cell during a single flow step. In such embodiments, the nucleotides can be selected from dATP, dCTP, dGTP, dTTP and analogs thereof. In further embodiments of the methods of determining a nucleotide sequence of a polynucleotide, the detectable signal comprises and optical signal. In other embodiments, the detectable signal comprises a non-optical signal. In such embodiments, the non-optical signal can be a change in pH or a change in concentration of pyrophosphate.

Some embodiments described herein relate to a method of preparing an array of beads. In some embodiments, the method comprises forming a plurality of functional groups on the surface of one or more beads; contacting a polymer coating described herein with the beads to form a polymer coating layer on the surface of the beads, wherein the polymer coating is covalently bonded to the functional groups on the surface of the beads. The polymer coated beads can be loaded onto the surface of a substrate before or after being coated. In some embodiments, the surface can include open wells and each well can have dimensions that accommodate one or more beads (i.e. in some embodiments the wells may accommodate no more than a single bead). In some embodiments, the functional groups on the surface of the beads comprise acrylamide groups. In some embodiments, the functional groups on the surface of the beads comprise optionally substituted phenyl azide groups. In some embodiments, the functional groups on the surface of the beads comprise alkyne groups. In certain embodiments, the polymer coating comprises recurring units of Formulae (I) and (II). In certain embodiments, the recurring unit of Formula (I) is also represented by Formula (Ia). In certain embodiments, the recurring unit of Formula (I) is also represented by Formula (Ib). In some embodiments, the polymer coating comprises a polymer of Formula (III) or (III'). In one embodiment, the polymer of Formula (III) is also represented by Formula (IIIa). In one embodiment, the polymer of Formula (III') is also represented by Formula (IIIb). In another embodiment, the polymer coating comprises a polymer of Formula (IV). In certain embodiments, the beads are entirely coated with the polymer coating described herein. In other embodiments, the beads are partially coated with the polymer coating described herein. In some embodiments, the polymer coating is covalently bonded to the surface of the beads at an elevated temperature. In some other embodiments, the polymer coating is covalently bonded to the surface of the beads via photo activation. In some other embodiments, beads are pre-arrayed in wells and polymer coating is then covalently bonded to the arrayed beads.

The bead can be affixed to the surface of a substrate (e.g., a flow cell or well) via chemical, physioadsorptive, or both forces. In some embodiments, the polymer coated beads are affixed to the surface of the substrate by loading them into open wells on the surface of the substrate. Alternatively or additionally, the polymer coated beads are affixed to the surface of the substrate by covalently binding to the functional groups on the surface of the substrate. In certain embodiments, the methods described herein further comprises washing the polymer coated beads to remove excess unbounded polymer coating before loading the beads to the surface of the substrate. In certain embodiments, the polymer coating is dissolved in a solution before contacting with the pretreated beads. In some embodiments, the polymer coating is dissolved in an aqueous solution. In certain embodiments, the methods described herein further include additional steps to form an arrayed polynucleotides using similar methods as described herein. In some embodiments, the surface of the substrate is patterned with wells, pads or other features.

Some preferred embodiments described herein relate to a substrate having a surface comprising a polymer coating covalently attached thereto, wherein the polymer coating comprises a polymer of Formula (III) or (III'). In one embodiment, the polymer of Formula (III) is also represented by Formula (IIIa). In one embodiment, the polymer of Formula (III') is also represented by Formula (IIIb). In one embodiment, the substrate is a bead.

Some preferred embodiments described herein relate to a method to prepare a surface of a substrate comprises: forming a plurality of functional groups on the surface of the substrate, contacting a polymer of Formula (III) or (III') with the surface of the substrate to form a polymer coating layer on the surface of the substrate, wherein the polymer coating is covalently bonded to the functional groups on the surface of the substrate. In one embodiment, the polymer of Formula (III) is also represented by Formula (IIIa). In one embodiment, the polymer of Formula (III') is also represented by Formula (IIIb). In some embodiments, the functional groups on the surface of the substrate are selected from alkene, alkyne, or optionally substituted phenyl azide. In some embodiments, the polymer coating is covalently bonded to the alkene groups at an elevated temperature. In one embodiment, the alkene groups are acrylamide groups. In one embodiment, the substrate is a bead.

BRIEF DESCRIPTION OF THE DRAWINGS

FIG. 3A shows the Typhoon fluorescence image of the grafted surface hybridized with a complimentary dye-containing oligonucleotide sequence. FIG. 3B shows a chart of median Typhoon intensity of in situ PAZAM.

FIG. 4A shows the Typhoon fluorescence image of the grafted surface hybridized with a complimentary dye-containing oligonucleotide sequence. FIG. 4B shows a chart of median Typhoon intensity of spin coated PAZAM.

FIG. 5A is an enlarged version of the UV-illuminated region of the channels. FIG. 5B and FIG. 5C shows the cluster number and cluster filtered intensity of the channels.

FIGS. 6A-C show clusters on a spin-coated PAZAM surface. FIG. 6A shows a chart of median typhoon intensity of spin coated PAZAM on HiSeq flowcell. FIG. 6B shows the Typhoon fluorescence image of the grafted surface hybridized with a complimentary dye-containing oligonucleotide sequence. FIG. 6C shows enlarged images of clusters on Lanes 3 and 5.

FIGS. 8A-I show clusters and sequencing of the polynucleotides on a flow-coated PAZAM mixture and the data obtained.

FIG. 10A shows a chart of the media Typhoon intensity vs. Photo XL. FIG. 10B shows a chart of the UV time vs. Photo XL of different crosslinking agents.

FIGS. 11A-11B shows a photoactive, patterned surface and polymer locking.

DETAILED DESCRIPTION OF THE PREFERRED EMBODIMENTS

Figure 1A:
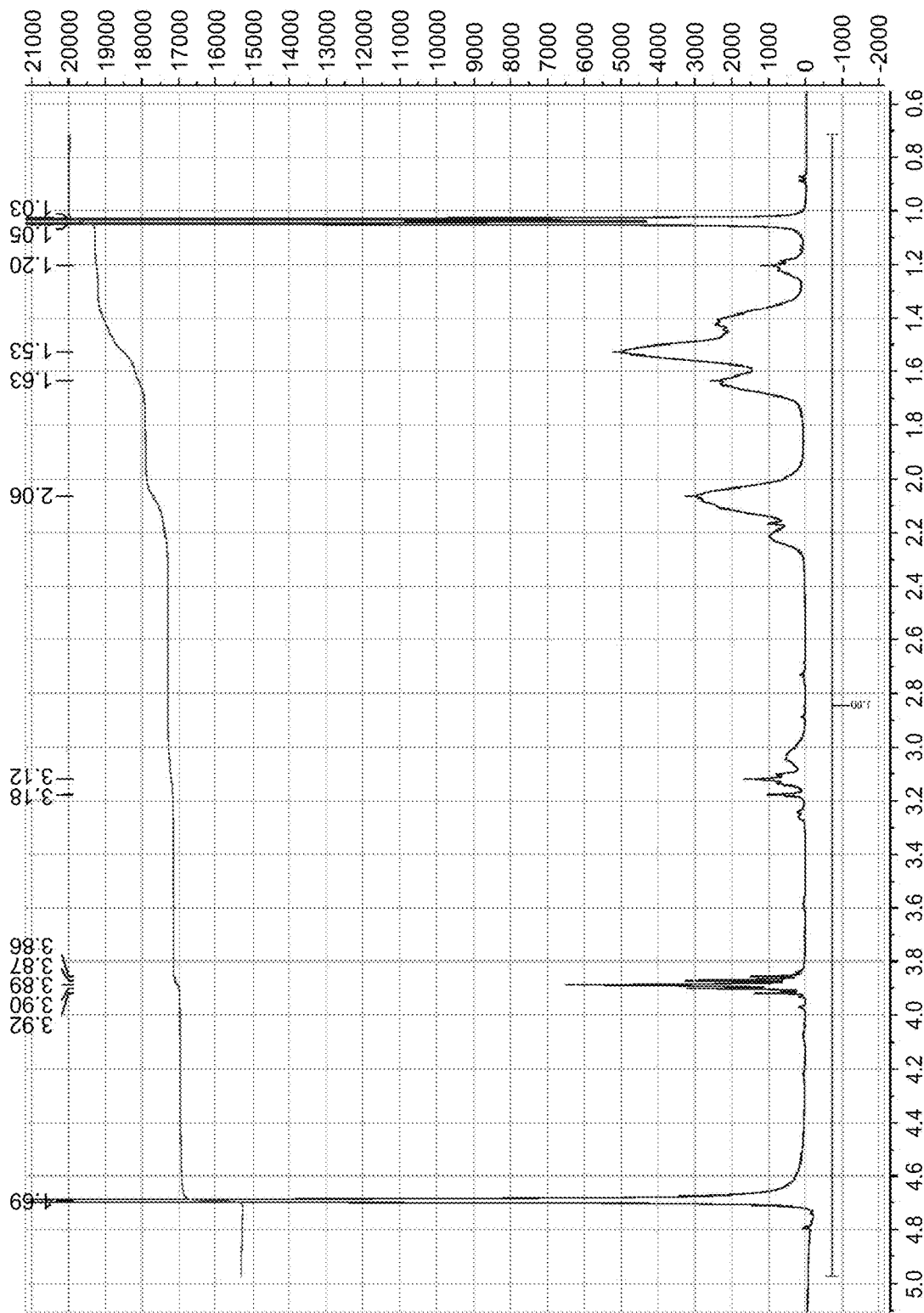
FIG. 1A shows the $^1$H NMR spectrum of poly(N-(5-azidoacetamidylpentyl)acrylamide-co-acrylamide) (PAZAM).

The present disclosure relates to substrates comprising a surface coated with a polymer that is covalently bound to the surface. A preferred embodiment of such substrates includes poly(N-(5-azidoacetamidylpentyl)acrylamide-co-acrylamide) (aka PAZAM or DASFA) coatings. These polymer coatings are covalently attached to a functionalized surface of a substrate, such as a surface of a flow cell or a surface of a molecular array. The present disclosure also relates to methods of preparing such polymer-coated surfaces and methods of using substrates comprising such polymer coated surfaces. In a preferred embodiment, substrates having PAZAM-coated surfaces are used to determine a nucleotide sequence of a polynucleotide.

This new polymer coating and approach generates an air-stable material that overcomes many of the limitations of the currently known polymer coatings.

Definitions

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, common organic abbreviations are defined as follows:

Ac Acetyl
Ac$_2$O Acetic anhydride
APTS aminopropyl silane
APTES (3-aminopropyl)triethoxysilane
APTMS (3-aminopropyl)trimethoxysilane
aq. Aqueous
Azapa N-(5-azidoacetamidylpentyl) acrylamide
APTMS 3-aminopropyl trimethoxysilane
BHT Butylated hydroxyl toluene
Bn Benzyl
Brapa or BRAPA N-(5-bromoacetamidylpentyl) acrylamide
Bz Benzoyl
BOC or Boc tert-Butoxycarbonyl
Bu n-Butyl
cat. Catalytic
Cbz Carbobenzyloxy
CyCl Cyanuric chloride
° C. Temperature in degrees Centigrade
dATP Deoxyadenosine triphosphate
dCTP Deoxycytidine triphosphate
dGTP Deoxyguanosine triphosphate
dTTP Deoxythymidine triphosphate
DBU 1,8-Diazabicyclo[5.4.0]undec-7-ene
DCA Dichloroacetic acid
DCE 1,2-Dichloroethane
DCM Methylene chloride
DIEA Diisopropylethylamine
DMA Dimethylacetamide
DME Dimethoxyethane
DMF N,N'-Dimethylformamide
DMSO Dimethylsulfoxide
DPPA Diphenylphosphoryl azide
Et Ethyl
EtOAc Ethyl acetate
g Gram(s)
GPC Gel permeation chromatography
h or hr Hour(s)
iPr Isopropyl
KPi 10 mM potassium phosphate buffer at pH 7.0
KPS Potassium persulfate
IPA Isopropyl Alcohol
IPHA.HCl N-Isopropylhydroxylamine hydrochloride
LCMS Liquid chromatography-mass spectrometry
LDA Lithium diisopropylamide
m or min Minute(s)
mCPB A meta-Chloroperoxybenzoic Acid
MeOH Methanol
MeCN Acetonitrile
mL Milliliter(s)
MTBE Methyl tertiary-butyl ether
NaN3 Sodium Azide
NHS N-hydroxysuccinimide
PAZAM poly(N-(5-azidoacetamidylpentyl) acrylamide-co-acrylamide) of any acrylamide to Azapa ratio
PG Protecting group
Ph Phenyl
ppt Precipitate
rt Room temperature
SFA Silane Free Acrylamide as defined in U.S. Pat. Pub. No. 2011/0059865
Sulfo-HSAB or SHSAB N-Hydroxysulfosuccinimidyl-4-azidobenzoate
TEA Triethylamine
TEMPO (2,2,6,6-Tetramethylpiperidin-1-yl)oxyl
TCDI 1,1'-Thiocarbonyl diimidazole
Tert, t tertiary
TFA Trifluoroacetic acid
THF Tetrahydrofuran
TEMED Tetramethylethylenediamine
μL Microliter(s)

As used herein, the term "array" refers to a population of different probe molecules that are attached to one or more substrates such that the different probe molecules can be differentiated from each other according to relative location. An array can include different probe molecules that are each located at a different addressable location on a substrate. Alternatively or additionally, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Exemplary formats that can be used in the invention to distinguish beads in a liquid array, for example, using a microfluidic device, such as a fluorescent activated cell sorter (FACS), are described, for example, in U.S. Pat. No. 6,524,793. Further examples of arrays that can be used in the invention include, without limitation, those described in U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

As used herein, the term "polymer locking" refers to the process where the functional groups on the surface of a substrate react with the polymer coating so that the polymer coating is covalently bonded to the surface.

As used herein, any "R" group(s) such as, without limitation, $R^2$, $R^3$, $R^4$, $R^5$, $R^6$, $R^7$, and $R^8$ represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^2$ and $R^3$, or $R^2$, $R^3$, or $R^4$, and the atom to which it is attached, are indicated to be "taken together" or "joined together" it means that they are covalently bonded to one another to form a ring, an example of which is set forth below:

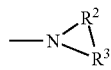

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be individually and independently substituted with one or more group(s) individually and independently selected from a group of functionalities including, but not limited to, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino group, di-substituted amino group, and protected derivatives thereof.

As used herein, "alkyl" refers to a straight or branched hydrocarbon chain that comprises a fully saturated (no double or triple bonds) hydrocarbon group. In some embodiments, the alkyl group may have 1 to 20 carbon atoms (whenever it appears herein, a numerical range such as "1 to 20" refers to each integer in the given range inclusive of the endpoints; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated).

The alkyl group may also be a medium size alkyl having about 7 to about 10 carbon atoms. The alkyl group can also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, and hexyls. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). In some embodiments, cycloalkyl groups can contain 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl, and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "aryl" refers to a carbocyclic (all carbon) monocyclic or multicyclic aromatic ring system (including, e.g., fused, bridged, or spiro ring systems where two carbocyclic rings share a chemical bond, e.g., one or more aryl rings with one or more aryl or non-aryl rings) that has a fully delocalized pi-electron system throughout at least one of the rings. The number of carbon atoms in an aryl group can vary. For example, in some embodiments, the aryl group can be a $C_6$-$C_{14}$ aryl group, a $C_6$-$C_{10}$ aryl group, or a $C_6$ aryl group. Examples of aryl groups include, but are not limited to, benzene, naphthalene, and azulene. An aryl group may be substituted or unsubstituted.

As used herein, "heterocyclyl" refers to ring systems including at least one heteroatom (e.g., O, N, S). Such systems can be unsaturated, can include some unsaturation, or can contain some aromatic portion, or be all aromatic. A heterocyclyl group may be unsubstituted or substituted.

As used herein, "heteroaryl" refers to a monocyclic or multicyclic aromatic ring system (a ring system having a least one ring with a fully delocalized pi-electron system)

that contain(s) one or more heteroatoms, that is, an element other than carbon, including but not limited to, nitrogen, oxygen, and sulfur, and at least one aromatic ring. The number of atoms in the ring(s) of a heteroaryl group can vary. For example, in some embodiments, a heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heteroalicyclic" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, and cyclic carbamates. When composed of two or more rings, the rings may be joined together in a fused fashion. Additionally, any nitrogens in a heteroalicyclic may be quaternized. Heteroalicyclyl or heteroalicyclic groups may be unsubstituted or substituted. Examples of such "heteroalicyclic" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroalkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heteroalicyclyl)alkyl" is a heterocyclic or a heteroalicyclic group connected, as a substituent, via a lower alkylene group. The lower alkylene and heterocyclic or a heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

As used herein, "alkoxy" refers to the formula —OR wherein R is an alkyl, an alkenyl, an alkynyl, a cycloalkyl, a cycloalkenyl or a cycloalkynyl is defined as above. A non-limiting list of alkoxys is methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "alkylamino" refers to an alkyl group in which one or more of the hydrogen atoms are replaced by an amino group. Exemplary alkylamino groups include but are not limited to aminomethyl, 2-aminoethyl, 3-aminoethyl. An alkylamino may be substituted or unsubstituted.

As used herein, "alkylamido" refers to an alkyl group in which one or more of the hydrogen atoms are replaced by a C-amido group or an N-amido group. An alkylamido may be substituted or unsubstituted.

As used herein, "alkylthio" refers to RS—, in which R is an alkyl. Alkylthio can be substituted or unsubstituted.

As used herein, a "C-amido" group refers to a "—C(=O)N($R_a R_b$)" group in which $R_a$ and $R_b$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A C-amido may be substituted or unsubstituted.

As used herein, an "N-amido" group refers to a "RC(=O)N($R_a$)—" group in which R and $R_a$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-amido may be substituted or unsubstituted.

The term "halogen atom", "halogen" or "halo" as used herein, means any one of the radio-stable atoms of column 7 of the Periodic Table of the Elements, such as, fluorine, chlorine, bromine, and iodine.

The term "amine" as used herein refers to a —$NH_2$ group wherein one or more hydrogen can be optionally substituted by a R group. R can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

The term "aldehyde" as used herein refers to a —$R_c$—C(O)H group, wherein $R_c$ can be absent or independently selected from alkylene, alkenylene, alkynylene, cycloalkylene, cycloalkenylene, cycloalkynylene, arylene, heteroarylene, heteroalicyclylene, aralkylene, or (heteroalicyclyl)alkylene.

The term "activated ester" as used herein refers to an ester which spontaneously reacts with a nucleophile, for example NHS ester, pentafluorophenyl ester, or nitrophenyl ester.

The term "nitrene" as used herein refers the nitrogen analogue of a carbene, wherein the nitrogen atom is uncharged with six valence electrons.

The term "amino" as used herein refers to a —NH$_2$ group.

The term "hydroxy" as used herein refers to a —OH group.

The term "cyano" group as used herein refers to a "—CN" group.

The term "azido" as used herein refers to a —N$_3$ group.

The term "thiol" as used herein refers to a —SH group.

The term "hydrazinyl" as used herein refers to a —NHNH$_2$ group.

The term "hydrazonyl" as used herein refers to a

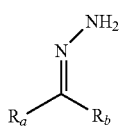

group.

The term "formyl" as used herein refers to a —C(O)H group.

The term "glycidyl" or "glycidyl ether" as used herein refers to

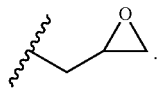

The term "epoxy" as used herein refers to

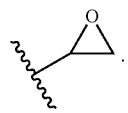

The term "carboxylic acid" as used herein refers to —C(O)OH.

The term "thiocyanate" as used herein refers to —S—C≡N group.

The term "oxo-amine" as used herein refers to —O—NH$_2$ group, wherein one or more hydrogen of the —NH$_2$ can be optionally substituted by a R group. R can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

As used herein, the prefixes "photo" or "photo-" mean relating to light or electromagnetic radiation. The term can encompass all or part of the electromagnetic spectrum including, but not limited to, one or more of the ranges commonly known as the radio, microwave, infrared, visible, ultraviolet, X-ray or gamma ray parts of the spectrum. The part of the spectrum can be one that is blocked by a metal region of a surface such as those metals set forth herein. Alternatively or additionally, the part of the spectrum can be one that passes through an interstitial region of a surface such as a region made of glass, plastic, silica, or other material set forth herein. In particular embodiments, radiation can be used that is capable of passing through a metal. Alternatively or additionally, radiation can be used that is masked by glass, plastic, silica, or other material set forth herein.

As used herein, the term "reactive site" means a site on the polymer coatings described herein that can be used to attach one or more molecules by way of a chemical reaction or molecular interaction. Such attachment may be via a covalent bond or through other bonding or interactive forces.

As used herein, the term "percent surface remaining" can refer to the intensity measured using a TET qc to stain the P5/P7 surface primers. The P5 and P7 primers are used on the surface of commercial flow cells sold by Illumina Inc. for sequencing on the HiSeq, MiSeq and Genome Analyzer platforms. The primer sequences are described in US Pat. Pub. No. 2011/0059865 A1, which is incorporated herein by reference. TET is a dye labeled oligonucleotide having complimentary sequence to the P5/P7 primer. TET can be hybridized to the P5/P7 primer on a surface; the excess TET can be washed away, and the attached dye concentration can be measured by fluorescence detection using a scanning instruments such as a Typhoon Scanner (General Electric).

Substrate Compositions Having a Polymer-Coated Surface

A first aspect of the compositions described herein relates to a substrate comprising a surface having a polymer coating covalently attached thereto. In a preferred embodiment, the polymer comprises PAZAM. In some embodiments, the polymer coating comprises a recurring unit of Formula (I) and a recurring unit of Formula (II):

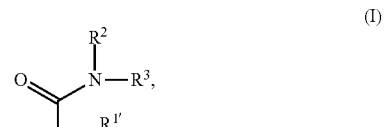

wherein: each $R^1$ and $R^{1'}$ is independently selected from hydrogen, halo, alkyl, alkoxy, alkenyl, alkynyl, cycloalkyl, aryl, heteroaryl, heterocyclyl, or optionally substituted variants thereof;

each $R^2$ and $R^3$ is independently selected from hydrogen, alkyl, alkylamino, alkylamido, alkylthiol, aryl, or optionally substituted variants thereof; each $R^4$, $R^{4'}$, $R^5$ and $R^{5'}$ is independently selected from H, $R^6$, $OR^6$, —C(O)$OR^6$, —C(O)$R^6$, —OC(O)$R^6$, —C(O)$NR^7R^8$, or —$NR^7R^8$;

$R^6$ is independently selected from H, OH, alkyl, cycloalkyl, hydroxyalkyl, aryl, heteroaryl, heterocyclyl, or optionally substituted variants thereof;

each $R^7$ and $R^8$ is independently selected from H or alkyl, or $R^7$ and $R^8$ are joined together with the atom or atoms to which they are attached to form a heterocycle.

In some embodiments of such compositions, $R^2$ is H and $R^3$ is an optionally substituted alkyl.

In still further embodiments of such compositions, $R^3$ is an alkyl substituted by an N-amido group.

In some embodiments of the compositions described herein, the recurring unit of Formula (I) is also represented by Formula (Ia):

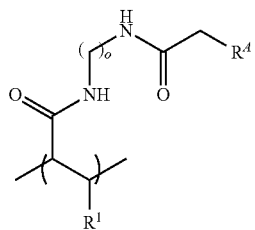

(Ia)

wherein $R^1$ is H or alkyl; $R^A$ is selected from the group consisting of hydrogen, amine, optionally substituted alkene, optionally substituted alkyne, oxo-amine, azido, formyl, halo, hydroxy, hydrazinyl, hydrazonyl, cyanuric chloride, thiocyanate, carboxylic acid, glycidyl, activated ester, epoxy, aziridine, triazoline, and thiol; each of the —(CH$_2$)—$_o$ can be optionally substituted; o is an integer between 1-50; and provided that when $R^1$ is H and $R^A$ is halo, $R^A$ cannot be bromo group.

In some such embodiments, o is 5 and $R^A$ is azido.

In further embodiments, $R^1$ is hydrogen.

In still further embodiments, $R^4$ is —C(O)NR$^7$R$^8$, wherein each $R^7$ and $R^8$ is independently selected from hydrogen, alkyl or hydroxyalkyl.

In some embodiments of such polymer compositions, $R^4$ is —C(O)NH$_2$, —C(O)NHCH$_3$ or —C(O)N(CH$_3$)$_2$.

In other embodiments, $R^4$ is —C(O)NH(CH$_2$)$_2$OH or —C(O)N(CH$_3$)(CH$_2$)$_2$OH.

In still other embodiments, $R^4$ is NR$^7$R$^8$, wherein $R^7$ and $R^8$ are joined together with the atoms to which they are attached to form a five membered heterocycle.

In proffered embodiments comprising a five membered heterocycle, the five membered heterocycle is an optionally substituted pyrrolidine.

In yet other embodiments, $R^4$ is —C(O)OR$^6$, wherein $R^6$ is selected from hydrogen, alkyl or hydroxyalkyl.

In one preferred embodiment, $R^6$ is hydrogen.

In another preferred embodiment, $R^6$ is methyl.

In yet another preferred embodiment, $R^6$ is hydroxyethyl.

In other preferred embodiments, $R^{4'}$ is hydrogen.

In still other preferred embodiments, $R^{4'}$ is alkyl.

In yet other preferred embodiments, $R^{4'}$ is methyl.

In some preferred embodiments, $R^{5'}$ is hydrogen.

In additional preferred embodiments, $R^{5'}$ is alkyl.

In further preferred embodiments, $R^{5'}$ is methyl.

In yet another embodiment of the substrates comprising a polymer-coated surface described herein, the polymer coating comprises a polymer of Formula (III) or (III'):

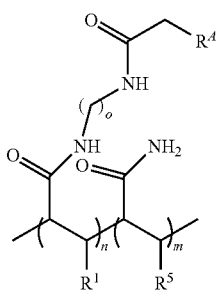

(III)

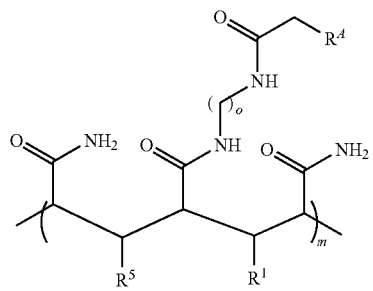

(III')

wherein $R^1$ is selected from H or alkyl; $R^A$ is selected from the group consisting of hydrogen, amine, optionally substituted alkene, optionally substituted alkyne, oxo-amine, azido, formyl, halo, hydroxy, hydrazinyl, hydrazonyl, cyanuric chloride, thiocyanate, carboxylic acid, glycidyl, activated ester, epoxy, aziridine, triazoline, and thiol; each of the —(CH$_2$)—$_o$ can be optionally substituted; o is an integer in the range of 1-50; $R^5$ is selected from H or alkyl; n is an integer in the range of 1 to 50,000; and n is an integer in the range of 1 to 50,000; provided that when $R^1$ and $R^5$ are H, o is 5, then $R^A$ cannot be a bromo group. In some embodiments, o is 5.

In one embodiment, the polymer of Formula (III) or (III') is also represented by Formula (IIIa) or (IIIb):

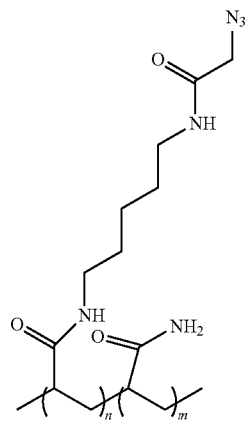

(IIIa)

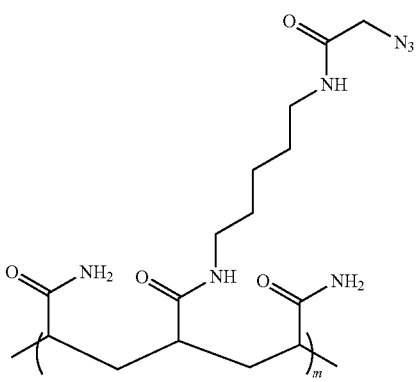

(IIIb)

wherein n is an integer in the range of 1-20,000, and m is an integer in the range of 1-100,000.

In some such embodiments, the polymer coating is covalently bonded to a series of functional groups attached to the surface, wherein the functional groups are selected from alkene, alkyne, nitrene, aldehyde, hydrazine, activated ester, glycidyl ether, amine, maleimide or benzoyl ester with a phosphine substituent in the ortho position.

In one preferred embodiment of such compositions, the functional groups comprise alkynes, and the recurring unit of Formula (I) is also represented by Formula (Ia), wherein $R^4$ is azido.

In another preferred embodiment of such compositions, the functional groups comprise nitrenes, and the recurring unit of Formula (I) is also represented by Formula (Ia), wherein $R^4$ is azido.

In yet another preferred embodiment of such compositions, the functional groups comprise activated esters, and the recurring unit of Formula (I) is also represented by Formula (Ia), wherein $R^4$ is amine.

In still another preferred embodiment of such compositions, the functional groups comprise hydrazines, and the recurring unit of Formula (I) is also represented by Formula (Ia), wherein $R^4$ is formyl.

In yet another preferred embodiment of such compositions, the functional groups comprise aldehyde group, and the recurring unit of Formula (I) is also represented by Formula (Ia), wherein $R^4$ is amine, oxo-amine, or hydrozinyl.

In still another preferred embodiment of such compositions, the functional groups comprise glycidyl ether, and the recurring unit of Formula (I) is also represented by Formula (Ia), wherein $R^4$ is amine.

In yet another preferred embodiment of such compositions, the functional groups comprise amine, and the recurring unit of Formula (I) is also represented by Formula (Ia), wherein $R^4$ is azido.

In yet another preferred embodiment of such compositions, the functional groups comprise maleimide, the recurring unit of Formula (I) is also represented by Formula (Ia) and wherein $R^4$ is thiol.

In yet another embodiment of the substrates comprising a polymer-coated surface described herein, the recurring unit of Formula (I) is also represented by Formula (Ib):

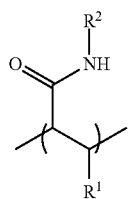

(Ib)

wherein $R^2$ is optionally substituted aryl.

In some such embodiments, $R^2$ in Formula (Ib) is phenyl azide, optionally substituted with one or more halogen. In one particular embodiment, $R^2$ is perfluoro phenyl azide.

In some embodiments, $R^1$ in Formula (Ib) is hydrogen.

In further embodiments, $R^4$ in Formula (Ib) is —C(O)NR$^7$R$^8$. In one particular embodiment, $R^4$ is —C(O)NH$_2$.

In some embodiments, $R^{4'}$ in Formula (Ib) is hydrogen.

In some embodiments, $R^5$ in Formula (Ib) is alkyl.

In other embodiments, $R^5$ in Formula (Ib) is hydrogen.

In some embodiments, $R^{5'}$ in Formula (Ib) is hydrogen.

In another embodiment of the substrates comprising a polymer-coated surface described herein, the polymer coating comprises a polymer of Formula (IV):

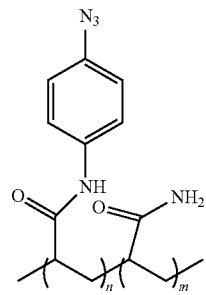

(IV)

wherein n is an integer in the range of 1-50,000, and m is an integer in the range of 1-100,000. In a particular embodiment, the phenyl group of Formula (IV) is optionally substituted by one or more fluoro groups.

The polymer coating described herein can be covalently attached to a variety of substrates. Essentially any substrate material that can be functionalized with reactive groups including, but not limited to, alkene, alkyne, nitrene, aldehyde, hydrazine, activated ester, glycidyl ether, amine, maleimide can be utilized. Acrylamide, enone, or acrylate may also be utilized as a substrate material. Substrates can comprise a single material or a plurality of different materials. Substrates can be composites or laminates. In some embodiments, the substrate has at least one surface comprising glass. In other embodiments, the substrate has at least one surface comprising a metal. In some such embodiments, the metal is gold. In some embodiments, the substrate has at least one surface comprising a metal oxide. In one embodiment, the surface comprises a tantalum oxide. Other substrate materials can include, but are not limited to, plastic, silicon, silicon dioxide, silicon nitride, fused silica, gallium arsenide, indium phosphide, aluminum, ceramics, polyimide, quartz, resins, polymers and copolymers. Substrate can be flat, round, or textured.

In some embodiments of the compositions described herein, the surface of the substrate comprises both polymer-coated regions and inert regions that are not coated with polymer. The polymer-coated regions can comprise reactive sites, and thus, can be used to attach molecules through chemical bonding or other molecular interactions. In some embodiments, the polymer-coated regions and the inert regions can alternate so as to form a pattern or a grid. Such patterns can be in one or two dimensions. In some embodiments, the inert regions can be selected from the group consisting of glass regions, metal regions, mask regions and interstitial regions. In one preferred embodiment, the surface comprises glass regions. In another preferred embodiment, the surface comprises metal regions. In still another preferred embodiment, the surface comprises mask regions. In yet another preferred embodiment, the surface comprises interstitial regions. In some embodiments of the compositions described herein, the substrate can be a bead. In a preferred embodiment, the surface of the bead is functionalized. The functionalization can occur before or after introducing the bead into a well. In one embodiment, the well is pre-defined in a flow cell surface. Exemplary substrate materials that can be coated with a polymer of the present disclosure or that can otherwise be used in a composition or method set forth herein are described in U.S. Ser. Nos. 13/492,661 and 13/661,524, each of which is incorporated herein by reference.

A second aspect of the compositions described herein relates to a flow cell comprising one or more substrates comprising a surface having a polymer coating covalently attached thereto. In some embodiments, the flow cells described herein comprise one or more of the substrates described above. In a preferred embodiment, the polymer comprises PAZAM.

In some embodiments, the flow cells further comprise polynucleotides attached to the surface of the substrate via the polymer coating. In preferred embodiments, the polynucleotides are present in the flow cells in polynucleotide clusters, wherein the polynucleotides of the polynucleotide clusters are attached to a surface of the flow cell via the polymer coating. In such embodiments, the surface of the flow cell body to which the polynucleotides are attached is considered the substrate. In other embodiments, a separate substrate having a polymer coated surface is inserted into the body of the flow cell. In preferred embodiments, the flow cell is a flow chamber that is divided into a plurality of lanes or a plurality of sectors, wherein one or more of the plurality of lanes or plurality of sectors comprises a surface that is coated with a covalently attached polymer coating described herein. In some embodiments of the flow cells described herein, the attached polynucleotides within a single polynucleotide cluster have the same or similar nucleotide sequence. In some embodiments of the flow cells described herein, the attached polynucleotides of different polynucleotide clusters have different or nonsimilar nucleotide sequences. Exemplary flow cells and substrates for manufacture of flow cells that can be used in method or composition set forth herein include, but are not limited to, those commercially available from Illumina, Inc. (San Diego, Calif.) or described in US 2010/0111768 A1 or US 2012/0270305, each of which is incorporated herein by reference.

Methods of Coating Substrates with Covalently Attached Polymers

A first aspect of the present methods disclosed herein relates to a process for preparing a polymer coating immobilized to a surface of a substrate. In some embodiments, the method comprises contacting a polymer with a surface of a substrate, wherein the surface comprises a plurality of functional groups, thereby forming a layer of polymer coating over the surface, and wherein the polymer coating is covalently bonded to the functional groups on the surface. In some embodiments, the polymer is formed in situ on the surface of the substrate by polymerizing a polymerizable material on the surface of the substrate. In some other embodiment, the polymer is pre-formed before contacting with the surface of the substrate. In a preferred embodiment, the polymer comprises PAZAM.

In some embodiments of the methods of immobilizing a polymer coating to a substrate surface, the polymer coating comprises a recurring unit of Formula (I) and a recurring unit of Formula (II):

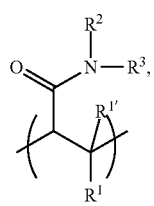
(I)

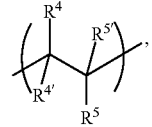
(II)

wherein: each $R^1$ and $R^{1'}$ is independently selected from hydrogen, halo, alkyl, alkoxy, alkenyl, alkynyl, cycloalkyl, aryl, heteroaryl, heterocyclyl, or optionally substituted variants thereof;

each $R^2$ and $R^3$ is independently selected from hydrogen, alkyl, alkylamino, alkylamido, alkylthiol, aryl, or optionally substituted variants thereof; each $R^4$, $R^{4'}$, $R^5$ and $R^{5'}$ is independently selected from H, $R^6$, $OR^6$, $-C(O)OR^6$, $-C(O)R^6$, $-OC(O)R^6$, $-C(O)NR^7R^8$, or $-NR^7R^8$;

$R^6$ is independently selected from H, OH, alkyl, cycloalkyl, hydroxyalkyl, aryl, heteroaryl, heterocyclyl, or optionally substituted variants thereof;

each $R^7$ and $R^8$ is independently selected from H or alkyl, or $R^7$ and $R^8$ are joined together with the atom or atoms to which they are attached to form a heterocycle.

In some embodiment, $R^2$ is H and $R^3$ is an optionally substituted alkyl. In one embodiment, $R^3$ an alkyl substituted by an N-amido group.

In other embodiments of the methods of coating a substrate surface with a polymer, the recurring unit of Formula (I) is also represented by Formula (Ia):

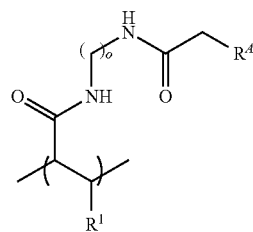
(Ia)

wherein $R^1$ is H or alkyl; $R^4$ is selected from the group consisting of hydrogen, amine, optionally substituted alkene, optionally substituted alkyne, oxo-amine, azido, formyl, halo, hydroxy, hydrazinyl, hydrazonyl, cyanuric chloride, thiocyanate, carboxylic acid, glycidyl, activated ester, aziridine, triazoline, epoxy, and thiol; each of the $-(CH_2)-_o$ can be optionally substituted; o is an integer between 1-50; provided that when $R^1$ is H and $R^4$ is halo, $R^4$ cannot be a bromo group.

In one embodiment of such method, o is 5 and $R^4$ is azido.

In another embodiment of such method, $R^1$ is hydrogen.

In still another embodiment of such method, $R^4$ is $-C(O)NR^7R^8$, wherein each $R^7$ and $R^8$ is independently selected from hydrogen, alkyl or hydroxyalkyl. In a particular embodiment of such method, $R^4$ is $-C(O)NH_2$.

In another embodiment of such method, $R^{4'}$ is hydrogen.

In a further embodiment of such method, both $R^{4'}$ and $R^{5'}$ are hydrogen.

In yet another embodiment of such method, at least one of $R^{4'}$ and $R^{5'}$ is alkyl, for example a methyl group.

In some embodiment, the polymer coating comprises a polymer of Formula (III) or (III'):

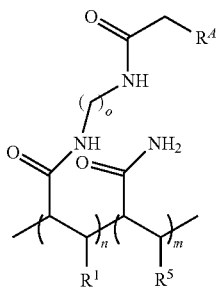

(III)

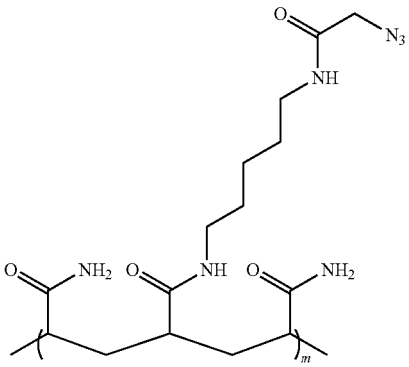

(IIIb)

wherein n is an integer in the range of 1-20,000, and m is an integer in the range of 1-100,000.

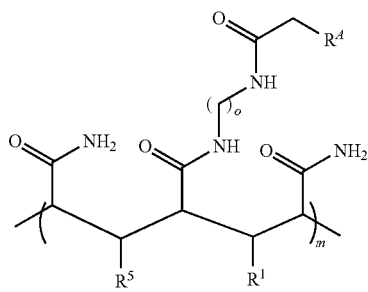

(III')

wherein $R^1$ is selected from H or alkyl; $R^A$ is selected from the group consisting of hydrogen, amine, optionally substituted alkene, optionally substituted alkyne, oxo-amine, azido, formyl, halo, hydroxy, hydrazinyl, hydrazonyl, cyanuric chloride, thiocyanate, carboxylic acid, glycidyl, activated ester, aziridine, triazoline, epoxy, and thiol; each of the —(CH$_2$)—$_o$ can be optionally substituted; o is an integer in the range of 1-50; $R^5$ is selected from H or alkyl; n is an integer in the range of 1 to 50,000; and n is an integer in the range of 1 to 50,000; provided that when $R^1$ and $R^5$ are H, o is 5, then $R^A$ cannot be a bromo group. In some embodiments, o is 5.

In one embodiment, the polymer of Formula (III) or (III') is also represented by Formula (IIIa) or (IIIb):

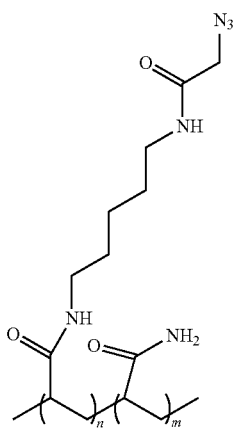

(IIIa)

In some embodiments of such methods, the functional groups on the surface of the substrate comprise photo-activatable azides. In some embodiments, the photo-activatable azides are optionally substituted phenyl azide groups. In some of these embodiments, the phenyl azide is prepared by reacting an amine group on the surface of the substrate with N-hydroxysulfosuccinimidyl-4-azidobenzoate (sulfo-HSAB).

In some embodiments of the above-described methods, the phenyl azide is photo-activated prior to contacting the polymer with surface of the substrate. In a preferred embodiment of such methods, the photo-activated functional groups generate nitrene. In another preferred embodiment of such methods, the polymer coating is covalently bonded to nitrene groups via photo-activation.

In some embodiments of the above-described methods of covalently attaching a polymer coating to the surface of a substrate, the functional groups on the surface of the substrate comprise alkyne groups.

In some embodiments of the above-described methods of covalently attaching a polymer coating to the surface of a substrate, the polymer coating is covalently bonded to the functional groups in the presence of a catalyst. In a particular embodiment, the catalyst is a copper catalyst. In some embodiments, the polymer coating is covalently bonded to the alkyne groups without using a copper catalyst.

In some embodiments of the above-described methods of covalently attaching a polymer coating to the surface of a substrate, the functional groups on the surface of the substrate comprise alkene groups. In some embodiments, the alkene groups are prepared by reacting amine functionalized surface with acryloyl groups. In some preferred embodiments, the amine functionalized surface prepared by treating the surface with 3-aminopropyl trimethoxysilane (APTMS). In some further preferred embodiments, the acryloyl group can be selected from an activated acrylic ester, acrylic acid, acrylic chloride or COMU (CAS Number 1075198-30-9). In one embodiment, the activated acrylic ester is an acrylic acid N-hydroxysuccinimide (NHS) ester. In some other embodiments, the alkene groups are prepared by directly contacting the surface of the substrate with functionalized silanes. In some further embodiments, the functionalized silane can be selected from 3-acrylamidotrimethoxysilane or methacryloxypropyltrimethoxysilane.

In some embodiments of the above-described methods of covalently attaching a polymer coating to the surface of a substrate, the polymer coating is covalently bonded to the functional groups at an elevated temperature. In a preferred embodiment, the elevated temperature is any temperature in a range of 60° C. to 90° C.

In other embodiments of the methods of immobilizing a polymer coating to a substrate surface, the recurring unit of Formula (I) is also represented by Formula (Ib):

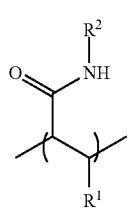

wherein $R^2$ is optionally substituted aryl.

In one embodiment of such methods, $R^2$ in Formula (Ib) is phenyl azide, optionally substituted with one or more halogen. In one particular embodiment, $R^2$ is perfluoro phenyl azide.

In another embodiment of the methods of coating a substrate surface with a polymer, $R^1$ in Formula (Ib) is hydrogen.

In some embodiments of such methods, $R^4$ in Formula (Ib) is —C(O)NR$^7$R$^8$. In one particular embodiment, $R^4$ is —C(O)NH$_2$.

In other embodiments of such methods, $R^5$ in Formula (Ib) is hydrogen.

In still other embodiments of such methods, both $R^{4'}$ and $R^{5'}$ in Formula (Ib) are hydrogen.

In some embodiments of such methods, the polymerizable material is applied in liquid form.

In some embodiments of the methods of immobilizing a polymer coating to a substrate surface the plurality of functional groups are arranged on the surface of the substrate so as to form a plurality of polymer-coated regions and a plurality of inert regions subsequent to the polymerization of the polymeric material. In some embodiments the inert regions are selected from the group consisting of glass regions, metal regions, mask regions and interstitial regions. In a preferred embodiment, the inert regions comprise glass. In some embodiments, the plurality of polymer-coated regions and the plurality of inert regions are arranged on the surface so as to form a pattern or a grid. Such patterns or grids can be one dimensional or two dimensional with respect to the surface of the substrate. Exemplary patterned surfaces that can be employed are described in U.S. Ser. Nos. 13/492,661 and 13/661,524, each of which is incorporated herein by reference.

In some embodiments of the above-described methods of preparing a polymer coating immobilized to a surface of a substrate, the polymer coating is dissolved in an aqueous solution before covalently bonding to the functional groups of the surface. In some embodiment, the substrate is a bead.

A second aspect of the present methods disclosed herein relates to a process for preparing an array of polynucleotides. In such embodiments, the methods can comprise the steps of (a) reacting a plurality of first oligonucleotides and a plurality of second oligonucleotides with reactive sites on a polymer coating present on a surface of any one of the substrates described herein or a polymer coating prepared by any one of the methods of immobilizing a polymer coating to a surface of a substrate as described herein; (b) contacting the plurality of first oligonucleotides attached to the polymer coating with templates to be amplified; and (c) amplifying the templates using the first oligonucleotides and the second oligonucleotides, thereby generating a clustered array of polynucleotides. In some embodiments, each template comprises at the 3' end a sequence capable of hybridizing to the first oligonucleotides and at the 5' end a sequence the complement of which is capable of hybridizing to the second oligonucleotides. In the above methods, the second oligonucleotide is optional. Thus, the second oligonucleotide need not be present in some embodiments. If present, the second oligonucleotide can be attached to the polymer coating or it can be provided in solution during the amplification step.

In some embodiments of the above-described methods of preparing an array of polynucleotides, the first oligonucleotides or the second oligonucleotides comprise alkyne groups to be reacted with the azido groups of the polymer coating. In a preferred embodiment, both the first oligonucleotides and the second oligonucleotides comprise such groups.

In other embodiments of the above-described methods of preparing an array of polynucleotides, the first oligonucleotides or the second oligonucleotides comprise amine groups to be reacted with cyanuric chloride of the polymer coating. In a preferred embodiment, both the first oligonucleotides and the second oligonucleotides comprise such groups.

In still other embodiments of the above-described methods of preparing an array of polynucleotides, the first oligonucleotides or the second oligonucleotides comprise aldehyde groups to be reacted with activated amine groups, such as hydrazinyl or hydrazonyl groups of the polymer coating. In a preferred embodiment, both the first oligonucleotides and the second oligonucleotides comprise such groups.

In yet other embodiments of the above-described methods of preparing an array of polynucleotides, the first oligonucleotides or the second oligonucleotides comprise amine groups to be reacted with thiocyanate or carboxylic acid groups of the polymer coating. In a preferred embodiment, both the first oligonucleotides and the second oligonucleotides comprise such groups.

In additional embodiments of the above-described methods of preparing an array of polynucleotides, the first oligonucleotides or the second oligonucleotides comprise amine groups to be reacted with glycidyl groups of the polymer coating. In a preferred embodiment, both the first oligonucleotides and the second oligonucleotides comprise such groups.

In further embodiments of the above-described methods of preparing an array of polynucleotides, the first oligonucleotides or the second oligonucleotides comprise amine groups to be reacted with amine groups of the polymer coating via a di-aldehyde linker. In a preferred embodiment, both the first oligonucleotides and the second oligonucleotides comprise such groups.

In still other embodiments of the above-described methods of preparing an array of polynucleotides, the first oligonucleotides or the second oligonucleotides comprise amine groups to be reacted with activated ester or epoxy groups of the polymer coating. In a preferred embodiment, both the first oligonucleotides and the second oligonucleotides comprise such groups.

In still other embodiments of the above-described methods of preparing an array of polynucleotides, the first oligonucleotides or the second oligonucleotides comprise aldehyde groups to be reacted with the oxo-amine groups of the polymer coating. In a preferred embodiment, both the first oligonucleotides and the second oligonucleotides comprise such groups.

In a preffered embodiment of the above-described methods of preparing an array of polynucleotides, the polymer coating on the surface of the substrate comprises a polymer of Formula (IIIa) or (IIIb).

A third aspect of the present methods disclosed herein relates to a method for preparing a surface of a substrate comprising: forming a plurality of functional groups on the surface of one or more beads; contacting a polymer coating described herein with the beads to form a polymer coating layer on the surface of the beads, wherein the polymer coating is covalently bonded to the functional groups on the surface of the beads; and affixing the polymer coated beads to the surface of the substrate. In one embodiment, the substrate is a flow cell. In one embodiment, the polymer coating comprises PAZAM. The polymer coating layer can cover the beads either entirely or partially. In one embodiment, the polymer coating layer on the surface of the beads has a thickness of about 20 nm. In some embodiment, the beads have a diameter of about 1.2 micron or less. In some other embodiments, the beads have a diameter of about 0.5 micron or less. In a preferred embodiment, the surface of the substrate is patterned. However, larger beads can be used including. But not limited to, those having a diameter of about 10 micron or less, 5 micron or less, 3 micron or less, or 2 micron or less.

In some embodiments of the methods of preparing a surface of a substrate as described herein, the functional groups on the surface of the beads comprise alkenes. In some embodiments, the alkene groups are prepared by reacting amine functionalized surface of the beads with acryloyl groups. In some preferred embodiments, the amine functionalized surface prepared by treating the surface with 3-aminopropyl trimethoxysilane (APTMS). In some further preferred embodiments, the acryloyl group can be selected from an activated acrylic ester, or an acrylic chloride. In one embodiment, the activated acrylic ester is an acrylic acid N-hydroxysuccinimide (NHS) ester. Other useful coupling agents include acrylic acid, COMU (CAS Number 1075198-30-9), 1-Ethyl-3-(3-dimethylaminopropyl)carbodiimide (EDC) or N-hydroxysuccinimide (NHS). In some other embodiments, the alkene groups are prepared by directly contacting the surface of the substrate with functionalized silanes. In some further embodiments, the functionalized silane can be selected from 3-acrylamidotrimethoxysilane or methacryloxypropyltrimethoxysilane. In some embodiments, the pretreated beads are exposed to a solution comprising a polymerization inhibitor before contacting with the polymer coating. In some embodiment, the polymerization inhibitor is selected from butylated hydroxyl toluene (BHT), diethylhydroxylamine, or (2,2,6,6-Tetramethylpiperidin-1-yl)oxyl (TEMPO). In some preferred embodiments, the polymer coating is covalently bonded to the alkene groups on the surface of the beads at an elevated temperature. In a preferred embodiment, the elevated temperature is any temperature in a range of 60° C. to 90° C.

In some embodiments of the methods of preparing a surface of a substrate as described herein, the functional groups on the surface of the beads comprise photo-activatable azides. In some embodiments, the photo-activatable azides are optionally substituted phenyl azide groups. In some of these embodiments, the phenyl azide is prepared by reacting an amine group on the surface of the substrate with N-hydroxysulfosuccinimidyl-4-azidobenzoate (sulfo-HSAB). In some embodiments, the phenyl azide is photo-activated prior to contacting the polymer with surface of the substrate. In a preferred embodiment of such methods, the photo-activated functional groups generate nitrene. In another preferred embodiment of such methods, the polymer coating is covalently bonded to the functional groups via photo-activation.

In some embodiments of the methods of preparing a surface of a substrate as described herein, the functional groups on the surface of the beads comprise alkyne groups. In some embodiments, the polymer coating is covalently bonded to the functional groups in the presence of a catalyst. In a particular embodiment, the catalyst is a copper catalyst. In some embodiments, the polymer coating is covalently bonded to the alkyne groups without using a copper catalyst.

In some embodiments of the methods of preparing a surface of a substrate as described herein, the polymer coated beads are affixed to the surface of the substrate by loading said beads into the open wells on the surface of the substrate. The beads and the wells can have dimensions that result in no more than one bead residing in each well. Alternatively, the relative dimensions can result in multiple beads per well. In some preferred embodiments, the polymer coated beads are affixed to the surface of the substrate by reacting functional groups of the polymer coating with functional groups on the surface of the substrate. The functional groups of the surface can be located at particular features of a surface, for example, wells or pads. Alternatively, the functional groups of the substrate can be spread across a planar surface. Exemplary methods for preparing such surfaces, that can be coated using the methods and compositions set forth herein, are described in U.S. Ser. Nos. 13/492,661 and 13/661,524, each of which is incorporated herein by reference. In one embodiment, the functional groups of polymer coating comprise amines and the functional groups on the surface of the substrate comprise N-hydroxysuccinimide (NHS) esters. In another embodiment, the functional groups of polymer coating comprise azides and the functional groups on the surface of the substrate comprise alkynes. In yet another embodiment, the functional groups of polymer coating comprise thiols and the functional groups on the surface of the substrate comprise maleimides.

In some embodiments of the methods of preparing a surface of a substrate as described herein, the method further comprises washing the polymer coated beads to remove excess unbounded polymer coating before loading the beads to the surface of the substrate. In some embodiments, the polymer coating is dissolved in a solution before contacting with the beads. In one embodiment, the solution is an aqueous solution.

In some embodiments of the methods of preparing a surface of a substrate as described herein, the method further comprises reacting a plurality of first oligonucleotides and a plurality of second oligonucleotides with reactive sites on the polymer coating of the beads; contacting the plurality of first oligonucleotides attached to the polymer coating with templates to be amplified, each template comprising at the 3' end a sequence capable of hybridizing to the first oligonucleotides and at the 5' end a sequence the complement of which is capable of hybridizing to the second oligonucleotides; and amplifying the templates using the first oligonucleotides and the second oligonucleotides, thereby generating a clustered array of polynucleotides.

In some embodiments of the above-described methods, the first oligonucleotides or the second oligonucleotides comprise alkyne groups to be reacted with the azido groups of the polymer coating. In a preferred embodiment, both the first oligonucleotides and the second oligonucleotides comprise such groups.

In other embodiments of the above-described methods, the first oligonucleotides or the second oligonucleotides comprise amine groups to be reacted with cyanuric chloride of the polymer coating. In a preferred embodiment, both the first oligonucleotides and the second oligonucleotides comprise such groups.

In still other embodiments of the above-described methods, the first oligonucleotides or the second oligonucleotides comprise aldehyde groups to be reacted with activated amine groups, such as hydrazinyl or hydrazonyl groups of the polymer coating. In a preferred embodiment, both the first oligonucleotides and the second oligonucleotides comprise such groups.

In yet other embodiments of the above-described methods, the first oligonucleotides or the second oligonucleotides comprise amine groups to be reacted with thiocyanate or carboxylic acid groups of the polymer coating. In a preferred embodiment, both the first oligonucleotides and the second oligonucleotides comprise such groups.

In additional embodiments of the above-described methods, the first oligonucleotides or the second oligonucleotides comprise amine groups to be reacted with glycidyl groups of the polymer coating. In a preferred embodiment, both the first oligonucleotides and the second oligonucleotides comprise such groups.

In further embodiments of the above-described methods, the first oligonucleotides or the second oligonucleotides comprise amine groups to be reacted with amine groups of the polymer coating via a di-aldehyde linker. In a preferred embodiment, both the first oligonucleotides and the second oligonucleotides comprise such groups.

In still other embodiments of the above-described methods, the first oligonucleotides or the second oligonucleotides comprise amine groups to be reacted with activated ester or epoxy groups of the polymer coating. In a preferred embodiment, both the first oligonucleotides and the second oligonucleotides comprise such groups.

In still other embodiments of the above-described methods, the first oligonucleotides or the second oligonucleotides comprise maleimide groups to be reacted with the thiol groups of the polymer coating. In a preferred embodiment, both the first oligonucleotides and the second oligonucleotides comprise such groups.

In still other embodiments of the above-described methods, the first oligonucleotides or the second oligonucleotides comprise alkene groups to be reacted with the alkene groups of the polymer coating via olefin cross-metathesis. In a preferred embodiment, both the first oligonucleotides and the second oligonucleotides comprise such groups.

In still other embodiments of the above-described methods, the first oligonucleotides or the second oligonucleotides comprise aldehyde groups to be reacted with the oxo-amine groups of the polymer coating. In a preferred embodiment, both the first oligonucleotides and the second oligonucleotides comprise such groups.

In some embodiments of the methods of preparing a surface of a substrate as described herein, the method further comprises the step of staining the polymer coated beads with an optical imaging agent. In some embodiments, the optical imaging agent is selected from the group consisting of Dylight488 phosphine, Dylight 550 phosphine, Dylight 650 phosphine (both from ThermoFisher Scientific), and strained alkyne dyes (DBCO based dyes from Click Chemistry Tools, Inc.) such as: DBCO-Fluor 488, DBCO-Fluor 525, DBCO-Fluor 545, DBCO-Fluor 568, DBCO-Fluor 585, and DBCO-SETA 650. In one embodiment, the optical imaging agent is DyLight488 phosphine.

In some embodiments of the methods of preparing a surface of a substrate as described herein, the substrate can be selected from a silicon substrate, a plastic substrate, or a plastic substrate impregnated with additives. In some further embodiments, the plastic substrate can be impregnated with $SiO_2$, $TiO_2$, or carbon black.

A method set forth herein can use any of a variety of amplification techniques. Exemplary techniques that can be used include, but are not limited to, polymerase chain reaction (PCR), rolling circle amplification (RCA), multiple displacement amplification (MDA), or random prime amplification (RPA). In particular embodiments, one or more primers used for amplification can be attached to a polymer coating. In PCR embodiments, one or both of the primers used for amplification can be attached to a polymer coating. Formats that utilize two species of attached primer are often referred to as bridge amplification because double stranded amplicons form a bridge-like structure between the two attached primers that flank the template sequence that has been copied. Exemplary reagents and conditions that can be used for bridge amplification are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference. PCR amplification can also be carried out with one of the amplification primers attached to a polymer coating and the second primer in solution. An exemplary format that uses a combination of one attached primer and soluble primer is emulsion PCR as described, for example, in Dressman et al., *Proc. Natl. Acad. Sci. USA* 100:8817-8822 (2003), WO 05/010145, or U.S. Patent Publ. Nos. 2005/0130173 or 2005/0064460, each of which is incorporated herein by reference. Emulsion PCR is illustrative of the format and it will be understood that for purposes of the methods set forth herein the use of an emulsion is optional and indeed for several embodiments an emulsion is not used. Furthermore, primers need not be attached directly to solid supports as set forth in the ePCR references and can instead be attached to a polymer coating as set forth herein.

RCA techniques can be modified for use in a method of the present disclosure. Exemplary components that can be used in an RCA reaction and principles by which RCA produces amplicons are described, for example, in Lizardi et al., Nat. Genet. 19:225-232 (1998) and US 2007/0099208 A1, each of which is incorporated herein by reference. Primers used for RCA can be in solution or attached to a polymer coating.

MDA techniques can be modified for use in a method of the present disclosure. Some basic principles and useful conditions for MDA are described, for example, in Dean et al., *Proc Natl. Acad. Sci. USA* 99:5261-66 (2002); Lage et al., *Genome Research* 13:294-307 (2003); Walker et al., *Molecular Methods for Virus Detection*, Academic Press, Inc., 1995; Walker et al., *Nucl. Acids Res.* 20:1691-96 (1992); U.S. Pat. Nos. 5,455,166; 5,130,238; and 6,214,587, each of which is incorporated herein by reference. Primers used for MDA can be in solution or attached to a polymer coating.

In particular embodiments a combination of the above-exemplified amplification techniques can be used. For example, RCA and MDA can be used in a combination wherein RCA is used to generate a concatameric amplicon in solution (e.g. using solution-phase primers). The amplicon can then be used as a template for MDA using primers that are attached to a polymer coating. In this example, amplicons produced after the combined RCA and MDA steps will be attached to the polymer coating.

A third aspect of the present methods disclosed herein relates to a process of determining a nucleotide sequence of a polynucleotide. In such embodiments, the methods can comprise the steps of (a) contacting a polynucleotide polymerase with polynucleotide clusters attached to a surface of a substrate via any one of the polymer coatings described herein; (b) providing nucleotides to the polymer-coated surface of the substrate such that a detectable signal is generated when one or more nucleotides are utilized by the polynucleotide polymerase; (c) detecting signals at one or more polynucleotide clusters; and (d) repeating steps (b) and (c), thereby determining a nucleotide sequence of a polynucleotide present at the one or more polynucleotide clusters.

In some embodiments of the methods described herein, a nucleotide sequence is determined for a polynucleotide attached the surface of the substrate that is present within a flow cell. In some embodiments, the polymer-coated surface is an integral part of the flow cell. In other embodiments, the polymer-coated surface is a separate substrate placed within the flow cell. In further embodiments, the separate substrate may be coupled, attached or otherwise fixed to a surface or other portion of the flow cell.

Nucleic acid sequencing can be used to determine a nucleotide sequence of a polynucleotide by various processes known in the art. In a preferred method, sequencing-by-synthesis (SBS) is utilized to determine a nucleotide sequence of a polynucleotide attached to a surface of a substrate via any one of the polymer coatings described herein. In such process, one or more nucleotides are provided to a template polynucleotide that is associated with a polynucleotide polymerase. The polynucleotide polymerase incorporates the one or more nucleotides into a newly synthesized nucleic acid strand that is complementary to the polynucleotide template. The synthesis is initiated from an oligonucleotide primer that is complementary to a portion of the template polynucleotide or to a portion of a universal or non-variable nucleic acid that is covalently bound at one end of the template polynucleotide. As nucleotides are incorporated against the template polynucleotide, a detectable signal is generated that allows for the determination of which nucleotide has been incorporated during each step of the sequencing process. In this way, the sequence of a nucleic acid complementary to at least a portion of the template polynucleotide can be generated, thereby permitting determination of the nucleotide sequence of at least a portion of the template polynucleotide. Flow cells provide a convenient format for housing an array that is produced by the methods of the present disclosure and that is subjected to a sequencing-by-synthesis (SBS) or other detection technique that involves repeated delivery of reagents in cycles. For example, to initiate a first SBS cycle, one or more labeled nucleotides, DNA polymerase, etc., can be flowed into/through a flow cell that houses a nucleic acid array made by methods set forth herein. Those sites of an array where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., Nature 456: 53-59 (2008), WO 04/018497; U.S. Pat. No. 7,057,026; WO 91/06678; WO 07/123744; U.S. Pat. Nos. 7,329,492; 7,211, 414; 7,315,019; 7,405,281, and US 2008/0108082, each of which is incorporated herein by reference in its entirety.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210, 891; 6,258,568 and 6,274,320, each of which is incorporated herein by reference in its entirety). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WO 12/058096 A1, US 2005/0191698 A1, U.S. Pat. Nos. 7,595, 883, and 7,244,559, each of which is incorporated herein by reference in its entirety.

Sequencing-by-ligation reactions are also useful including, for example, those described in Shendure et al. Science 309:1728-1732 (2005); U.S. Pat. Nos. 5,599,675; and 5,750, 341, each of which is incorporated herein by reference in its entirety. Some embodiments can include sequencing-by-hybridization procedures as described, for example, in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety. In both sequencing-by-ligation and sequencing-by-hybridization procedures, nucleic acids that are present at sites of an array are subjected to repeated cycles of oligonucleotide delivery and detection. Fluidic systems for SBS methods as set forth herein or in references cited herein can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. Science 299, 682-686 (2003); Lundquist et al. Opt. Lett. 33, 1026-1028 (2008); Korlach et al. Proc. Natl. Acad. Sci. USA 105, 1176-1181 (2008), the disclosures of which are incorporated herein by reference in its entirety.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference in its entirety.

Another useful application for an array of the present disclosure, for example, having been produced by a method set forth herein, is gene expression analysis. Gene expression can be detected or quantified using RNA sequencing techniques, such as those, referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array. An array of the present disclosure, for example, having been produced by a method set forth herein, can also be used to determine genotypes for a genomic DNA sample from one or more individual. Exemplary methods for array-based expression and genotyping analysis that can be carried out on an array of the present disclosure are described in U.S. Pat. Nos. 7,582,420; 6,890,741; 6,913,884 or 6,355,431 or US Pat. Pub. Nos. 2005/0053980 A1; 2009/0186349 A1 or US 2005/0181440 A1, each of which is incorporated herein by reference in its entirety.

In some embodiments of the above-described method which employ a flow cell, only a single type of nucleotide is present in the flow cell during a single flow step. In such embodiments, the nucleotide can be selected from the group consisting of dATP, dCTP, dGTP, dTTP and analogs thereof. In other embodiments of the above-described method which employ a flow cell, a plurality different types of nucleotides are present in the flow cell during a single flow step. In such methods, the nucleotides can be selected from dATP, dCTP, dGTP, dTTP and analogs thereof.

Determination of the nucleotide or nucleotides incorporated during each flow step for one or more of the polynucleotides attached to the polymer coating on the surface of the substrate present in the flow cell is achieved by detecting a signal produced at or near the polynucleotide template. In some embodiments of the above-described methods, the detectable signal comprises and optical signal. In other embodiments, the detectable signal comprises a non-optical signal. In such embodiments, the non-optical signal comprises a change in pH at or near one or more of the polynucleotide templates.

EXAMPLES

Example 1

PAZAM Preparation

General

Unless indicated otherwise, all reactions were conducted under a nitrogen or argon atmosphere and starting materials were obtained from commercial suppliers (Aldrich Chemical Company, Fisher Scientific, Dow) and were used as received without further purification. All reaction temperatures recorded indicate the temperature of the bath/air in contact with the reaction vessel. No anhydrous solvents were required.

$^1$H-NMR and $^{13}$C-NMR spectra were recorded in deuterium oxide (for LC NMR 99.9 at % D) on a Bruker Avance 400 MHz instrument. Chemical shifts are expressed in parts per million, (ppm, δ) downfield from tetramethylsilane (TMS) and are referenced to the indicated solvent as internal standard.

GPC analyses were performed by Smithers Rapra Technology Limited using the following Chromatographic conditions:

Instrument: Malvern/Viscotek Triple Detector Array TDA301 with associated pump and autosampler.

Columns: Agilent 1× PLaquagel-OH 40 plus 1× PLaquagel-OH 60, 30 cm, 13 µm, or

Agilent PLaquagel-OH Guard plus 2× PLaquagel-OH Mixed, 30 cm, 8 µm

Eluent: 0.2 M NaNO$_3$; 0.01 M NaH$_2$PO$_4$ adjusted to pH=7.0

Flow-rate: 1.0 mL/min (nominal),

Temperature: 30° C. (nominal)

Detector: Refractive index with differential pressure and right-angle light scattering The data was collected and analyzed using Malvern/Viscotek 'OmniSec' software.

Photoluminescence Spectroscopy

Fluorescence measurements were conducted on a Typhoon Trio Variable Mode Imager (GE) and the data processed using ImageQuant TL software.

Thin films were prepared for the analysis by coating using either spin coating flow methods onto suitably prepared cleaned Si or glass substrates. Photoluminescence spectra of the dry grafted films hybridized with fluorescent complimentary oligos were collected on a Typhoon Trio (GE).

Synthesis

The polymer coating described herein can be prepared in various ways. One method for the synthesis of the polymer of Formula (IIIa) is shown in Scheme 1A.

Scheme 1A. Synthesis of a solution-state PAZAM mixture

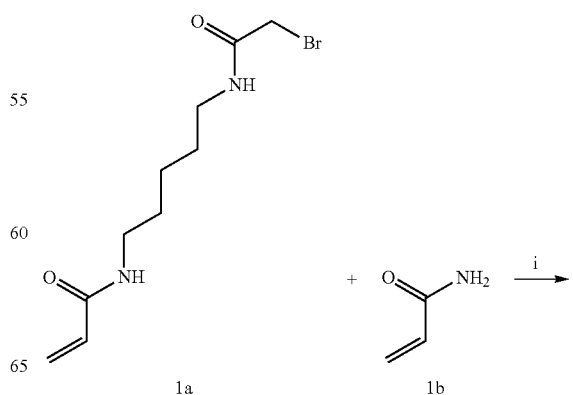

1a                                1b

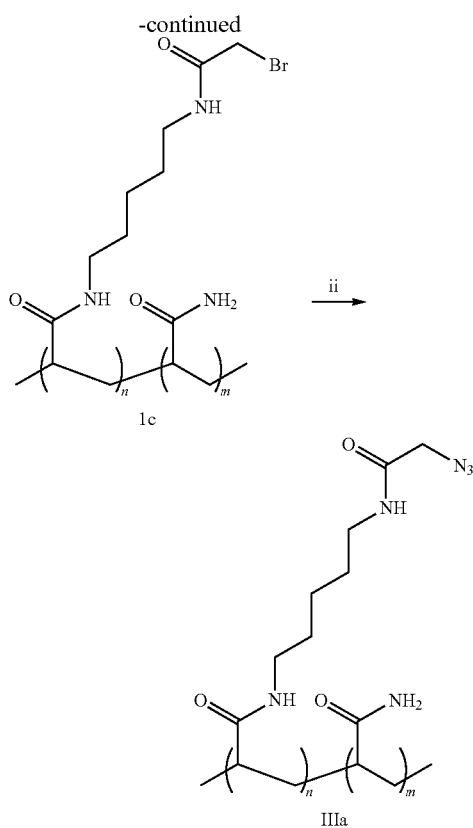

(i) H₂O/DMF, KPS, TEMED, 35° C., 1.5 h
(ii) H₂O, NaN₃, 65° C., 2 h.

The synthesis of N-(5-bromoacetamidylpentyl) acrylamide (BRAPA) (1c) was described in U.S. Pat. Pub. No. 2011/0059865, the disclosure of which is incorporated herein by reference in its entirety.

The water soluble acrylamide polymer (PAZAM) was prepared by a chemically-initiated free radical polymerization. The crude polymer was purified by consecutive precipitations to afford PAZAM with number average molecular weights of 300-400 kDa. Average molecular weights in a wider range can also be obtained, for example, in a range of 30-600 kDa.

Acrylamide (5.0 g, 70.3 mmol) was dissolved in deionized H₂O (45 mL) and the mixture vortexed thoroughly to ensure complete dissolution. In a separate flask, BRAPA (1.0 g, 3.61 mmol) was added to DMF (10 mL, 9.44 g) and the resulting mixture thoroughly vortexed to aid dissolution. A mixture of the BRAPA solution (9.25 g, or 9.80 mL), the aqueous acrylamide solution (47.5 mL) and water (190 mL) were then combined and stirred for 5 min. The solution was then filtered through a 0.2 μm Whatman filter.

Potassium persulfate (125 mg, 0.46 mmol) was added to water (2.5 mL) and the mixture vortexed to dissolve. Sodium azide (11.5 g, 177 mmol) was added to deionized water (82.9 mL) and the solution was vortexed to dissolve. (The final concentration of NaN3 (in the crude polymer mix) is 0.53 M, which corresponds to a 50-fold excess of NaN3 relative to the available BRAPA).

The BRAPA/Acrylamide pre-mix (~250 mL) was purged with argon for 20 min using a plastic pipette. To this monomer mixture were added tetramethylethylenediamine (TEMED) (neat, 273 μL) and potassium persulfate (50 mg/mL; 2370 μL). The mixture was stirred and heated to 35° C. for 1.5 h and then allowed to cool to room temperature. Whilst maintaining stirring, Chainguard 1-15 (1390 μL) was added to the crude mixture, followed by the 2.03 M sodium azide solution (82.9 mL). To ensure complete quenching of any remaining radicals generated during the polymerization, air was bubbled through the mixture for 10 min. The quenched polymer mixture was stirred at 65° C. for 2 h. The mixture was then cooled to room temp temperature and could be stored in this state (at 4° C.) for prolonged periods.

The crude mixture (~335 mL) was added drop wise to a large excess (~1.5 L) of IPA, whilst maintaining gentle stirring. The polymer precipitated as a white solid which was collected and dried at the pump. The partially-dried polymer (~10 g) was redissolved in H₂O (100 mL) by stirring the mixture, at room temperature, for at least an hour to aid dissolution. The viscose solution was then added drop wise to 1.5 L of IPA whilst maintaining stirring. The solid was filtered under vacuum and then dried using a high vacuum to afford PAZAM as a white solid (~5.6 g, >95%). ¹H NMR spectra are shown in FIG. 1A.

Figure 1B:
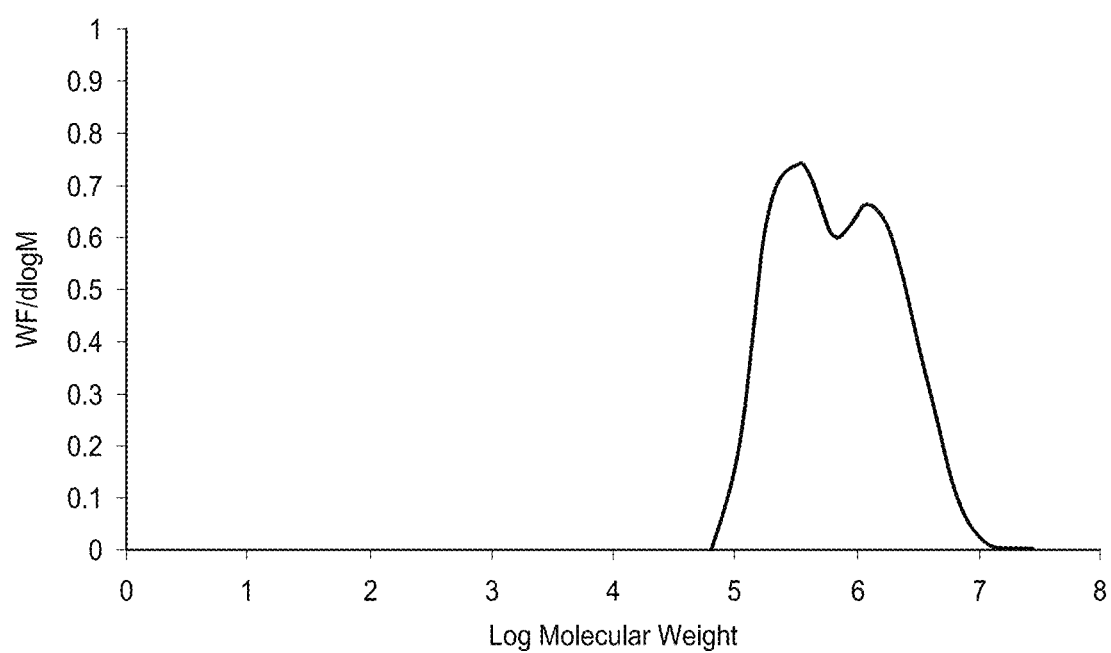
FIG. 1B shows computed molecular weight distributions for PAZAM.

GPC (0.2 M NaNO₃; 0.01 M NaH₂PO₄ adjusted to pH=7.0; calibrated using narrow distribution Pullulan polysaccharide with a peak molecular weight 130,000, an intrinsic viscosity 0.511, and a differential refractive index in 0.1M sodium nitrate of 0.147 mL/g. A value for the differential refractive index (dn/dc) of 0.191 mL/g was used to compute molecular weight data from the sample): $M_n$=3.15× $10^5$ Da, $M_w$=1.0×10⁶ Da, $M_w/M_n$=3.2 (See FIG. 1B). The polymer had a multi-modal MW distribution. The PAZAM sample was difficult to filter prior to starting the chromatographic analysis which contributed to the broad weight distribution and led to measurement artifacts, increasing the complexity of the analysis. The dried PAZAM could then be re-dissolved in water to a desired concentration, typically 0.01 to 12% w/v.

Linear PAZAM Preparation

Alternatively, the synthesis of a linear PAZAM (IIIb) is shown in Scheme 1B.

Scheme 1B. Synthesis of a Linear PAZAM

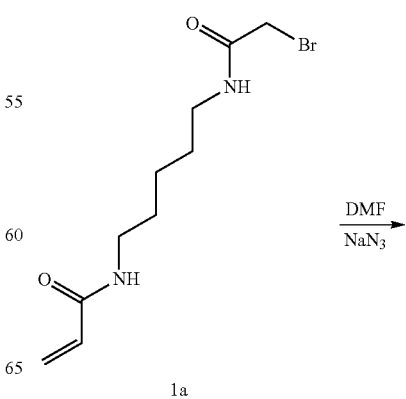

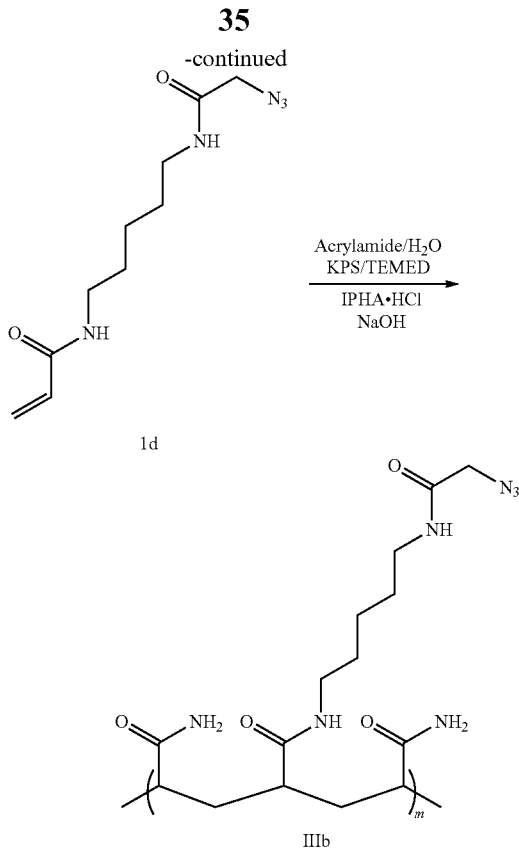

Preparation of 1d/Acrylamide premix: 1a (915 mg), sodium azide (236 mg) and DMF (9 mL) were mixed together in a 25 mL round-bottomed flask equipped with a stirrer bar. The flask was placed in a drysyn bath and the solution was heated under a nitrogen atmosphere with stirring for 2 h at 35° C. (bath temperature) to form 1d. Acrylamide (4.78 g) was dissolved in deionized water, and the resulting 1d solution was added to the acrylamide solution and swirled to mix. The reaction mixture was filtered through a 0.4 μm filter.

A 1 L flange flask was set up in a 1 L drysyn bath on a stirrer/hotplate with a flask lid clamped on. The flask was equipped with an anchor-shaped stirring paddle via a stirrer gland and connect the stirring paddle to an overhead stirrer. An air condenser was attached to one quickfit joint of the flask lid and a tubing adaptor connected to a nitrogen manifold (but without gas flow at this time) was attached to the top of the condenser. The filtered reaction mixture solution was transferred to the flask set up and nitrogen was bubbled through the solution using a 5 mL stripette attached to the nitrogen manifold for 30 mins while preheating the reaction mixture to 35° C. (bath temperature).

Preparation of crude PAZAM polymer solution: Whilst degassing of the acrylamide/1d premix is underway, potassium persulfate (119 mg) was dissolved in deionized water (2.4 mL) with vortexing. The nitrogen flow on the top of the condenser was turned on to ensure a flow of nitrogen over the degassed reaction mixture. After the degassing process, TEMED (99 μL) was added to the reaction mixture while stirring at 200 rpm. Then, potassium persulfate solution was added to the stirred reaction mixture to start polymerization. The stirring was continued at 200 rpm under nitrogen at 35° C. (bath temperature) for 1.5 h.

Polymerization quenching: Whilst the polymerization reaction is underway, IPHA.HCl solution was prepared by dissolving IPHA.HCl (312 mg) in deionized water (2.80 mL). Once the polymerization reaction was underway for 1.5 h, the nitrogen line was removed from the top of the condenser, leaving the reaction vessel open to the air. Sodium hydroxide solution (1M) was added into the stirred reaction mixture, followed by the prepared IPHA.HCl solution to quench the polymerization. The quenched reaction mixture was stirred at 200 rpm at 35° C. (bath temp.) for another 30 mins.

PAZAM polymer purification: The crude mixture was added slowly by stripette to stirred 2-propanol (750 mL) and continued to stir for another 1 h. The solvent was decant off and disposed as sodium azide-containing waste. The precipitated polymer was squashed to squeeze out trapped solvent. The polymer was redissolved in deionized water (150 mL) and the polymer solution was added slowly by stripette to stirred 2-propanol (750 mL) and maintain stirring for another 1 h. The solvent was again decant off and disposed as sodium azide-containing waste. The precipitated polymer was squashed to squeeze out trapped solvent. The resulting polymer was dried in a desiccator under high-vacuum for 18 h and then transferred to a tared, labelled container and store in the dark at room temperature.

Lightly Crosslinked PAZAM Preparation

Similarly, a lightly crosslinked PAZAM was prepared following the general synthetic Scheme 1B with a modified procedure as described herein.

Preparation of 1d/Acrylamide premix: 1a (915 mg), sodium azide (106 mg) and DMF (9 mL) were mixed together in a 25 mL round-bottomed flask equipped with a stirrer bar. The flask was placed in a drysyn bath and the solution was heated under a nitrogen atmosphere with stirring for 2 h at 35° C. (bath temperature) to form 1d. Acrylamide (4.78 g) was dissolved in deionized water, and the resulting 1d solution was added to the acrylamide solution and swirled to mix. The reaction mixture was filtered through a 0.2 μm filter.

A 1 L flange flask was set up in a 1 L drysyn bath on a stirrer/hotplate with a flask lid clamped on. The flask was equipped with an anchor-shaped stirring paddle via a stirrer gland and connect the stirring paddle to an overhead stirrer. An air condenser was attached to one quickfit joint of the flask lid and a tubing adaptor connected to a nitrogen manifold (but without gas flow at this time) was attached to the top of the condenser. The filtered reaction mixture solution was transferred to the flask set up and nitrogen was bubbled through the solution using a 5 mL stripette attached to the nitrogen manifold for 30 mins while preheating the reaction mixture to 35° C. (bath temperature).

Preparation of crude PAZAM polymer solution: Whilst degassing of the acrylamide/1d premix is underway, potassium persulfate (119 mg) was dissolved in deionized water (2.4 mL) with vortexing. The nitrogen flow on the top of the condenser was turned on to ensure a flow of nitrogen over the degassed reaction mixture. After the degassing process, TEMED (99 μL) was added to the reaction mixture while stirring at 200 rpm. Then, potassium persulfate solution was added to the stirred reaction mixture to start polymerization. The stirring was continued at 200 rpm under nitrogen at 35° C. (bath temperature) for 1.5 h.

Polymerization quenching and azidolysis: Whilst the polymerization reaction is underway, IPHA.HCl solution was prepared by dissolving IPHA.HCl (312 mg) in deionized water (2.80 mL). In addition, a sodium azide solution was prepared by dissolving 575 mg of sodium azide in 8 mL deionized water. Once the polymerization reaction was underway for 1.5 h, the nitrogen line was removed from the top of the condenser, leaving the reaction vessel open to the air. After removing one of the stoppers from the lid, sodium hydroxide solution (1M) was added into the stirred reaction mixture, followed by the prepared IPHA.HCl solution to quench the polymerization. Then, the sodium azide solution was added to the stirred reaction mixture. The quenched reaction mixture was heated to 65° C. (bath temp.) and continued stirring stirred at 200 rpm for 2 h while maintain the temperature.

PAZAM polymer purification: The crude mixture was added slowly by stripette to stirred 2-propanol (750 mL) and continued to stir for another 1 h. The solvent was decanted off and disposed as sodium azide-containing waste. The precipitated polymer was squashed to squeeze out trapped solvent. The polymer was redissolved in deionized water (150 mL) and the polymer solution was added slowly by stripette to stirred 2-propanol (750 mL) and maintain stirring for another 1 h. The solvent was again decanted off and disposed as sodium azide-containing waste. The precipitated polymer was squashed to squeeze out trapped solvent. The resulting polymer was dried in a desiccator under high-vacuum for 18 h and then transferred to a tared, labelled container and store in the dark at 4° C.

Figure 1C:
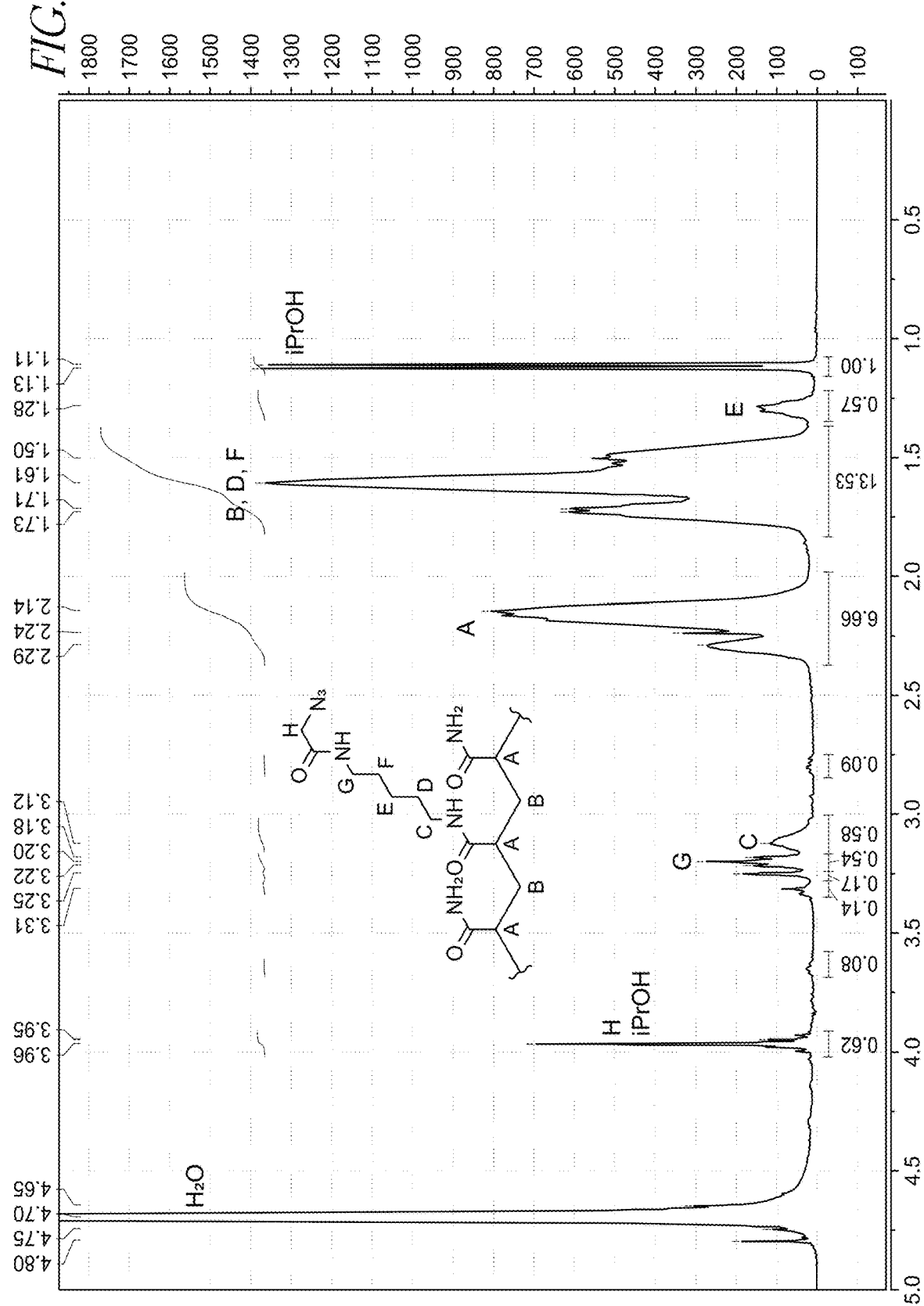
FIG. 1C shows the $^1$H NMR spectrum of a lightly crosslinked PAZAM.

The 1H NMR of the lightly crossed linked PAZAM was obtained from a mixture of 100 µL $D_2O$ with a 500 µL water solution (3%) of the polymer (see FIG. 1C).

Example 2

Preparation of a PAZAM Derivative

The synthesis of a derivative of PAZAM is shown in Scheme 2. First, BRAPA (1c) is reacted with a t-Boc-protected hydroxylamine (2a) to form an intermediate (2b), which is treated with dichloroacetic acid to form an oxo-amine derivative of PAZAM (2c). 2c can be subsequently grafted with aldehyde functionalized oligonucleotides to form 2d.

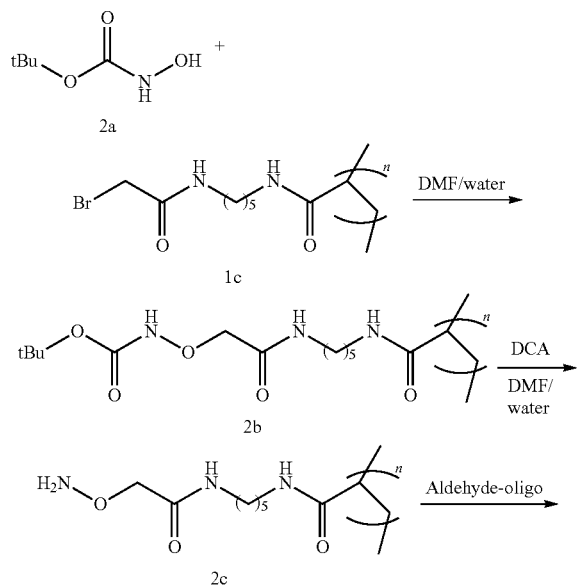

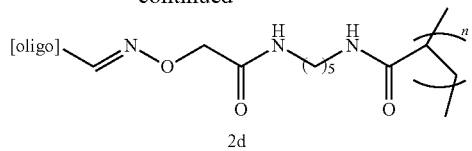

Example 3

Polymer Coatings

PAZAM Coatings on Glass Substrates/Flow Cells

Figure 2A:
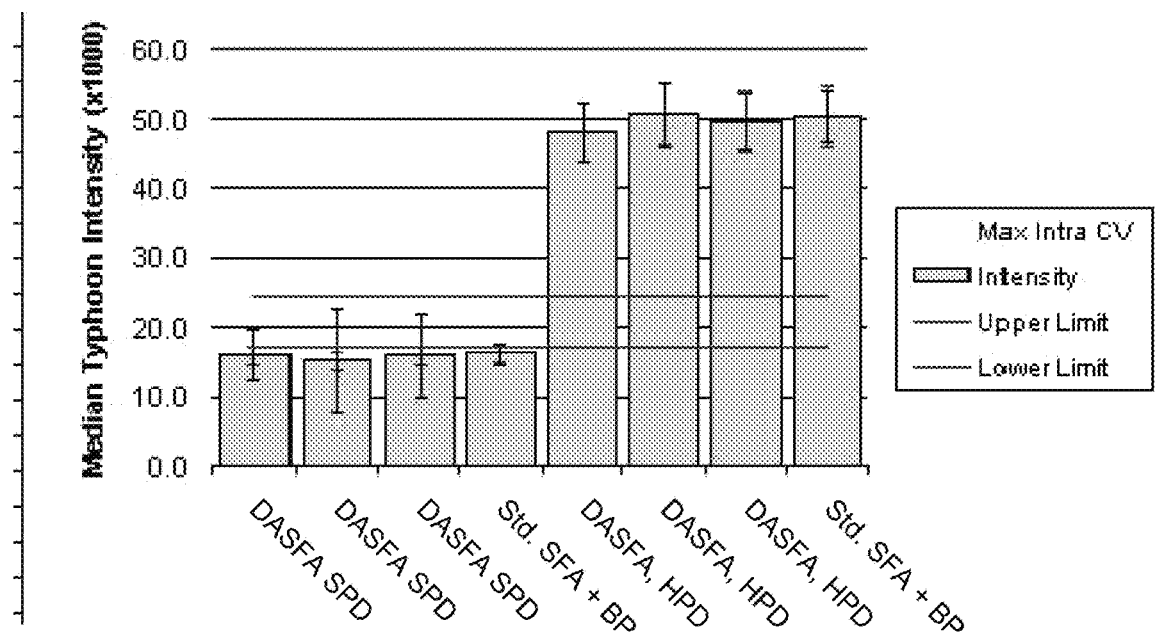
FIGS. 2A and 2B show a Typhoon scan of a typical glass flow cell coated using PAZAM (FIG. 2B) and the median Typhoon intensity (FIG. 2A) along the 8 lanes of the flow cell.
Figure 2B:
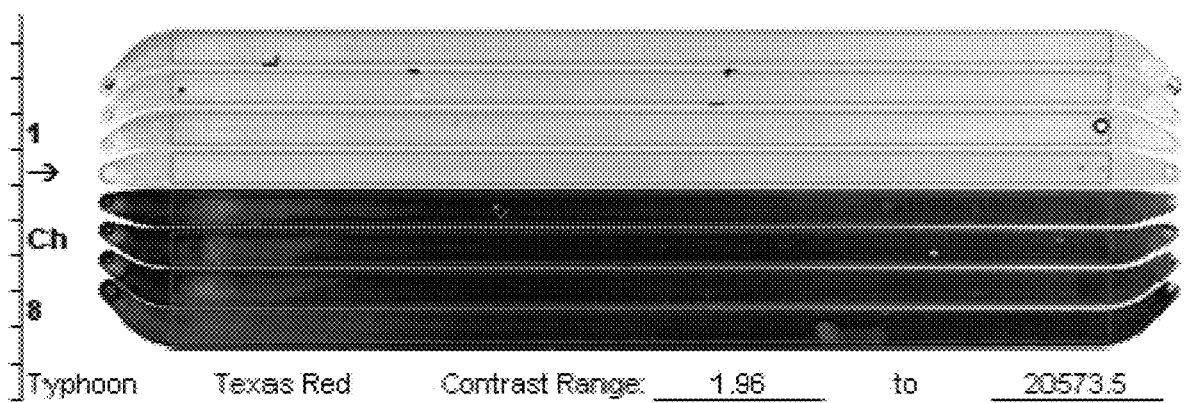

Aqueous PAZAM solutions were deposited onto glass, plastic or silicon substrates. The coatings were subsequently grafted (using an alkyne-functionalized oligonucleotide) and a complimentary dye hybridized to the grafted surface. See FIGS. 2A and 2B. Typical fluorescence scans are provided in FIG. 2B. The polymer was then grafted using primers (alkyne oligonucleotides) at different concentrations to afford a surface that contained four lanes at approximately standard oligonucleotide primer density (~15000 primers/$m^2$) and four lanes at a higher primer density (50000 primers/$m^2$). Primer densities can range from 2500 to 1×10$^6$ primers/$m^2$, depending on grafting primer concentration chosen (FIG. 2A).

Figure 3A:
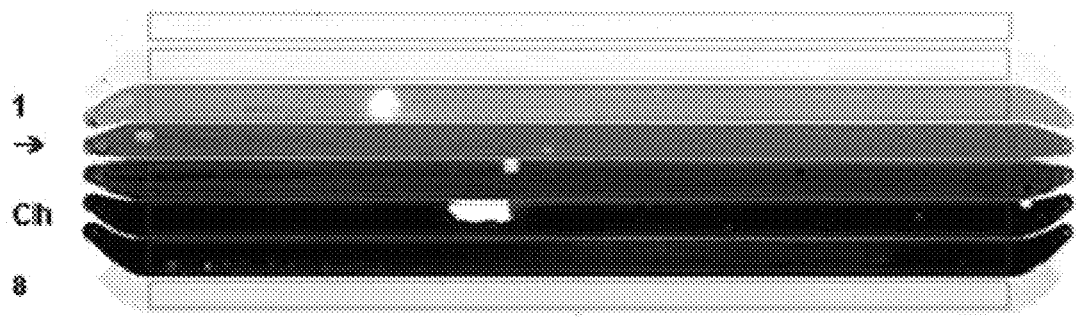
FIGS. 3A and 3B show a Typhoon scan of a HiSeq glass flow cell coated using PAZAM.
Figure 3B:
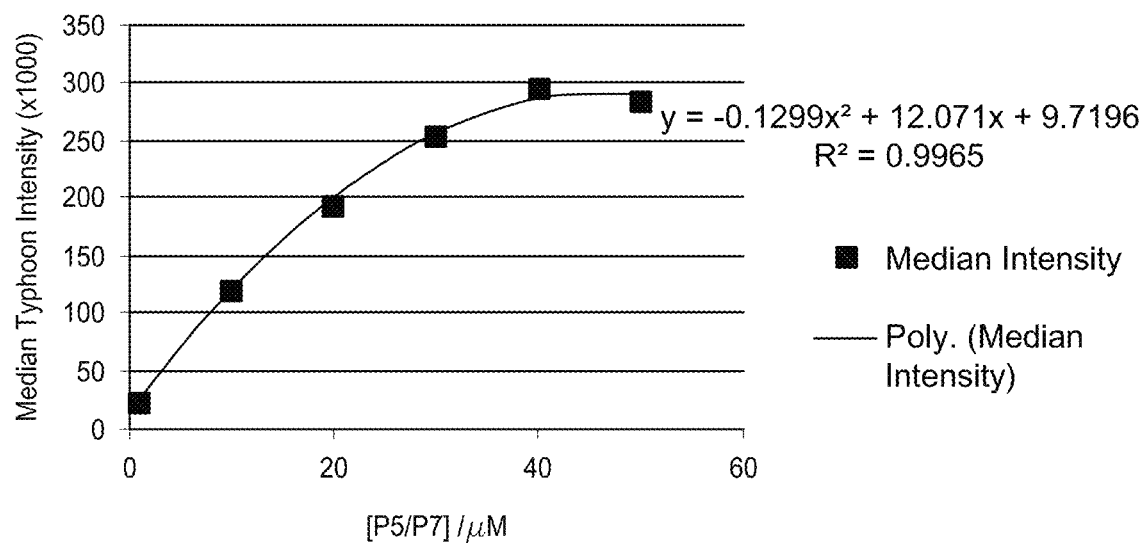

A Typhoon scan of a HiSeq (Illumina) glass flow cell coated using PAZAM is shown in FIG. 3A. The polymer surface was grafted using primers (alkyne oligonucleotides) at increasing concentrations demonstrating the range of primer densities (primers/$m^2$) that can be achieved using this technique (FIG. 3B).

Figure 4A:
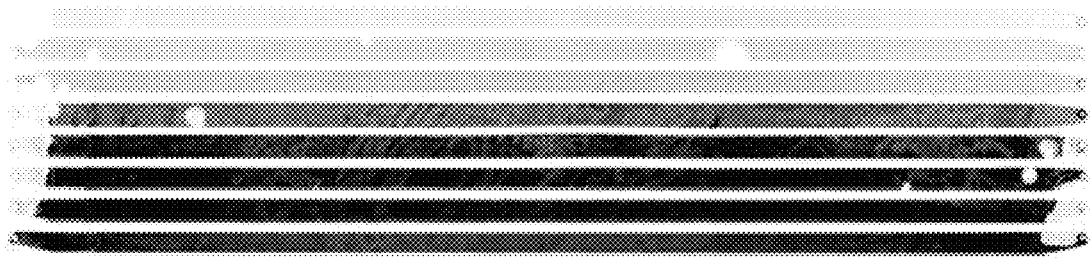
FIGS. 4A and 4B show a Typhoon scan of a glass substrate that has been spin coated using PAZAM.
Figure 4B:
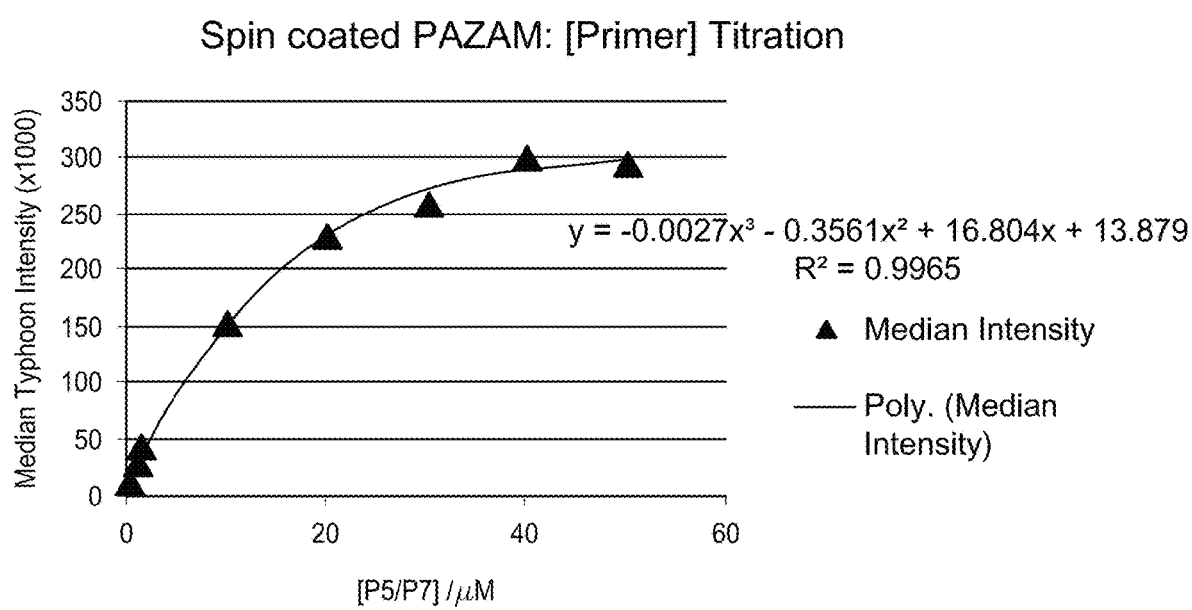

FIG. 4A illustrates a Typhoon scan of a glass substrate that was spin coated using PAZAM. A flow cell sized to fit within the Genome-Analyzer (Illumina) was then fabricated using the wafer. As described in FIGS. 2A and 2B, the polymer surface was then grafted using primers (alkyne oligonucleotides) at increasing concentrations demonstrating the range of primer densities (primers/$m^2$) that can be achieved on a spin-coated surface via this approach (FIG. 4B).

Figure 5A:
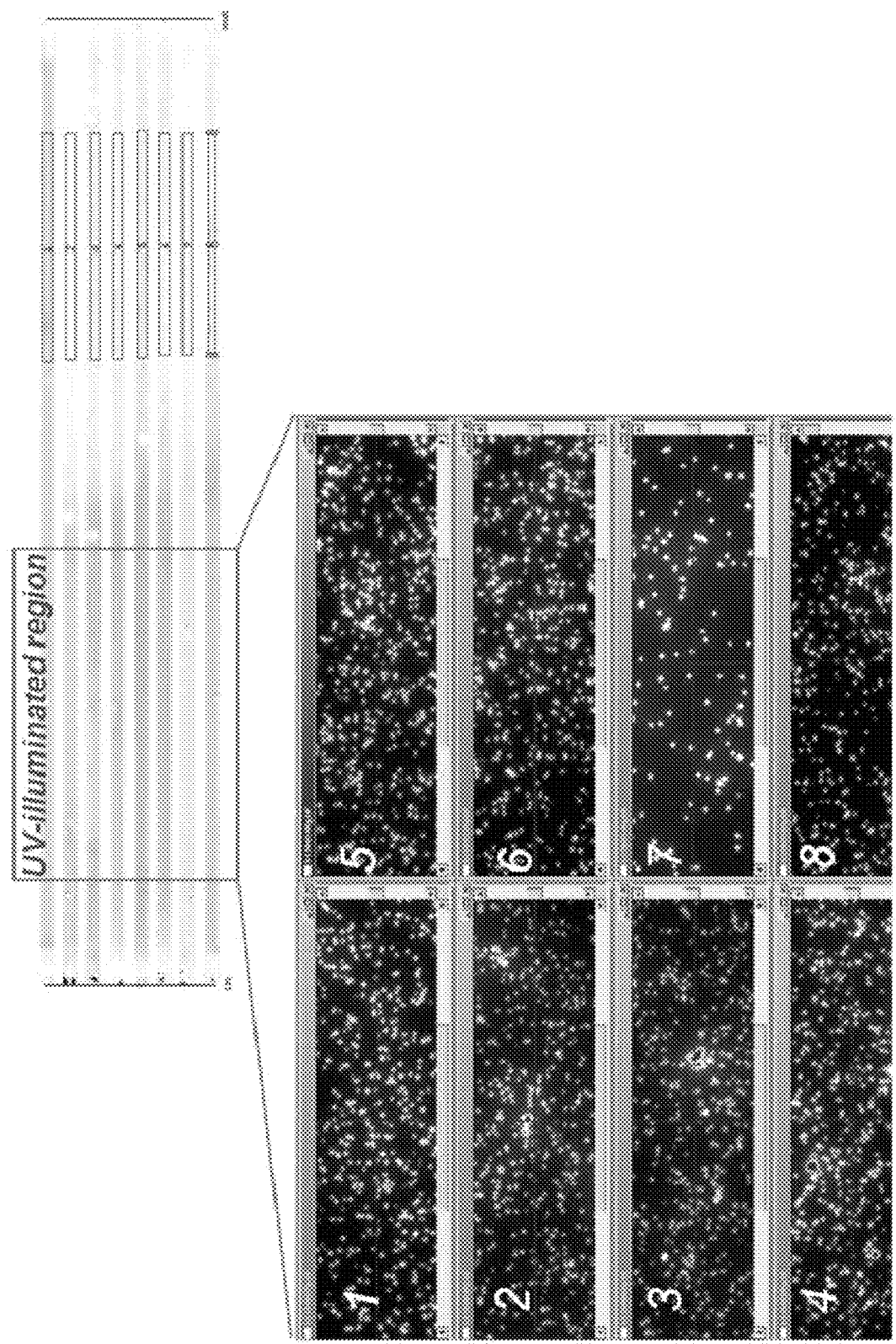
FIGS. 5A-C show clusters on flow-coated PAZAM surfaces.
Figure 5C:
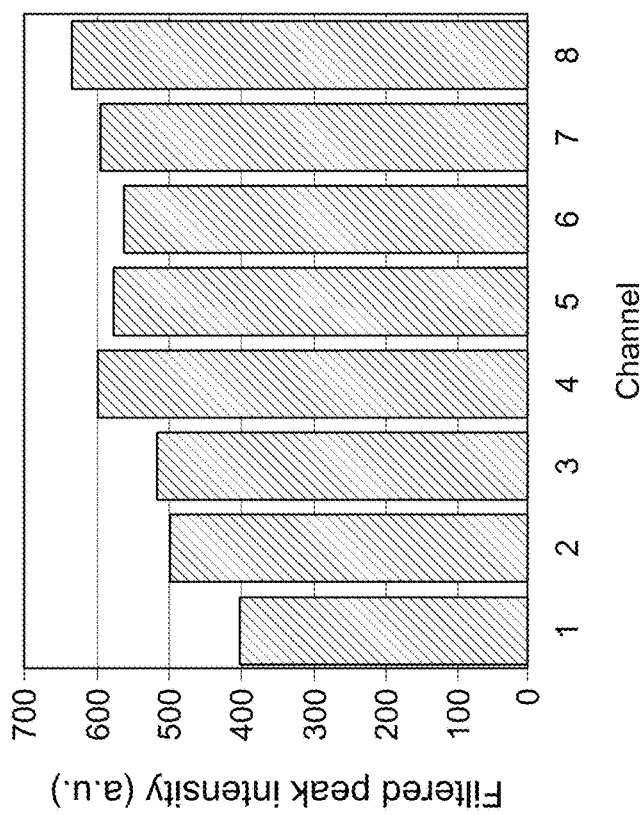
Figure 5B:
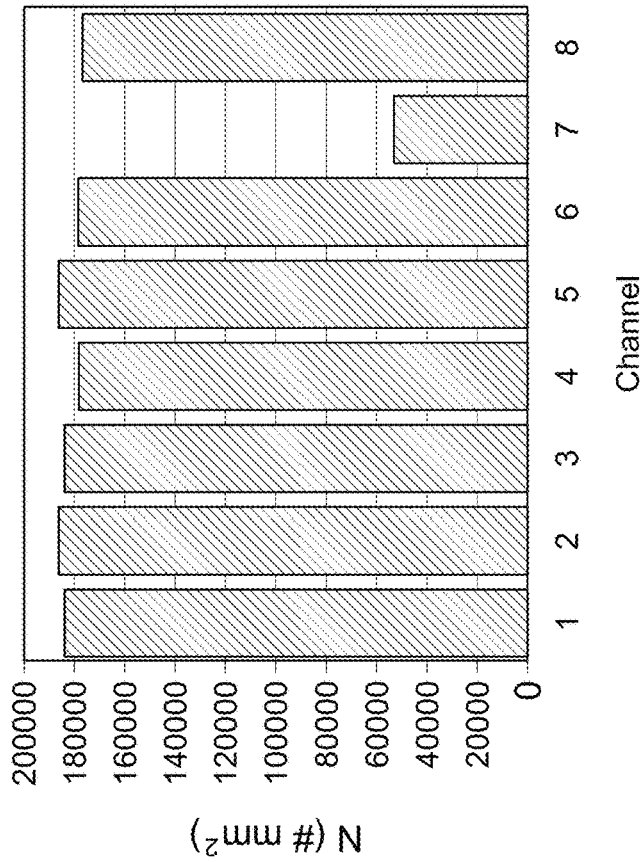

The flow-coated PAZAM surfaces were capable of supporting the amplification of seeded DNA templates. FIG. 5A illustrates that the DNA clusters grown from the templates in the standard SFA channel (lane 1) were identical to those in the PAZAM-coated channels. Clusters were grown using the cBot. 28 cycles cluster amplification ([PhiX]=1 pM, short template, 80 b.p.) then SYBR Green stained. The results demonstrated that this approach provided a robust surface capable of supporting bridge amplification (FIG. 5B and FIG. 5C).

FIGS. 6A and 6B shows the DNA clusters on a spin-coated PAZAM surface. This illustrates that spin-coated PAZAM surfaces were capable of supporting the amplification of seeded DNA template, to give clusters similar to those observed on the standard SFA surface. Typical images of the clusters were obtained using the Manteia (20× objective, 1 mJ exposure) and SYBR Green stain (FIG. 6C).

Poly(N-(5-azidoacetamidylpentyl)acrylamide-co-acrylamide) (PAZAM) Deposition

Materials and Equipment (3-aminopropyl)trimethoxysilane (97%) (APTMS) and isopropanol (Analytical Grade Reagent) (IPA), N,N,N',N',N''-pentamethyldiethylenetriamine (PMDETA), copper sulfate (CuSO$_4$.5H$_2$O, 4% w/v solution) and sodium ascorbate (NaAsc) were purchased from Sigma Aldrich. A 50% IPA aqueous solution was prepared for washes. N-hydroxysulfosuccinimidyl-4-azidobenzoate (Sulfo-HSAB) was purchased from Webscientific. A 2% poly(N-(5-azidoacetamidylpentyl)acrylamide-co-acrylamide) (PAZAM) w/v aqueous solution was prepared in house. The dilution took place in a hybridization oven overnight at 35° C. Potassium phosphate buffer (10 mM aqueous solution, pH=7) (KPi) and sodium chlorate and sodium citrate solution (SSC) were prepared in house. Cleaning of the flow cell was performed using an Emitech K105OX oxygen plasma asher. An MJ Research PTC-200 Thermo Cycler (MJ) was used for solution deposition of sulfo-HSAB and PAZAM. A UVP XX-Series UV Bench Lamp was used for the photochemical reaction of sulfo-HSAB with PAZAM. An Ophir PD300-UV photodiode sensor (20 pW-300 mW) was used to monitor the UV power delivered to the flow cell throughout the photochemical reaction.

Method

A raw flow cell (Illumina) was placed in the plasma asher for 10 minutes at 100 W. The clean glass substrate was then silanized by vapour deposition. The ports of the flow cell were placed on the top of two open glass vials containing 100 µL of neat APTMS in a vacuum desiccator. The desiccator was placed under vacuum and incubated at 60° C. overnight. Upon removal from the vacuum desiccator, the flow cell was placed on an MJ and primed with KPi (10 mM) for 2 minutes at 75 µL·min$^{-1}$. A 21.1 mM sulfo-HSAB solution in 10 mM KPi was then flowed for 2 minutes at 100 µL·min$^{-1}$. A static incubation was performed in the dark for 1.5 hours at room temperature. Subsequent washes were then performed with deionized water, 50% IPA solution and deionized water for 2 minutes at 100 µL·min$^{-1}$ respectively, ensuring no air gap was introduced in the channels of the flow cell. The 2% PAZAM solution was then flowed into the channels for 1 minute at 100 µL·min$^{-1}$, ensuring no air gap was introduced in the channels of the flow cell. Upon removal from the MJ, the flow cell was UV-illuminated using the UV lamp. The distance between the UV-source and the flow cell was 1 cm. The exposure time was adjusted so that 15J per centimeter square area was delivered to the flow cell. The flow cell was then subsequently washed with deionized water, 50% IPA, deionized water and KPi (10 mM) for 2 minutes at 100 µL·min$^{-1}$ respectively. The flow cell was then functionalized by reacting alkyne oligonucleotides in KPi (10 mM) with PMDETA, copper sulfate and NaAsc (500 mg·mL$^{-1}$ aqueous solution) at 60° C. for 30 minutes. The presence of the alkyne oligonucleotides on the surface was confirmed by staining with a complimentary sequenced oligonucleotide functionalized with a fluorescent dye at the 5' end of the alkyne primers.

Results

Fluorescence detection was performed on a Typhoon Trio fluorescent scanner (GE Healthcare). A typical image (FIG. 7B) and graph indicating the median intensities along the channels (FIG. 7A) are shown.

A 2×26 cycle run was completed on a HiSeq 2.6 mm flow cell (Illumina). The first base report indicated that clusters were detected in all lanes (see FIG. 8A through FIG. 8C). Clusters were still present in the channels coated with PAZAM after 26 cycles. Results also showed that PAZAM clusters could be sequenced in the Illumina paired-end protocol, and returning data for 52 cycles (i.e. a pair of 26 cycles). See FIG. 8D through FIG. 8I.

Spin Coating PAZAM onto a Solid Substrate

Figure 7A:
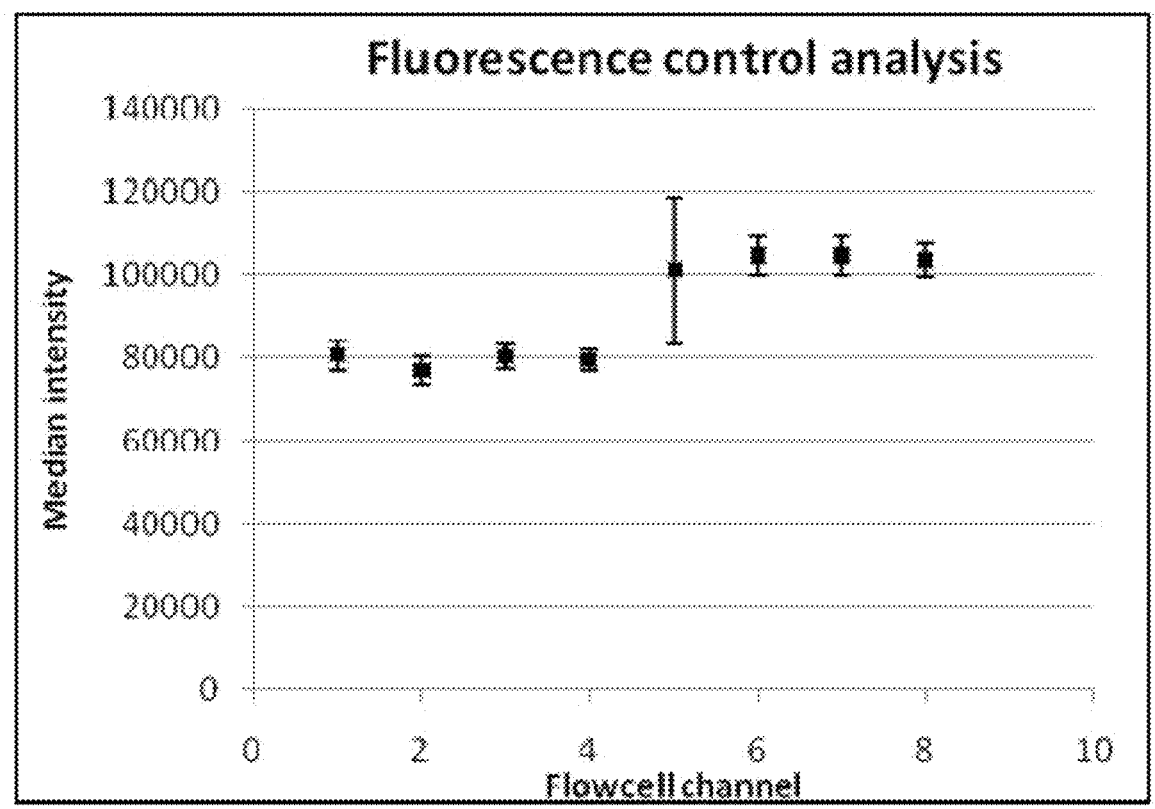
FIGS. 7A and 7B shows a typical flow cell image (FIG. 7B) and median intensity (FIG. 7A) along the 8 lanes of the flow cell.
Figure 7B:
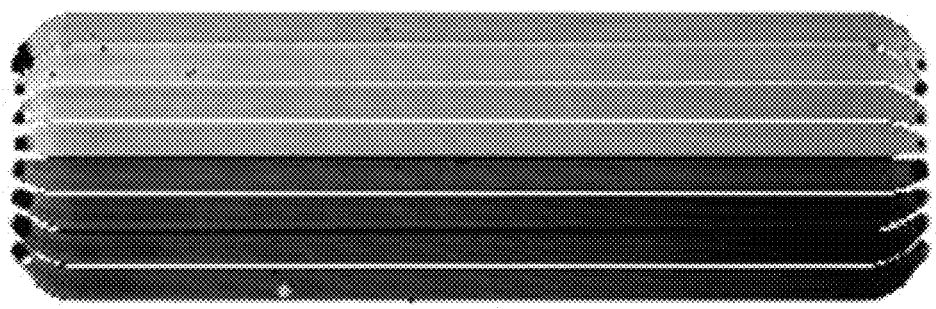

In a typical experiment, a patterned glass substrate was first cleaned by ashing for five minutes in a plasma asher (Emitech K105OX) at 100 W. After cleaning, the substrate was silanized by placing it into a vacuum desiccator containing 0.5 mL of (3-aminopropyl)triethoxysilane (APTES) in open vials. The desiccator was placed under reduced pressure and incubated at 60° C. for one hour. After silanization, the desiccator was opened and the substrate retrieved. The substrate was then placed face down in a petri dish containing a solution of 5 mg/mL N-Hydroxysulfosuccinimidyl-4-azidobenzoate (SHSAB) in 10 mM potassium phosphate buffer (KPi) at pH 7.0. After one hour at room temperature, the substrate was rinsed with water and blown dry with nitrogen. The substrate was placed on the spin coater, and a solution of 2% w/v PAZAM in water was pipetted over the substrate. After spin coating, the substrate was immediately irradiated with 365 nm UV radiation (UVP, lamp XX15 L) for 30 minutes. The surface was then rinsed extensively with water and blown dry with nitrogen. After sealing with a coverslip, the surface was then functionalized by reacting with alkyne oligonucleotides (3×10$^{-9}$ mols) in 10 mM KPi pH 7.0 (1.429 mL), together with N,N,N',N',N''-pentamethyldiethylenetriamine (PMDETA, 13.14 uL, 6.3×10$^{-5}$ mols), copper sulfate (CuSO$_4$.5H$_2$O, 4% w/v solution, 7.49 µL, 1.2×10$^{-6}$ mols) and sodium ascorbate (4.75 µL of a 500 mg/mL solution in water, 1.2×10$^{-5}$ mols) at 60° C. for 30 minutes. The presence of the alkyne oligonucleotides on the surface was confirmed by staining with complimentary sequenced oligonucleotide functionalized with a fluorescent Texas red dye at the 5' end. As shown in FIG. 7A, the fluorescent signal could be detected by scanning on a Typhoon Trio fluorescent scanner (GE Healthcare).

Figure 9:
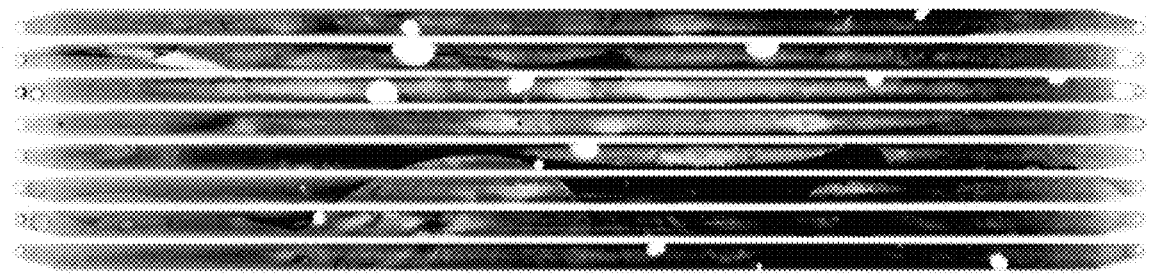
FIG. 9 shows a spin coated substrate functionalized with alkyne oligos hybridized with complimentary fluorescent oligonucleotides.

FIG. 9 shows a spin coated substrate functionalized with alkyne oligos hybridized with complimentary fluorescent oligonucleotides. The dark color indicates the presence of oligonucleotides on a spin coated polymer layer.

Example 4

Preparation of Alkyne Functionalized Surface

Scheme 3. Suggested Synthetic Routes for Preparing Alkyne Functionalized Surfaces

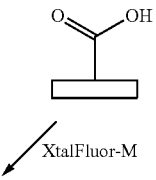

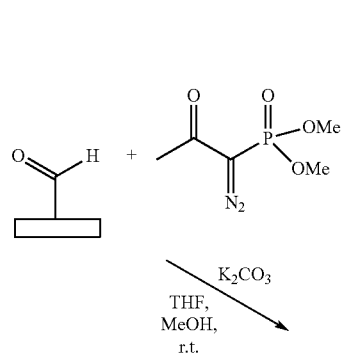
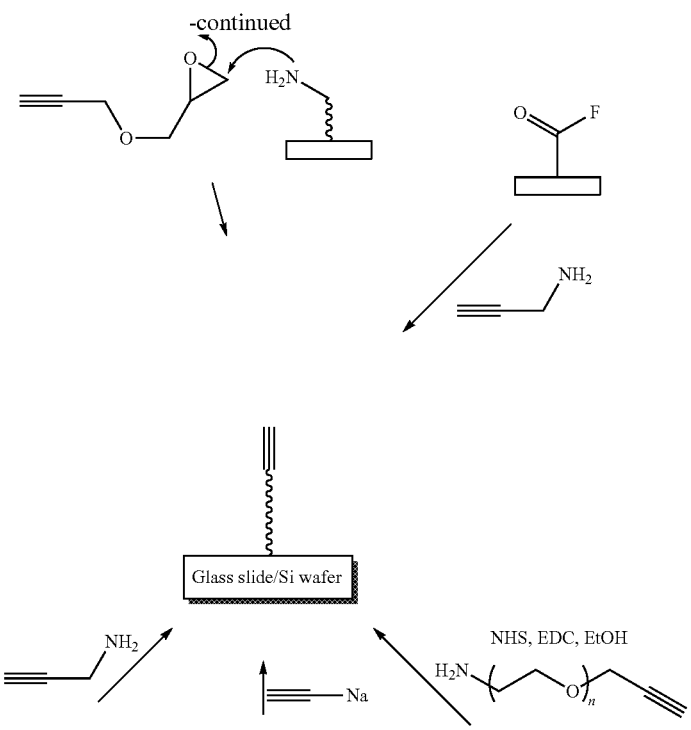
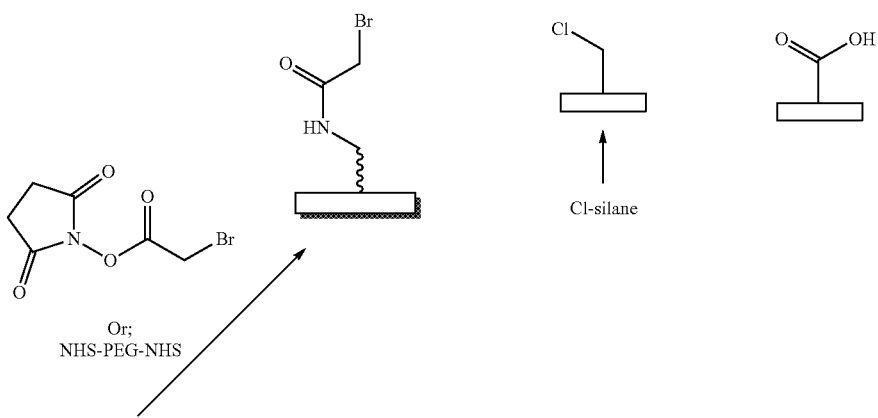
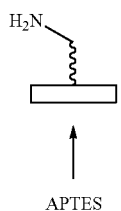

As described herein, various functional groups can be used for polymer locking. Scheme 3 illustrates various suggested synthetic routes for preparing alkyne functionalized surface.

An alternative approach involves the use of the photoactive coupling agent N-hydroxysulfosuccinimidyl-4-azidobenzoate (sulfo-HSAB). Sulfo-HSAB is a commercially available bifunctional crosslinking agent comprising of a photoactive aryl azide and an activated NHS unit. Upon exposure to UV light (~250-374 nm), the aryl azide generates a nitrene with the release of nitrogen. This highly reactive species can undergo a variety of rapid insertion reactions.

Example 5

Preparation of Photo-Active Surface

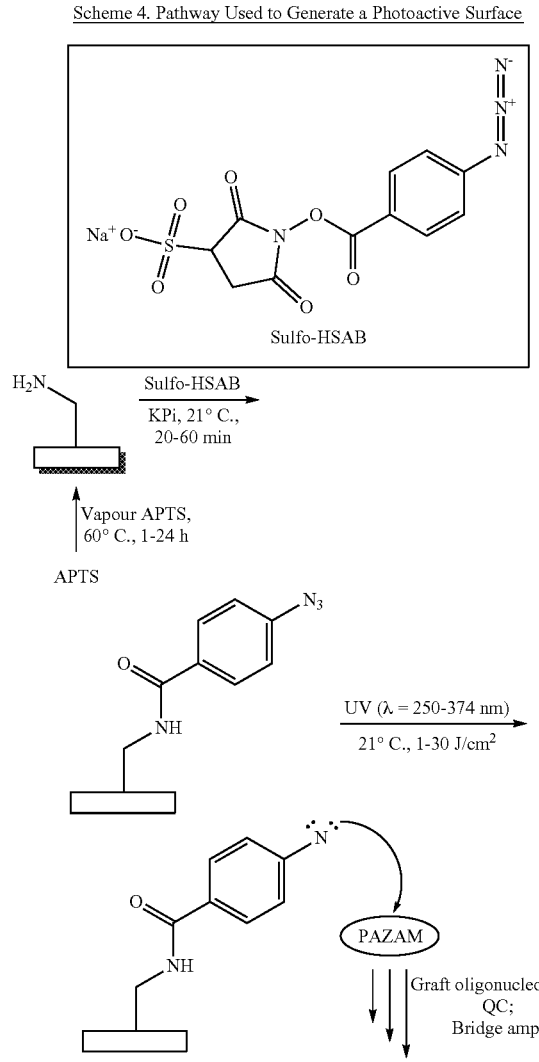

Scheme 4 shows a pathway to prepare a photoactive surface. The surface is pretreated with APTS (methoxy or ethoxy silane) and baked to form an amine group monolayer (or multilayer). The amine groups are then reacted with sulfo-HSAB to form an azido derivative. UV activation at 21° C. with 1 to 30 J/cm$^2$ of energy generates the active nitrene species, which can readily undergo a variety of insertion reactions with the PAZAM.

Initial findings indicate that this approach, involving the use of a photoactive surface and purified PAZAM mixtures, can be used to coat standard GA flow cells (Illumina) and the resulting coatings can be used to grow clusters. Additionally, the polymers can be deposited (e.g. by spin-coating, dunking, dipping, spraying etc.) onto a prepared photoactive wafer with similar results. A coated PAZAM mixture, derived as described in Scheme 4 above, has been taken through to sequencing and a summary of the run is detailed below.

Alternative Crosslinking Agents

In addition to sulfo-HSAB, photostability and efficiency of three other crosslinking agents were also screened and compared with sulfo-HSAB.

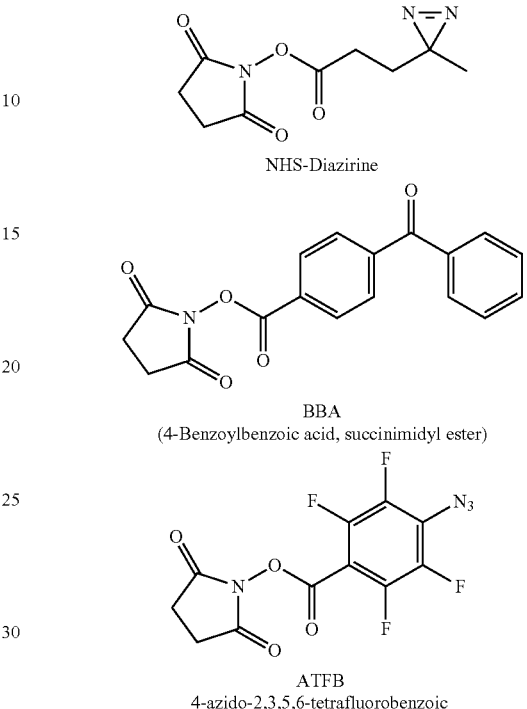

Figure 10A:
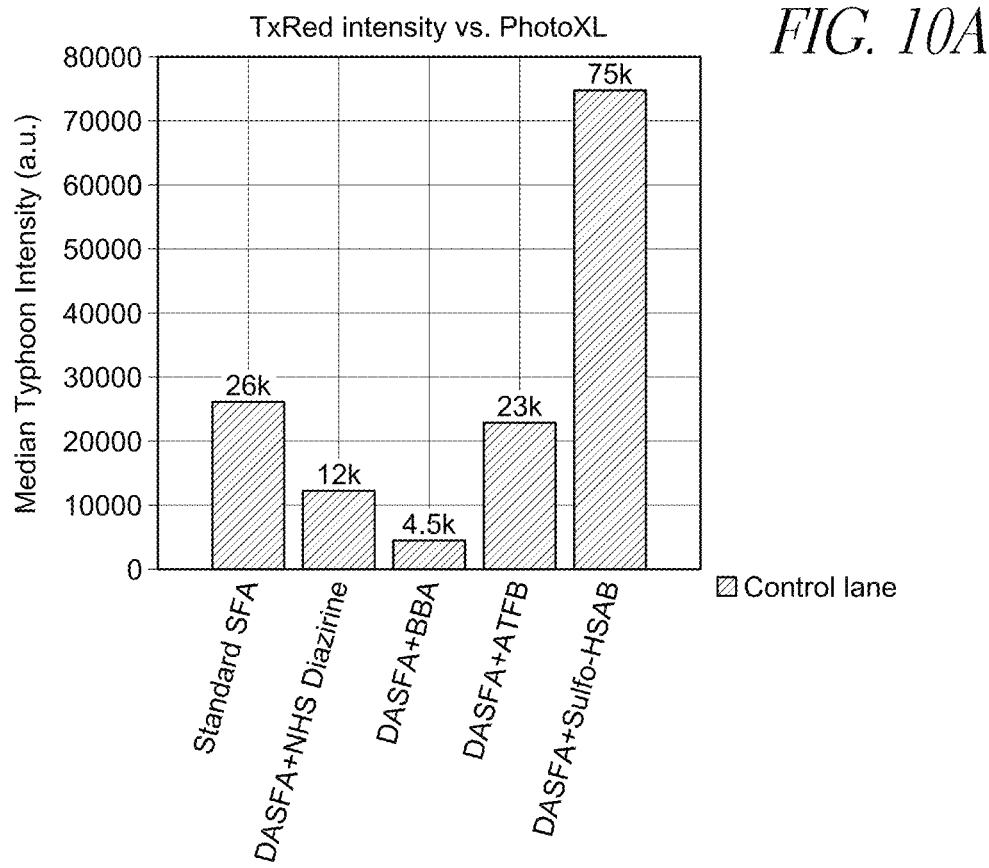
FIGS. 10A and 10B show the screening results of alternative photo-active crosslinkers.
Figure 10B:
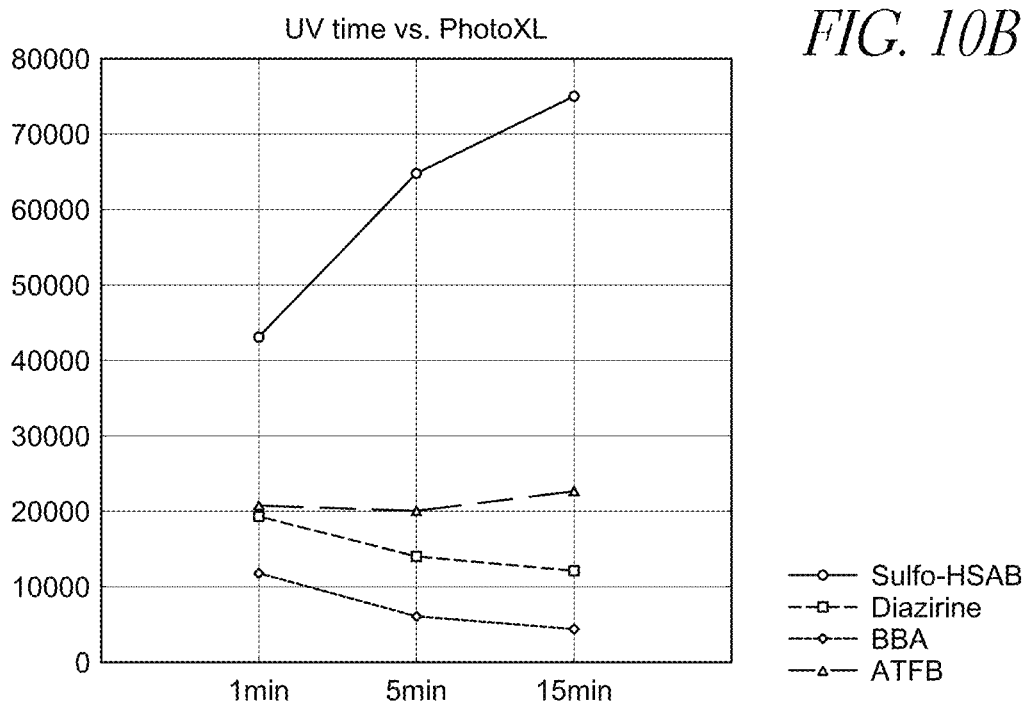

The alternative crosslinking agents were screened using the standard process flow with a GA flowcell (Illumina). The crosslinking agents tested include Sulfo-HSAB, diazirine, BBA and ATFB. The coupling reactions were conducted at 20° C. in DMF at a concentration of about 20 mM. After APTES deposition, alternate lanes of an aminosilane-functionalized flowcell were treated with a 20 mM aqueous/DMF solution of the each of the crosslinkers. The channels were incubated for an identical time as the sulfo-HSAB control channel. After successive washes, PAZAM coating and UV exposure to lock the polymer to the surface, the lanes were grafted with our standard primer oligonucleotides and stained with a complementary fluorescent oligonucleotide sequence. The results post Texas Red hybridization are summarized in FIGS. 10A and 10B.

The performance of the three alternative crosslinkers was assessed by measuring the fluorescent signal of the hybridised complementary oligonucleotides using a Typhoon imager. The results were clear with the measured surface primer densities being less than half of that recorded for sulfo-HSAB. For any of these photoactive crosslinkers (including sulfo-HSAB), the insertion mechanism to form a covalent link with the coated polymer can probably be thermally triggered.

Example 6

Preparation of Unsaturated Surface and Thermal Crosslinking of PAZAM

Another alternative approach for polymer locking is the thermal crosslinking of PAZAM, which includes functionalizing the surface of the substrate with unsaturated groups such as alkene. Scheme 5 illustrates some synthetic routes to generate alkene functionalized surfaces.

Scheme 5. Pathway Used to Generate an acrylamide functionalized surface

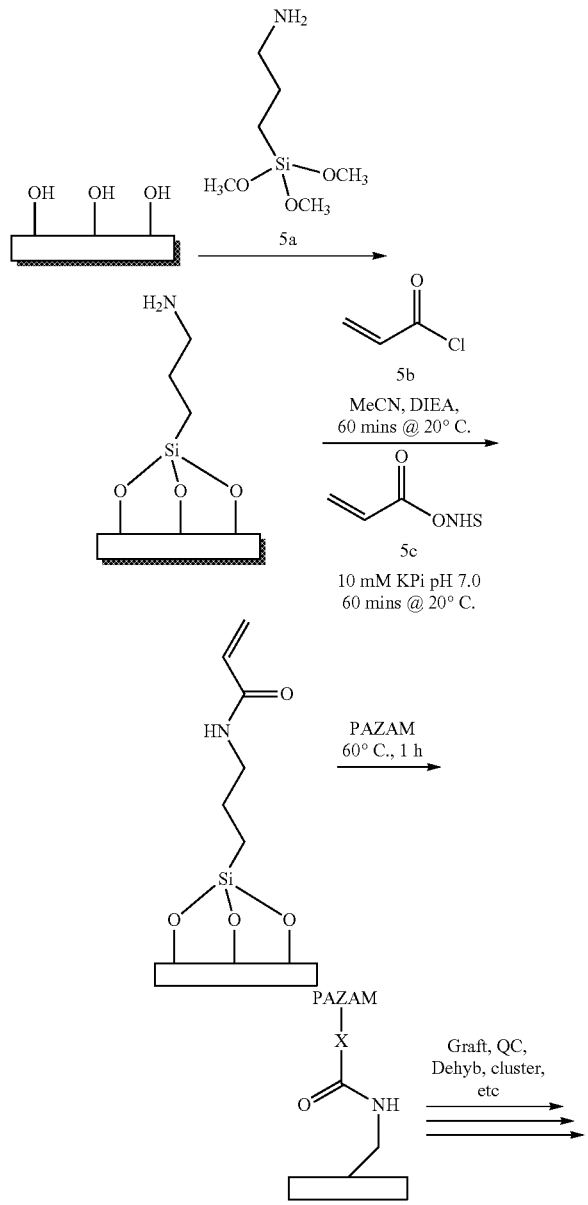

The surface of the substrate was first treated with 3-aminopropyltrimethoxysilane (APTMS) (5a) to form amine functionalized surface. Then amine functional groups was reacted with acryloyl chloride (5b) or activated acryloyl NHS ester (5c). Subsequently, PAZAM was introduced to the unsaturated surface either by pumping a 1-2% PAZAM aqueous solution into the flowcell, or spin coating on top of an open glass slide. The amount of PAZAM that is present in the aqueous solution pumped into a flow cell can be, for example, 0.1-10%. The substrate was incubated at an elevated temperature, typically 60° C. In this process, the azide groups on PAZAM reacted with the unsaturated alkene groups on the surface. Different mechanisms may be involved in this process, as suggested by Krülle et al., *Tetrahedron: Asymmetry* (1997), 8: 3087-3820, which is incorporated herein by reference in its entirety.

Figure 12:
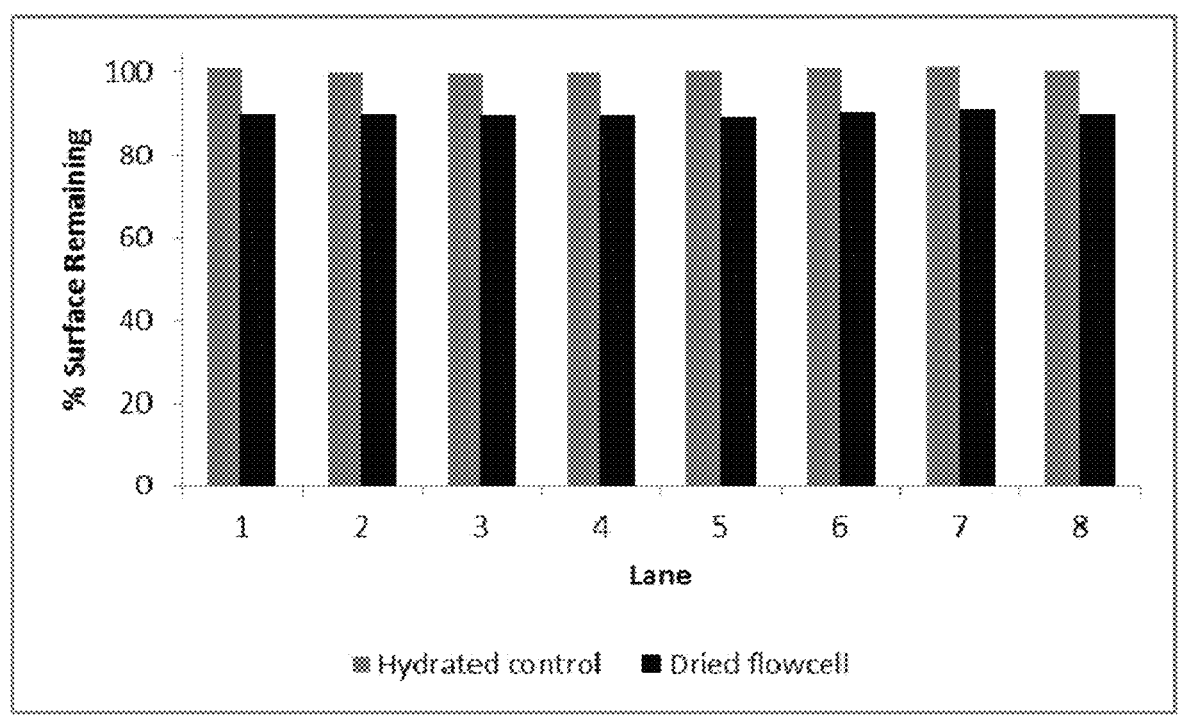
FIG. 12 illustrates the percent surface remaining on a thermal crosslinked PAZAM layer after six days stored at room temperature with less than 10% humidity.

After a wash with water or aqueous buffer to remove excess unreacted PAZAM, the surface can be grafted to nucleic acid primers. Standard technique can be used in all other downstream processes, e.g., QC or cluster growth. The surface has similar performance characteristics to the polymer locking through UV activation. For example, it can be grafted with different concentrations of grafting primers to achieve different primer densities. It can also be dehydrated, stored dry and rehydrated, maintaining an active surface throughput (see FIG. 12).

Example 7

Application of Polymer Coating in Clusters and Sequencing

In FIGS. 8A-I, a 2×26 cycle run was completed using a PAZAM-coated HiSeq flow cell (Illumina). The first base report indicated that clusters were detected in all lanes. In addition, PAZAM clusters were still present after 26 cycles. PAZAM clusters finished a paired-end read and returned data for a complete 52 cycles (i.e. a pair of 26 cycles).

Figures 13A, 13B:
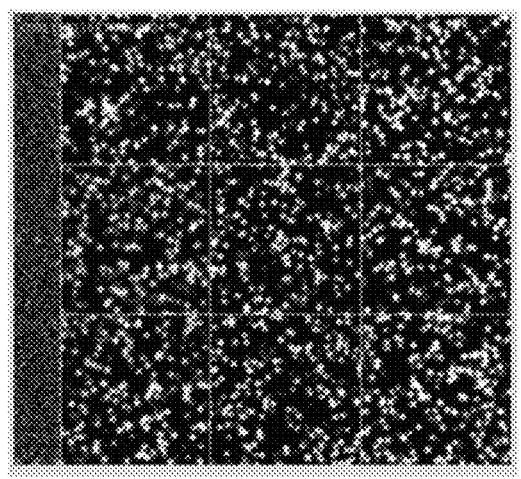
FIG. 13A illustrates the cluster grown with 5 PhiX template on a thermal crosslinked PAZAM surface.
FIG. 13B illustrates the sequencing metrics after a 2×26 cycle run on a thermally crosslinked flowcell.

The polymer coated surface prepared by the thermal crosslinking method is also active for cluster growth and sequencing using the standard methods as described herein. FIG. 13A shows clusters grown on a thermally crosslinked surface with PhiX V3 as a template, imaged on a Hi-Seq (Illumina). FIG. 13B illustrates the sequencing metrics obtained from a 2×26 cycle run on a Hi-Seq with conventional sequencing chemistry.

Example 8

Application of Polymer Coating in Patterning

In addition to coating regular flow cells, the generation of a photoactive layer can also be used to form a patterned surface. Microfabrication techniques can commonly be used to create "islands" of amino functionality in a "sea" of inert or passive material.

An aryl azide, like sulfo-HSAB, can be located on the amino core to create a patterned photoactive layer. Coating this surface with a polymer mixture like PAZAM followed by UV exposure and subsequent washing leaves a polymer-patterned array. This process is demonstrated in FIG. 11A.

Figure 11B:
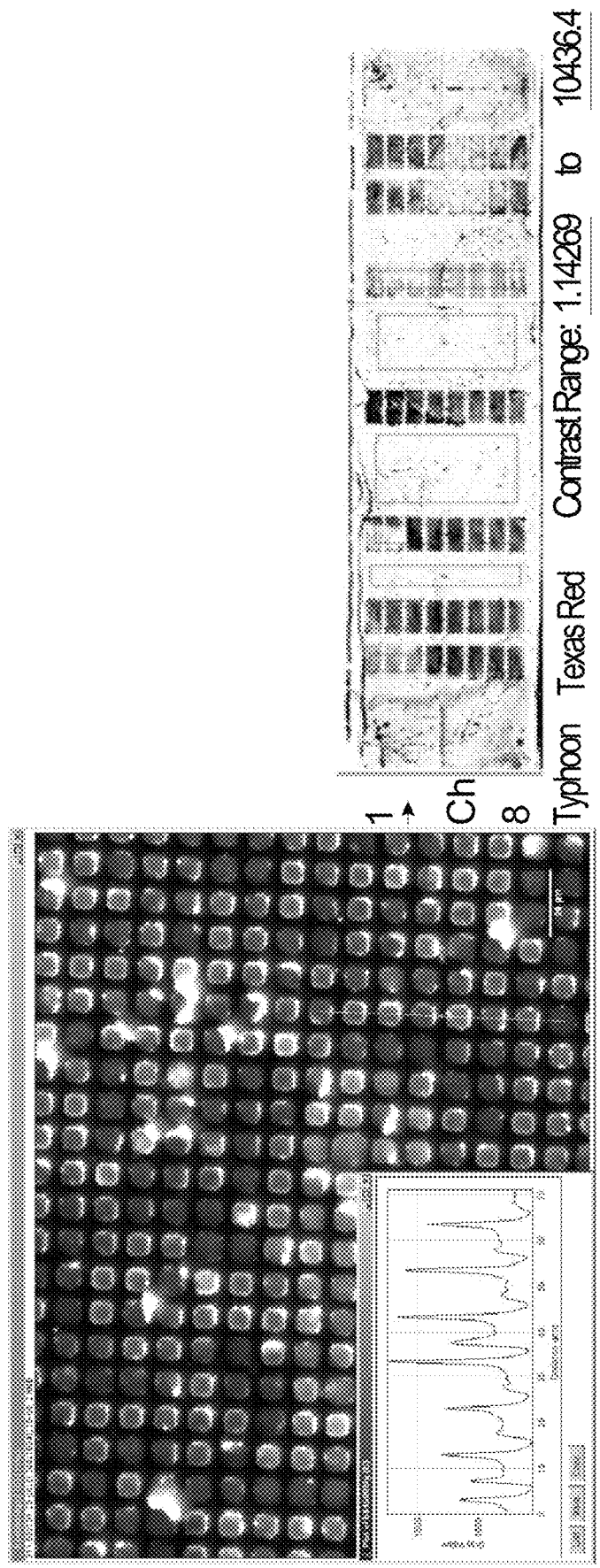

The background region is left free of any photocoupled polymer because the crosslinker is located only in the patch. The radical insertion reaction is confined to a monolayer at the surface minimizing the uncontrolled propagation of radicals. Aryl azides functionalized with silane and phosphate units can also be readily accessed from commercially available starting materials, allowing anchoring to a wide variety of patch types (see FIG. 11A). Preferential polymer deposition in the functionalized feature patches was observed using a slide with bare glass features and a gold interstitial region (FIG. 11B). The right side shows a Manteia fluorescence image and the left side shows a Typhoon image of the slide, with the darker areas indicating an increased polymer coating.

Figure 14:
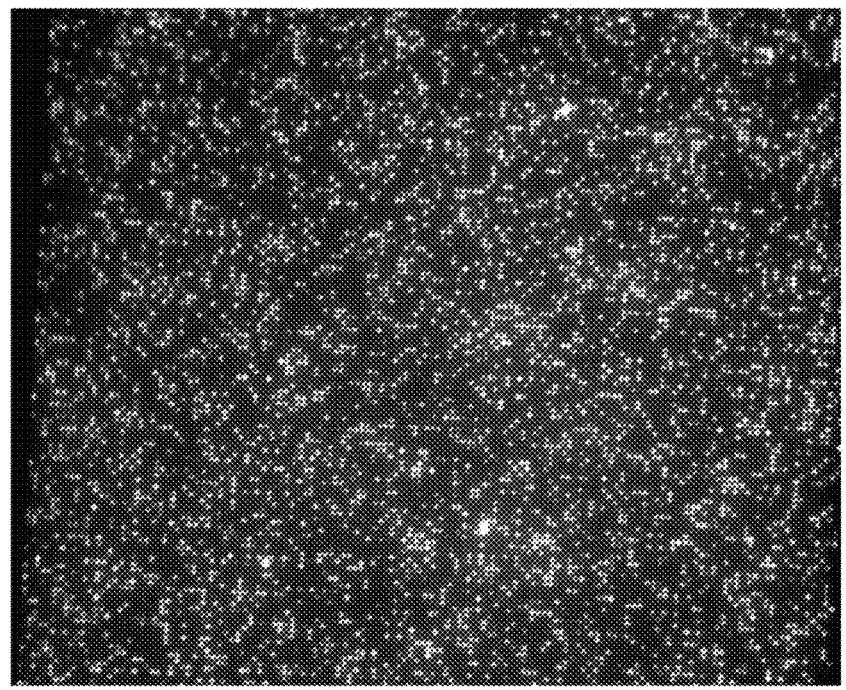
FIG. 14 illustrates the cluster grown on a patterned array made by thermally crosslinking PAZAM to patterned silane patches.

Similarly, the thermal crosslinking method also enables the formation of patterned patches of functional polymer when the underlying functional layer is patterned. For example, patches of patterned aminosilanes can be prepared using common lithographic techniques. Typically, this involves coating a substrate with a resist, exposing then developing the resist to leave bare patches on the substrate. The bare patches are then functionalized with the silane, followed by removing the bulk of the resist and leaving behind small patches of amino functionalized substrate with a bulk interstitial of non-functional substrate. These patches can then be functionalized with the unsaturated alkene groups as shown in Scheme 5, and then incubated with PAZAM. The resulting surface comprises of small patches of PAZAM in a predefined grid, which can then support cluster growth on a defined patterned array. In FIG. 14, a surface made as described above is shown to support bridge amplification selectively on the patterned regions. The features are 450 nm in diameter with a pitch of 1.4 µm. Clusters were grown using an Illumina V3 PE cBot kit with 1 pM human DNA template. The surface was imaged with Sybr green after amplification.

Other methods for making patterned surfaces that can be used include, for example, those described in U.S. Ser. Nos. 13/492,661 and 13/661,524, each of which is incorporated herein by reference.

Example 9

Coating Beads with PAZAM

Various methods can be used to apply a polymer coating to beads. One approach described herein includes the use of a UV activable surface for polymer locking. An alternative approach described in Example 11 includes the use of an alkene or acrylamide functionalized surface for thermal crosslinking of the polymer. In the thermal-based approach, the bead is generally exposed to wash solutions containing a polymerization inhibitor (for example, BHT, diethylhydroxylamine, or TEMPO, etc.) after functionalization with alkene or acrylamide groups. This can be done to prevent the beads from aggregating due to premature polymerization of the alkene or acrylamide groups.

After coating PAZAM on the beads, the beads were washed to remove excess unbound PAZAM. The PAZAM layer was about 20 nm thick after washing. The beads were then grafted to primers (mixes of P5/P7) via reacting the azide groups on PAZAM with a 5' alkyne modified oligonucleotide. Alternative grafting chemistry can also be used, which includes but is not limited to: reacting the amine groups in the polymer with 5'-NHS modified oligonucleotides; reacting the oxo-amine groups in the polymer with 5'-aldehyde modified oligonucleotides to form oxime; reacting the thiol groups in the polymer with 5'-maleimide modified oligonucleotides; olefin crossmetathesis (reacting the terminal alkene groups in both the polymer and the 5'-modified oligonucleotides in the presence of a metathesis catalyst); reacting the amine groups in the polymer with 5'-cyanuric chloride modified oligonucleotides; etc. The excess primers not grafted to the PAZAM on the bead can then be washed away, leaving beads with a PAZAM-oligo layer on them.

Several methods can be used to perform quality control on the polymer coated beads before application to the surface of the substrate. One method is to directly stain PAZAM with dyes (for example, Dylight488 Phosphine). Another method is to label the grafted oligonucleotides with dye-labeled reverse complements of the oligonucleotides on PAZAM. The labeled beads can be measured by flow-cytometry, or cast onto a surface and then analyzed by light microscopy (including fluorescent light microscopy). Also, an aliquot of the beads can be used in a destructive test to assess how the beads will perform in an assay. One example is to load an aliquot onto a substrate, perform sequencing, and determine if the bulk of the beads are good enough to use for loading onto many arrays.

Figure 15:
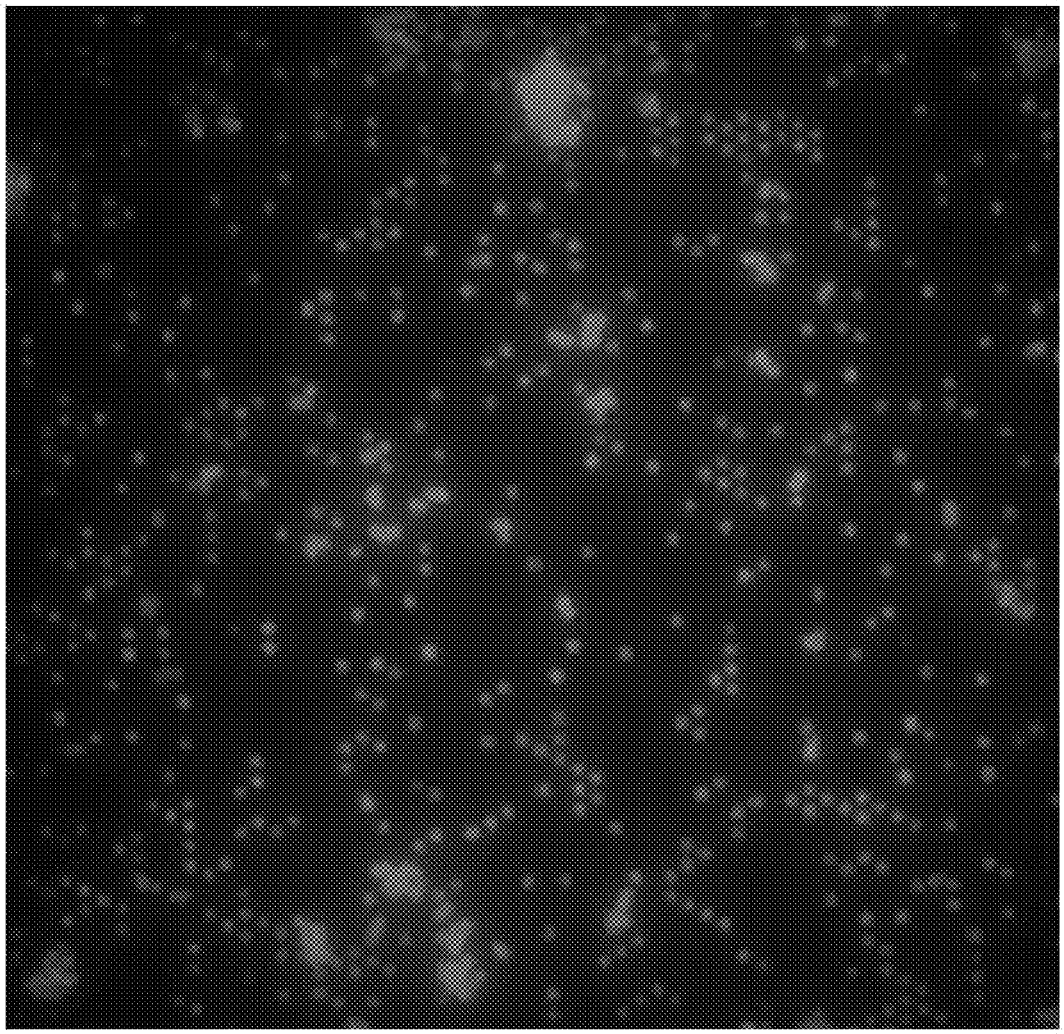
FIG. 15 illustrates a patterned PAZAM arrays prepared by PAZAM coated beads.

Different types of etchable substrates can be used for beads loading, for example, silicon, plastic (Zeonor®), and plastic impregnated with additives (e.g., SiO$_2$ or carbon black). FIG. 15 illustrates the patterned PAZAM arrays prepared by loading PAZAM-covered beads onto clear Zeonor slides.

There are several advantages of using polymer coated beads for the preparation of patterned arrays. First, the bead approach is cost-effective and time-saving. The bead loading approach enables the preparation of an array surface with high density compared with conventional approaches of coating and grafting flow cells. An exemplary convention approach uses a device that delivers different reagents to the flow cell and allows the flow cell temperature to be controlled, which results in only a fraction of the pumped primers being grafted resulting in substantial waste. In addition, the bead loading procedure described herein is much faster than the conventional procedure and allows for large scale commercial applications.

Example 10

Photoactive Polymers

Disclosed herein is the use of alternative water-soluble polymers that are capable of supporting bridge amplification and subsequent Sequencing By Synthesis (SBS) chemistry. In addition, the polymer can readily be applied to surfaces using a variety of different techniques. In particular, developing a linear polymer that can be fully characterized prior to being applied to the surface is beneficial in order to limit the potential variation in the quality of the surface coating. In addition, the approach described herein includes the ability to use alternative coating strategies, including dip, spray, and spin-coating of the polymer.

Scheme 6 shows the preparation of a linear polymer that can be prepared using commercially available starting materials. The polymer can be used to coat, in a controllable fashion, glass and silicon wafers allowing full characterization for both the solution polymer and the coated wafer prior to fabrication into flow cells. This method also allows one or both flow cell surfaces to be functionalized as appropriate.

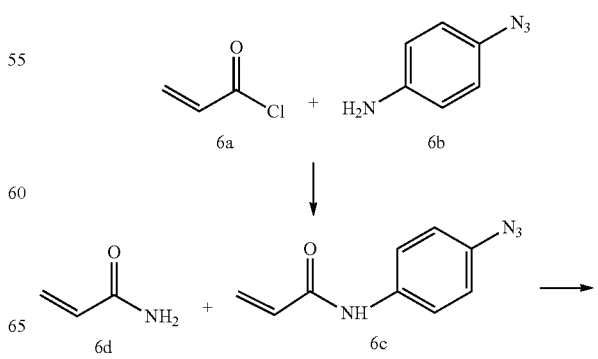

Scheme 6. Synthesis of a Photoactive Linear Polymer

-continued

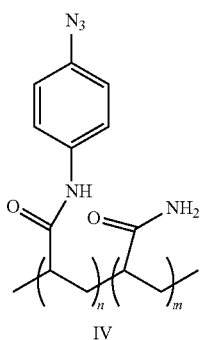

IV

The polymerization can be conducted on a large scale using traditional solution-phase techniques. Acrylamide and a new monomer 6c (synthesized via a simple one-step procedure), can be polymerized using free-radical polymerization analogous to the current procedure for preparing PAZAM.

One modification involves the use of perfluoroaryl azides (Keana, J. F. W.; Cai, S. X. New Reagents for Photoaffinity Labeling: Synthesis and Photolysis of Functionalized Perfluorophenyl Azides. *J. Org. Chem.* 1990, 55, 3640-3647), the disclosure of which is incorporated herein by reference in its entirety. These species display a reduced tendency to undergo ring expansion upon generation of the nitrene. As a result the UV-triggered reaction is cleaner with the exclusive formation of insertion products.

Scheme 7. Synthesis of a Perfluoro Aryl Azide Monomer for Preparing a Photoactive Polymer

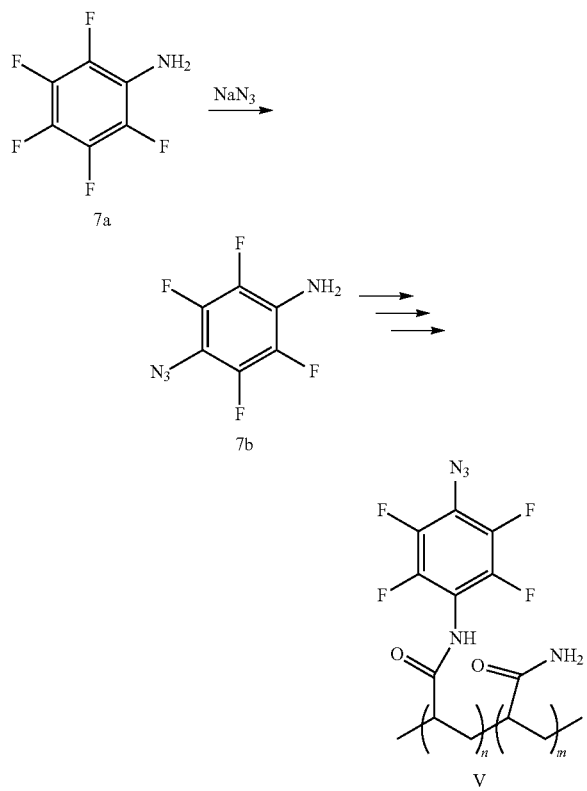

The use of aryl azides as labeling agents was reported as far back as 1969. (Fleet, G. W. J.; Porter, R. R.; Knowles, J. R. Affinity Labeling of Antibodies with Aryl Nitrene as Reactive Group. *Nature* 1969, 224, 511-512), the disclosure of which is incorporated herein by reference in its entirety. In the present application, the dual reactivity of these functional groups is exploited; as a partner in the 1,3-dipolar cycloaddition (for grafting of the oligos) and a photocoupling agent after UV-triggered generation of a singlet nitrene species. The advantage of using a UV-active monomer is that the reaction is "clean" (insertion products only), chemoselective and localized with the polymer environment providing a vast number of insertable bonds.

This approach eliminates the need to perform any post-deposition functionalization steps. Once coated with the pre-grafted polymer, the wafer can be diced, a coverslip attached and a QC step performed in order to determine/confirm the number of available surface primers.

Figure 16:
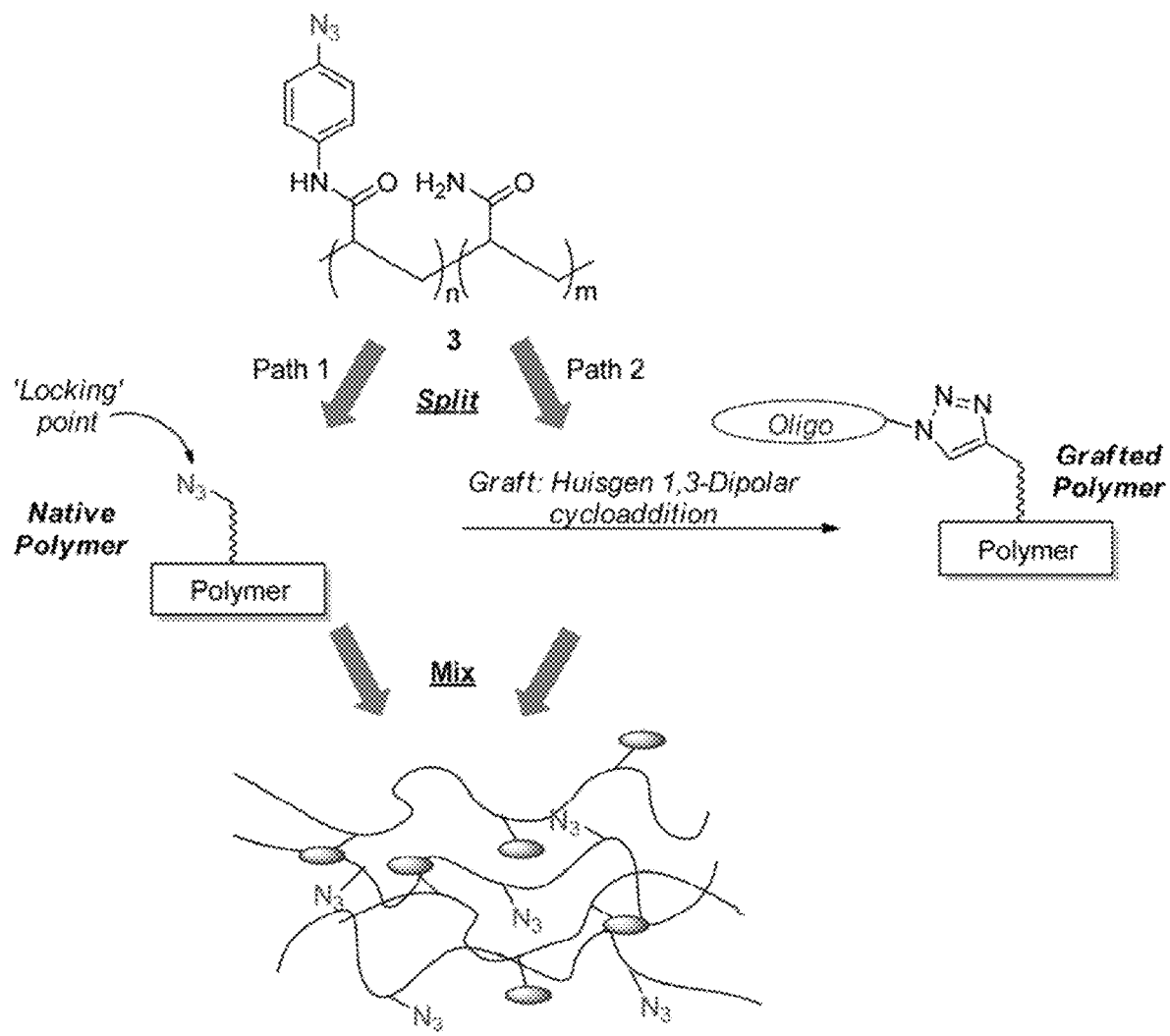
FIG. 16 illustrates a split and combine approach using an photoactive polymer.

The purified batch is then split with a portion (approximately ~80%) grafted in solution using, for example, copper catalyzed Huisgen 1,3-cycloaddition (FIG. 16: path 2). The grafted polymer can then be recombined with the unreacted material to provide a polymer mix that contains both paired-end primers as well as free photoactive groups capable of locking to both the wafer surface and neighboring polymer chains (see FIG. 16).

This photocoupling approach improves the polymer robustness to support both cluster growth and sequencing steps. Previous work has shown that dynamic silicon-free-acrylamide mixes are capable of supporting SBS but display undesirable "creases" faintly visible after clustering and becoming more pronounced during sequencing. Use of the photocoupling approach disclosed herein can improve the anchoring of the polymer to the wafer while decreasing excessive flexibility and maintaining access to the grafted primers.

Example 11

Coating Beads with PAZAM Using Thermal Crosslinking

Silica beads were obtained as a 10 wt. % solids suspension from Bang's Labs of Fishers, Ind. (PN SSO4N/9348, but note that many other bead composition and sizes can be used in a similar manner). An aliquot of 1 ml (100 mg) was transferred to a 1.5 ml eppendorf tube. The tube was centrifuged on a benchtop centrifuge (5000 rfu) for 30 sec to spin down the beads. The solution was removed by aspiration. Next, 1 ml of acetonitrile (Aldrich PN 34967) was added to the tube, the tube vortexed 30 seconds to homogenize the suspension, and then spun down again. This process was repeated 5 times to exchange the solvent. Finally, the last of the solvent was removed by aspiration (after centrifugation to spin down the beads).

In a separate 15 ml tube was added 5 ml of acetonitrile and 100 µl of 3-acrylamidopropyltrimethoxysilane (Gelest PN SIA0146.0). This solution was vortexed 15 seconds to mix the solution. Next, a polymerization inhibitor was added to the solution to prevent premature polymerization: 2 µl of N,N-diethylhydroxylamine (Aldrich PN 471593), was added to the 2 ml of silane solution to make the inhibitor concentration at 1000 ppm. Next, 1 ml of the silane solution with inhibitor solution was added to the beads. The tube was vortexed 30 seconds to homogenize the beads suspension in the silane solution. The beads were then allowed to react to the silane for 30 min at room temperature on a rotisserie mixer. The tube of beads was then centrifuged to spin down the beads, and the solution removed by aspiration. The beads were then solvent exchanged into acetonitrile containing 1000 ppm of N,N-diethylhydroxylamine polymerization inhibitor in a manner similar to that as described above.

After the silanization, the beads were solvent exchanged into Ethanol containing 1000 ppm of the polymerization inhibitor (by 5 successive centrifugation, aspiration, and new solvent additions). Next, the beads were solvent exchanged into Acetone containing 1000 ppm of the polymerization inhibitor. Finally, the residual acetone was removed by aspiration (after centrifugation of the beads), the tube of beads was capped with a kimwipe affixed by a rubber band to ensure dried beads wouldn't escape into the evacuation chamber. The beads were then placed in a vacuum oven pre-warmed to 40° C. and subjected to house vacuum (approx. 27 Torr) for 1 hr. The beads were then removed from the vacuum oven and 1 ml of HPLC grade water containing 1000 ppm of the polymerization inhibitor was added. The bead suspension was then homogenized by vortexing for 30 seconds.

In a separate 1.5 ml eppendorf tube, 10 ul of the aqueous suspension of beads from the previous step was added. Next, 1 ml of 1.0 wt % solution of PAZAM polymer in HPLC grade water was then added to the beads. The solution was homogenized by vortexing for 20 seconds on a benchtop vortexer, then centrifuged at 7000 rfu for 90 seconds to obtain the beads. The PAZAM polymer solution was then removed by aspiration. Next, 1 ml of a 2.0 wt. % PAZAM solution was added to the beads, and the solution homogenized by vortexing on a benchtop vortexer for 20 seconds. Next, the PAZAM was thermally grafted to the silane by reacting the tube at 60° C. for 1 hr. After the thermal grafting of PAZAM to the beads, the beads were washed with 5×1 ml HPLC grade water (using the solvent exchange method described above) at room temperature, and then 3×1 ml of pre-warmed (approximately 40° C.) HPLC grade water. The beads were diluted into 100 μl of HPLC grade water to make a 10 wt. % solids suspension.

P % and P7 oligonucleotides with 5' alkynyl functional groups were separately synthesized using standard oligonucleotide synthesis procedures (or alternatively, commercially obtained from oligonucleotide synthesis vendors). The oligonucleotide solution was provided as a 100 μM solution in HPLC water.

The grafting of the alkynyl-functionalized oligonucleotides to the azido-functionalized PAZAM was done as follows. To the 100 μl aliquot of the 10 wt. % solids of PAZAM-grafted beads solution was added 800 μl of 1×PBS buffer at pH 7.4. and 100 μl of the oligonucleotide solution. This solution was sparged with nitrogen gas for 10 minutes at mild bubbling nitrogen flow rate. Next, 2 μl of neat PMDETA (Aldrich PN 369497) was added. Next, 17 μl of a 160 mM aqueous solution of copper sulfate (Aldrich PN C2284) was then added. The solution turned purple as it was mixed by vortexing for 20 seconds. Finally, 25 μl of 40 mg/ml solution of sodium ascorbate (Aldrich PN A7631) in HPLC water was added, and the solution turned blue after mixing by vortexing for 20 seconds. The solution was allowed to react at 60° C. for 1 hr. Next, the beads were centrifuged, and the reaction solution removed by aspiration. The beads were washed into 1×PBS buffer (pH 7.4) in a similar manner as described previously (solvent exchanging using 5×1 ml washes of the buffer).

The oligo-functionalized beads were then loaded onto an empty microarray slide which was functionalized with 1.2 micron holes. Slides were prepared as described in U.S. Pat. No. 6,770,441. Beads were loaded as follows: the slide containing wells was pre-cleaned by immersing it into 0.1N NaOH for 5 min at room temperature, then vigorous washing with flowing HPLC grade water (about 100 ml) and dried under a nitrogen stream. Next, 10 μl of 200 proof Ethanol (Aldrich PN E7023) was added to the 100 μl of bead solution. The bead solution was then applied to the microscope slide via pipette. Next, the slide was placed in a vacuum oven pre-warmed to 40° C., and the slides allowed to evaporate for 30 min. The residual beads were removed from the surface of the microscope slide by the gentle manual application of an ethanol-saturated kimwipe.

To one slide prepared in this manner was added a solution of 10 μM of 5'-dye labeled (preferably Cy5) oligonucleotide in 5×SSC buffer (Aldrich PN 56639) with the reverse complement to that oligo which was immobilized to the PAZAM-grafted bead. The slide was then covered with a glass coverslip. The slide was allowed to hybridize at room temperature for 30 minutes. Next, the coverslip was removed and the slide was washed with copious amounts of flowing 5×SSC buffer (about 100 ml). Finally, to the slide was added 100 μl of 5×SSC buffer and then a coverslip, and the slide was imaged on a GE Typhoon FLA 9500, scanning at the Cy5 dye channel setting with a 500 PMT setting.

To another slide prepared in this manner was added a rubber gasket and another microscope slide which was pre-drilled with the appropriate location of holes in the glass to enable liquid introduction via an Illumina HiSeq sequencing instrument. DNA clusters were then grown on the slides and the clusters were sequenced as per manufacturer's instructions for the HiSeq 2000 (Illumina Inc., San Diego, Calif.). This slide was shown to be able to sequence up to 150 bp of sample DNA per cluster.

What is claimed is:

1. A method of immobilizing a polymer to a surface of a substrate, comprising:
contacting a polymer with a surface of a substrate;
wherein said polymer comprising a recurring unit of Formula (Ia) and a recurring unit of Formula (II):

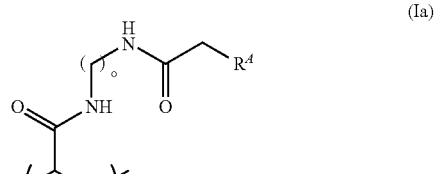

(Ia)

(II)

wherein:
$R^1$ is H, alkyl, alkoxy, alkenyl, alkynyl, or optionally substituted variants thereof;
$R^4$ is selected from the group consisting of amine, optionally substituted alkene, optionally substituted alkyne, oxo-amine, azido, formyl, halo, hydroxy, hydrazinyl, hydrazonyl, thiocyanate, carboxylic acid, glycidyl, activated ester, epoxy, aziridine, triazoline, and thiol;
each of the —$(CH_2)_o$— units is optionally substituted;
$o$ is an integer between 1 and 50;

each $R^4$, $R^{4'}$, $R^5$ and $R^{5'}$ is independently selected from the group consisting of H, $R^6$, $OR^6$, $-C(O)OR^6$, $-C(O)R^6$, $-OC(O)R^6$, $-C(O)NR^7R^8$, and $-NR^7R^8$;

each $R^6$ is independently H, OH, alkyl, cycloalkyl, hydroxyalkyl, aryl, heteroaryl, or heterocyclyl, or an optionally substituted variant thereof; and each $R^7$ and $R^8$ is independently H or alkyl, or $R^7$ and $R^8$ are joined together with the atom or atoms to which they are attached to form a heterocycle;

provided that, when $R^1$ is H, o is 5, and $R^4$ is halo, then $R^4$ is not bromo;

wherein the surface comprises a plurality of functional groups and the polymer is attached to the surface via the plurality of functional groups.

2. The method of claim 1, wherein the plurality of functional groups are selected from the group consisting of acrylamide, alkene, alkyne, nitrene, aldehyde, hydrazine, activated ester, glycidyl ether, amine, maleimide, and benzoyl ester with a phosphine substituent in the ortho position, and combinations thereof.

3. The method of claim 2, wherein the plurality of functional groups are components of a functionalized silane on the surface.

4. The method of claim 1, wherein $R^4$ is azido.

5. The method of claim 4, wherein $R^1$ is H or alkyl.

6. The method of claim 1, wherein:
$R^4$ is $-C(O)NR^7R^8$; and
$R^{4'}$, $R^5$, and $R^{5'}$ are each independently H or alkyl.

7. The method of claim 6, wherein $R^7$ and $R^8$ are each independently H or alkyl.

8. The method of claim 1, wherein the recurring unit of Formula (Ia) is

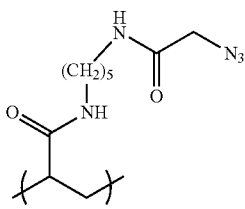

and the recurring unit of Formula (II) is

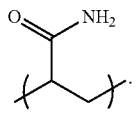

9. The method of claim 1, wherein the functional groups on the surface comprise alkene, alkyne, acrylamide, or nitrene.

10. The method of claim 1, wherein the surface comprises both polymer-coated regions and inert regions.

11. The method of claim 1, wherein the substrate is part of a flow cell.

12. A method of preparing an array of polynucleotides, comprising:
providing a substrate comprising a polymer immobilized on a surface of the substrate;
reacting a plurality of first oligonucleotides and a plurality of second oligonucleotides with the polymer;
wherein the polymer comprising a recurring unit of Formula (Ia) and a recurring unit of Formula (II):

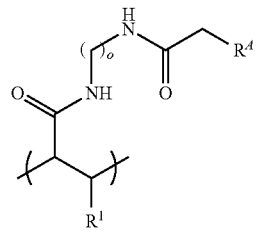

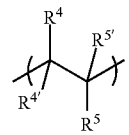

wherein:
$R^1$ is H, alkyl, alkoxy, alkenyl, alkynyl, or optionally substituted variants thereof;

$R^4$ is selected from the group consisting of amine, optionally substituted alkene, optionally substituted alkyne, oxo-amine, azido, formyl, halo, hydroxy, hydrazinyl, hydrazonyl, thiocyanate, carboxylic acid, glycidyl, activated ester, epoxy, aziridine, triazoline, and thiol;

each of the $-(CH_2)_o-$ units is optionally substituted;

o is an integer between 1 and 50;

each $R^4$, $R^{4'}$, $R^5$ and $R^{5'}$ is independently selected from the group consisting of H, $R^6$, $OR^6$, $-C(O)OR^6$, $-C(O)R^6$, $-OC(O)R^6$, $-C(O)NR^7R^8$, and $-NR^7R^8$;

each $R^6$ is independently H, OH, alkyl, cycloalkyl, hydroxyalkyl, aryl, heteroaryl, or heterocyclyl, or an optionally substituted variant thereof; and each $R^7$ and $R^8$ is independently H or alkyl, or $R^7$ and $R^8$ are joined together with the atom or atoms to which they are attached to form a heterocycle;

provided that, when $R^1$ is H, o is 5, and $R^4$ is halo, then $R^4$ is not bromo.

13. The method of claim 12, further comprising contacting the plurality of first oligonucleotides attached to the polymer coating with templates to be amplified, each template comprising at the 3' end a sequence capable of hybridizing to the first oligonucleotides and at the 5' end a sequence the complement of which is capable of hybridizing to the second oligonucleotides.

14. The method of claim 13, further comprising amplifying the templates using the first oligonucleotides and the second oligonucleotides, thereby generating a clustered array of polynucleotides.

15. The method of claim 12, wherein $R^4$ is azido.

16. The method of claim 15, wherein $R^1$ is H or alkyl.

17. The method of claim 12, wherein:
$R^4$ is $-C(O)NR^7R^8$; and
$R^{4'}$, $R^5$, and $R^{5'}$ are each independently H or alkyl.

18. The method of claim 12, wherein the recurring unit of Formula (Ia) is

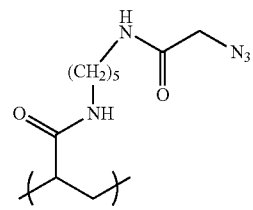

and the recurring unit of Formula (II) is

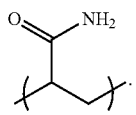

19. The method of claim 12, wherein each first oligonucleotide or each second oligonucleotide comprise a functional group selected from the group consisting of alkyne, amine, and aldehyde.

20. The method of claim 12, wherein the substrate is part of a flow cell.

21. A method of determining a nucleotide sequence of a polynucleotide, comprising the steps of:
   (a) contacting a polynucleotide polymerase with polynucleotide clusters attached to a surface of a substrate via a polymer immobilized on the surface of the substrate;
   (b) providing nucleotides to the surface of the substrate such that a detectable signal is generated when one or more nucleotides are utilized by the polynucleotide polymerase;
   (c) detecting signals at one or more polynucleotide clusters; and
   (d) repeating steps (b) and (c), thereby determining a nucleotide sequence of a polynucleotide present at the one or more polynucleotide clusters;
   wherein the polymer comprising a recurring unit of Formula (Ia) and a recurring unit of Formula (II):

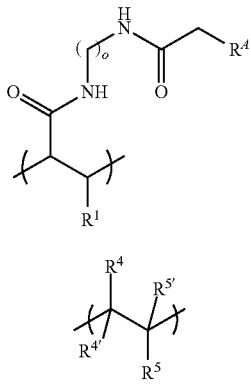

(Ia)

(II)

wherein:
   $R^1$ is H, alkyl, alkoxy, alkenyl, alkynyl, or optionally substituted variants thereof;
   $R^4$ is selected from the group consisting of amine, optionally substituted alkene, optionally substituted alkyne, oxo-amine, azido, formyl, halo, hydroxy, hydrazinyl, hydrazonyl, thiocyanate, carboxylic acid, glycidyl, activated ester, epoxy, aziridine, triazoline, and thiol;
   each of the $-(CH_2)_o-$ units is optionally substituted;
   o is an integer between 1 and 50;
   each $R^4$, $R^{4'}$, $R^5$ and $R^{5'}$ is independently selected from the group consisting of H, $R^6$, $OR^6$, $-C(O)OR^6$, $-C(O)R^6$, $-OC(O)R^6$, $-C(O)NR^7R^8$, and $-NR^7R^8$;
   each $R^6$ is independently H, OH, alkyl, cycloalkyl, hydroxyalkyl, aryl, heteroaryl, or heterocyclyl, or an optionally substituted variant thereof; and
   each $R^7$ and $R^8$ is independently H or alkyl, or $R^7$ and $R^8$ are joined together with the atom or atoms to which they are attached to form a heterocycle;
   provided that, when $R^1$ is H, o is 5, and $R^4$ is halo, then $R^4$ is not bromo.

22. The method of claim 21, wherein $R^4$ is azido.

23. The method of claim 22, wherein $R^1$ is H or alkyl.

24. The method of claim 21, wherein:
   $R^4$ is $-C(O)NR^7R^8$; and
   $R^{4'}$, $R^5$, and $R^{5'}$ are each independently H or alkyl.

25. The method of claim 21, wherein the recurring unit of Formula (Ia) is:

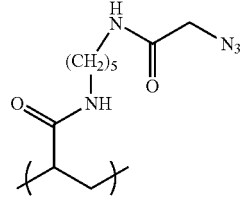

and the recurring unit of Formula (II) is

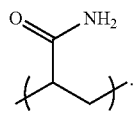

26. The method of claim 21, wherein the detectable signal comprises an optical signal.

27. The method of claim 21, wherein the substrate is part of a flow cell.

* * * * *